(12) United States Patent
Wolfgang et al.

(10) Patent No.: US 7,402,664 B2
(45) Date of Patent: *Jul. 22, 2008

(54) NUCLEIC ACIDS AND EXPRESSION VECTORS COMPRISING CAROTENOID BINDING PEPTIDES

(75) Inventors: Aehle Wolfgang, Delfgauw (NL); Toby M. Baldwin, Palo Alto, CA (US); Franciscus J. C. van Gastel, Union City, CA (US); Giselle G. Janssen, San Carlos, CA (US); Christopher J. Murray, Soquel, CA (US); Huaming Wang, Fremont, CA (US); Deborah S. Winetzky, Foster City, CA (US)

(73) Assignee: Genencor International, Inc., Palo Alto, CA (US)

( * ) Notice: Subject to any disclaimer, the term of this patent is extended or adjusted under 35 U.S.C. 154(b) by 552 days.

This patent is subject to a terminal disclaimer.

(21) Appl. No.: 10/235,043

(22) Filed: Sep. 3, 2002

(65) Prior Publication Data

US 2005/0058996 A1    Mar. 17, 2005

(51) Int. Cl.
*C07H 21/02* (2006.01)
*C07H 21/04* (2006.01)
*A61K 38/04* (2006.01)
*A61K 38/00* (2006.01)
*C12N 15/00* (2006.01)

(52) U.S. Cl. .................... 536/23.1; 536/23.4; 530/329; 530/300; 435/252.3; 435/320.1

(58) Field of Classification Search .............. 530/300, 530/327; 536/23.1, 23.2; 435/440, 252.3, 435/320.1
See application file for complete search history.

(56) References Cited

U.S. PATENT DOCUMENTS

2005/0042684 A1*   2/2005   Aehle et al. ................. 435/7.1

OTHER PUBLICATIONS

Aehle et al. Sequence Alignment—Seq Id No. 24.*

* cited by examiner

*Primary Examiner*—Yong D Pak
(74) *Attorney, Agent, or Firm*—Danisco A/S

(57) ABSTRACT

The present application relates to peptides which bind to a target stain, phenol oxidizing enzyme-binding peptide complexes wherein the binding peptide is attached to the C-terminus of the phenol oxidizing enzyme or is inserted or substituted into the phenol oxidizing enzyme. In a preferred embodiment the phenol oxidizing enzyme is a laccase specifically *Stachybotrys* oxidase B and variants thereof. The invention provides expression vectors comprising the phenol oxidizing enzyme-binding peptide complex as well as host cells comprising the vectors.

3 Claims, 10 Drawing Sheets

| Binding Peptide | SEQ ID NO: | Binding Peptide | SEQ ID NO: |
|---|---|---|---|
| TGMSLHH | SEQ ID NO: 2 | PNSHPHW | SEQ ID NO: 52 |
| PLTTSPV | SEQ ID NO: 3 | PTRATPS | SEQ ID NO: 53 |
| SLLNATK | SEQ ID NO: 4 | PHPTNLA | SEQ ID NO: 54 |
| QNEHNLA | SEQ ID NO: 5 | QISQSQI | SEQ ID NO: 55 |
| PFNTLDR | SEQ ID NO: 6 | PSSTWHP | SEQ ID NO: 56 |
| RNYTGAA | SEQ ID NO: 7 | ITWDHIN | SEQ ID NO: 57 |
| LPGPSHF | SEQ ID NO: 8 | SPNPTST | SEQ ID NO: 58 |
| SKNEGRT | SEQ ID NO: 9 | QTSALSR | SEQ ID NO: 59 |
| WYANKTM | SEQ ID NO: 10 | ERRPSKA | SEQ ID NO: 60 |
| FPKTTPI | SEQ ID NO: 11 | SMFSKAA | SEQ ID NO: 61 |
| ISDFKFM | SEQ ID NO: 12 | QPTLGQM | SEQ ID NO: 62 |
| GNSAWFF | SEQ ID NO: 13 | TRTMNFT | SEQ ID NO: 63 |
| NTSIQRN | SEQ ID NO: 14 | KPWNAEK | SEQ ID NO: 64 |
| SSKWHYN | SEQ ID NO: 15 | RADTSGH | SEQ ID NO: 65 |
| YGYLPSR | SEQ ID NO: 16 | KASVAQQ | SEQ ID NO: 66 |
| TPSYWQD | SEQ ID NO: 17 | SGLWPGF | SEQ ID NO: 67 |
| NTSRLFH | SEQ ID NO: 18 | NRSAEGV | SEQ ID NO: 68 |
| SQQQRQY | SEQ ID NO: 19 | STRLTTE | SEQ ID NO: 69 |
| APSENQV | SEQ ID NO: 20 | PPHGALR | SEQ ID NO: 70 |
| KYLNDQR | SEQ ID NO: 21 | NGTWSAK | SEQ ID NO: 71 |
| KPTATNI | SEQ ID NO: 22 | APSRMMI | SEQ ID NO: 72 |
| APPAQGS | SEQ ID NO: 23 | NTLWQSP | SEQ ID NO: 73 |
| KASAPAL | SEQ ID NO: 24 | KHTHMTA | SEQ ID NO: 74 |
| KSDHWKN | SEQ ID NO: 25 | SFTKNNW | SEQ ID NO: 75 |
| LVNKHQS | SEQ ID NO: 26 | KHSSLTT | SEQ ID NO: 76 |
| KLNANNF | SEQ ID NO: 27 | STSLLNA | SEQ ID NO: 77 |
| TQHMKKA | SEQ ID NO: 28 | KYQYKHA | SEQ ID NO: 78 |
| SHSPYSR | SEQ ID NO: 29 | PYSHSRF | SEQ ID NO: 79 |
| LQSHKDH | SEQ ID NO: 30 | ESARWSL | SEQ ID NO: 80 |
| SSKSLAV | SEQ ID NO: 31 | LPQIQRI | SEQ ID NO: 81 |
| HDSLHGK | SEQ ID NO: 32 | NPDLRHN | SEQ ID NO: 82 |
| TDWNGWH | SEQ ID NO: 33 | LPTPKAH | SEQ ID NO: 83 |
| VPWLTNS | SEQ ID NO: 34 | TQTSLTK | SEQ ID NO: 84 |
| LSPQDRY | SEQ ID NO: 35 | FSLYDAT | SEQ ID NO: 85 |
| LTHGPKH | SEQ ID NO: 36 | PVHTHNW | SEQ ID NO: 86 |
| HLNQHHT | SEQ ID NO: 37 | SMYVEGN | SEQ ID NO: 87 |
| VSSPHIY | SEQ ID NO: 38 | TSQHYRS | SEQ ID NO: 88 |
| MTHPLVH | SEQ ID NO: 39 | HYTTDRH | SEQ ID NO: 89 |
| HTFLQTH | SEQ ID NO: 40 | | |
| NTSYQYR | SEQ ID NO: 41 | | |
| GHSMLTN | SEQ ID NO: 42 | | |
| MTPAKPS | SEQ ID NO: 43 | | |
| ISDYPNP | SEQ ID NO: 44 | | |
| DIQRMML | SEQ ID NO: 45 | | |
| FVLPPVS | SEQ ID NO: 46 | | |
| TMGTLLA | SEQ ID NO: 47 | | |
| HIRAPGN | SEQ ID NO: 48 | | |
| HTSPTSH | SEQ ID NO: 49 | | |
| SSDLPPY | SEQ ID NO: 50 | | |
| WGLASQL | SEQ ID NO: 51 | | |

FIG._1A

| Binding Peptide | SEQ ID NO: | Binding Peptide | SEQ ID NO: |
|---|---|---|---|
| SFGHSTFWHPVL | SEQ ID NO: 90 | NNLAFTPSGTLR | SEQ ID NO: 144 |
| TPPIYWHRMADT | SEQ ID NO: 91 | HFAYTKPMRIPQ | SEQ ID NO: 145 |
| IERSAPATAPPP | SEQ ID NO: 92 | SSWLHDLPVLPL | SEQ ID NO: 146 |
| NPTTTYKMTPTM | SEQ ID NO: 93 | SVTYQNYGMNTM | SEQ ID NO: 147 |
| HVQILQLAAPAL | SEQ ID NO: 94 | YAHAGKTTFLLG | SEQ ID NO: 148 |
| HVTNPTSPRPVA | SEQ ID NO: 95 | HPPSLPNNVVHP | SEQ ID NO: 149 |
| TPWMQNTIYRPH | SEQ ID NO: 96 | SSKNPLADNPRQ | SEQ ID NO: 150 |
| LPSLLVSHLFDM | SEQ ID NO: 97 | HLSRFESLMHLM | SEQ ID NO: 151 |
| SFPGKFLSLHTS | SEQ ID NO: 98 | WLHLPGSAQNHL | SEQ ID NO: 152 |
| YKNAIPEDLREL | SEQ ID NO: 99 | RNRPHIIRPPPP | SEQ ID NO: 153 |
| SGEFNQWPSSKP | SEQ ID NO: 100 | TKNWMPHQDAPL | SEQ ID NO: 154 |
| SYLNHLPQRPLS | SEQ ID NO: 101 | QNQLDMTKLTML | SEQ ID NO: 155 |
| AGNYMFLGYRSL | SEQ ID NO: 102 | NPPPPTPPPAPP | SEQ ID NO: 156 |
| TATHLSPGAWRP | SEQ ID NO: 103 | SYTQILAHPKHA | SEQ ID NO: 157 |
| YHTPSTGGASPV | SEQ ID NO: 104 | QTGQAHQQPSAT | SEQ ID NO: 158 |
| SSDVPQAARNDA | SEQ ID NO: 105 | NIPYLAMPTKRM | SEQ ID NO: 159 |
| LSKKITTDEWFA | SEQ ID NO: 106 | LRSDQYFHHTTL | SEQ ID NO: 160 |
| SQIKHPHASSSI | SEQ ID NO: 107 | HLYRNNDTFAPR | SEQ ID NO: 161 |
| SMQLQLIPSTPT | SEQ ID NO: 108 | GSVGYMRPPKVY | SEQ ID NO: 162 |
| YDHNYTMNNALN | SEQ ID NO: 109 | LPAQMTPVSVVR | SEQ ID NO: 163 |
| NAFETQRLAQLG | SEQ ID NO: 110 | QQLINYSMPLPM | SEQ ID NO: 164 |
| AQASRINTYPPT | SEQ ID NO: 111 | YPTFSYVSPEVT | SEQ ID NO: 165 |
| HQTSNGPTPLVP | SEQ ID NO: 112 | TYTSQSRSPADD | SEQ ID NO: 166 |
| TFTPYAYQSNMS | SEQ ID NO: 113 | AYWDFIQAKQAM | SEQ ID NO: 167 |
| TTLTYNWKSAHQ | SEQ ID NO: 114 | GLQTIDLNLYNA | SEQ ID NO: 168 |
| EMVSKKTLTSVL | SEQ ID NO: 115 | TIMHTTVPGHLQ | SEQ ID NO: 169 |
| ELVKNPYTRSLT | SEQ ID NO: 116 | ITQTRFIAAPLH | SEQ ID NO: 170 |
| LPPQPPFITTML | SEQ ID NO: 117 | HVLRHPGNPNTF | SEQ ID NO: 171 |
| SPTTLVQMPWPR | SEQ ID NO: 118 | AHHDDKHSAPDT | SEQ ID NO: 172 |
| SAQNGVISYDLG | SEQ ID NO: 119 | DPSNKRYPQSYK | SEQ ID NO: 173 |
| QIWHPNYPGSL | SEQ ID NO: 120 | LNANLPANSVLA | SEQ ID NO: 174 |
| TNQLHRTHPSGQ | SEQ ID NO: 121 | NINKHYFQSPIM | SEQ ID NO: 175 |
| NDHREVRTRLFL | SEQ ID NO: 122 | TGMKAPSGIYTG | SEQ ID NO: 176 |
| HSFRVTSNLSPP | SEQ ID NO: 123 | QVNFSNHSSRSP | SEQ ID NO: 177 |
| YNTSIMQKAVSP | SEQ ID NO: 124 | NSPMQALHDPHS | SEQ ID NO: 178 |
| ASPNTHTPAARA | SEQ ID NO: 125 | VENLTQPPPPFG | SEQ ID NO: 179 |
| TLYQDQKQKQRF | SEQ ID NO: 126 | QTLNMEPRSYSN | SEQ ID NO: 180 |
| EILYMPPSTHAL | SEQ ID NO: 127 | IAPGGSIKAPPR | SEQ ID NO: 181 |
| TPFIYLKSSSLP | SEQ ID NO: 128 | DSLTSNSQPPSS | SEQ ID NO: 182 |
| DIPSFETIPPRP | SEQ ID NO: 129 | TPPSLYYLGPLP | SEQ ID NO: 183 |
| GHRPHAIKPPPP | SEQ ID NO: 130 | QPMLFGLRGAFA | SEQ ID NO: 184 |
| SDYSSAATYYGH | SEQ ID NO: 131 | HNAMLPQYLLLS | SEQ ID NO: 185 |
| SSTSPLLPHMLL | SEQ ID NO: 132 | SFNYATFPLVPL | SEQ ID NO: 186 |
| TSEHTLASKYQS | SEQ ID NO: 133 | LMARLPDTYTQV | SEQ ID NO: 187 |
| SHGIATSETTSN | SEQ ID NO: 134 | TAPIASLTYPLI | SEQ ID NO: 188 |
| MNPSSSQHKNSH | SEQ ID NO: 135 | THHFQMPPPPML | SEQ ID NO: 189 |
| PWASITPPPLLR | SEQ ID NO: 136 | MDLQPPSSPRST | SEQ ID NO: 190 |
| QNLQPPQGFTLG | SEQ ID NO: 137 | KMMSNSLTLRLP | SEQ ID NO: 191 |
| TTSFSEGILIRS | SEQ ID NO: 138 | TPPQELITASRA | SEQ ID NO: 192 |
| NVPTSNTHFGLH | SEQ ID NO: 139 | YNKPLLQSQTLL | SEQ ID NO: 193 |
| TGSMELWTLQTQ | SEQ ID NO: 140 | HSLAGIARMLME | SEQ ID NO: 194 |
| SPARSTVGPYEL | SEQ ID NO: 141 | | |
| SHAITATHLEPS | SEQ ID NO: 142 | | |
| LQLQLLPYAFPV | SEQ ID NO: 143 | | |

FIG._1B

| Binding Peptide | SEQ ID NO: | Binding Peptide | SEQ ID NO: |
|---|---|---|---|
| SAAQLNM | SEQ ID NO: 195 | NSTDRST | SEQ ID NO: 244 |
| SLHQSNY | SEQ ID NO: 196 | SPTAAQS | SEQ ID NO: 245 |
| LGPPPFR | SEQ ID NO: 197 | TTTTSLL | SEQ ID NO: 246 |
| TTAPPTT | SEQ ID NO: 198 | PSMLNAT | SEQ ID NO: 247 |
| PSHQQQV | SEQ ID NO: 199 | NTHSGKP | SEQ ID NO: 248 |
| PTFIKSN | SEQ ID NO: 200 | HPPWMSQ | SEQ ID NO: 249 |
| SYPLASR | SEQ ID NO: 201 | TRSTHTT | SEQ ID NO: 250 |
| SKISVTL | SEQ ID NO: 202 | GRHPLMN | SEQ ID NO: 251 |
| TNASPLH | SEQ ID NO: 203 | TQKEHQR | SEQ ID NO: 252 |
| PLNPNNM | SEQ ID NO: 204 | ALKEALS | SEQ ID NO: 253 |
| SGRPYET | SEQ ID NO: 205 | HTTTSHH | SEQ ID NO: 254 |
| GWTMAQR | SEQ ID NO: 206 | EATFHKD | SEQ ID NO: 255 |
| KLNDMLL | SEQ ID NO: 207 | RLSDPMH | SEQ ID NO: 256 |
| RTTPPWM | SEQ ID NO: 208 | TDFFGRV | SEQ ID NO: 257 |
| YQSMSYS | SEQ ID NO: 209 | GQNPMKS | SEQ ID NO: 258 |
| TSGPSPM | SEQ ID NO: 210 | TAPSFTK | SEQ ID NO: 259 |
| HAKAPST | SEQ ID NO: 211 | FDSKNTP | SEQ ID NO: 260 |
| PHSRGLA | SEQ ID NO: 212 | QQLNTPR | SEQ ID NO: 261 |
| QQSWPPF | SEQ ID NO: 213 | HIPSALL | SEQ ID NO: 262 |
| PNNSTPV | SEQ ID NO: 214 | ELTPALH | SEQ ID NO: 263 |
| TTTWWHV | SEQ ID NO: 215 | TPPTKKQ | SEQ ID NO: 264 |
| FSQSDPW | SEQ ID NO: 216 | SGIPRNS | SEQ ID NO: 265 |
| KPTVDRN | SEQ ID NO: 217 | VQOVTRY | SEQ ID NO: 266 |
| DTWTHSS | SEQ ID NO: 218 | KGMHTTD | SEQ ID NO: 267 |
| KDMPTQF | SEQ ID NO: 219 | PMWGTHL | SEQ ID NO: 268 |
| ISNNTHN | SEQ ID NO: 220 | NAAKLEQ | SEQ ID NO: 269 |
| INTPHSM | SEQ ID NO: 221 | PQEALQL | SEQ ID NO: 270 |
| KDGNPGY | SEQ ID NO: 222 | SRDMHPH | SEQ ID NO: 271 |
| KNPNNDR | SEQ ID NO: 223 | GPETPYQ | SEQ ID NO: 272 |
| SSWPAMP | SEQ ID NO: 224 | SLVQSLE | SEQ ID NO: 273 |
| DNQAFGL | SEQ ID NO: 225 | NLTPMAR | SEQ ID NO: 274 |
| PHKDPQR | SEQ ID NO: 226 | LQSPPLK | SEQ ID NO: 275 |
| TKCPSST | SEQ ID NO: 227 | QKHAFRS | SEQ ID NO: 276 |
| EANTQTA | SEQ ID NO: 228 | PWQIKLT | SEQ ID NO: 277 |
| HQMSSQT | SEQ ID NO: 229 | | |
| TSNHQSS | SEQ ID NO: 230 | | |
| LPLKNSA | SEQ ID NO: 231 | | |
| PSATSLM | SEQ ID NO: 232 | | |
| STPGSLQ | SEQ ID NO: 233 | | |
| HHQNALH | SEQ ID NO: 234 | | |
| DPLRQTT | SEQ ID NO: 235 | | |
| NPKTNVS | SEQ ID NO: 236 | | |
| SNLAPML | SEQ ID NO: 237 | | |
| FTAMNNS | SEQ ID NO: 238 | | |
| EPHARSM | SEQ ID NO: 239 | | |
| NSLSPGN | SEQ ID NO: 240 | | |
| EHNRQKN | SEQ ID NO: 241 | | |
| TPTSPPG | SEQ ID NO: 242 | | |
| NLATSNA | SEQ ID NO: 243 | | |

FIG._1C

| Binding Peptide | SEQ ID NO: | Binding Peptide | SEQ ID NO: |
|---|---|---|---|
| GMEPMHYYSRHL | SEQ ID NO: 278 | KAIGMSTGPLTQ | SEQ ID NO: 327 |
| QTTNSNMAPALS | SEQ ID NO: 279 | LHVTTTIPGGLR | SEQ ID NO: 328 |
| TPPATLVHWADP | SEQ ID NO: 280 | SVPSPSPPWSRP | SEQ ID NO: 329 |
| MQNLHEMAWTIQ | SEQ ID NO: 281 | VASANPHSMTSW | SEQ ID NO: 330 |
| KSLTFPLTATQT | SEQ ID NO: 282 | QDATSRFSGLAS | SEQ ID NO: 331 |
| VSHKTGNTYSR | SEQ ID NO: 283 | AEAITAIPLPVP | SEQ ID NO: 332 |
| KVNIPHIHDRIA | SEQ ID NO: 284 | MDPFATIPSTHP | SEQ ID NO: 333 |
| QIPRLIPHPLAM | SEQ ID NO: 285 | EGNARLAQSLIQ | SEQ ID NO: 334 |
| YQNKIHSRTIAH | SEQ ID NO: 286 | MHSPFCSSPCSP | SEQ ID NO: 335 |
| ESRLSSSPWSL | SEQ ID NO: 287 | SGMPPTITWTRP | SEQ ID NO: 336 |
| ASSHDQHSTEG | SEQ ID NO: 288 | WEATPNFMSKII | SEQ ID NO: 337 |
| SPLTQYNTPRHP | SEQ ID NO: 289 | AVSLVPPNLATH | SEQ ID NO: 338 |
| IKSQADPARLYI | SEQ ID NO: 290 | VPNMTPSSYLSA | SEQ ID NO: 339 |
| NKTPNSMTPIFM | SEQ ID NO: 291 | LQPQTWSWARGA | SEQ ID NO: 340 |
| APPQSPVYLVPL | SEQ ID NO: 292 | TEPTVKHPPLRI | SEQ ID NO: 341 |
| LPAQYQTIPGSL | SEQ ID NO: 293 | VALPNQPPRAGL | SEQ ID NO: 342 |
| SSVPMDVLTPVV | SEQ ID NO: 294 | GLGYWVMPAPTS | SEQ ID NO: 343 |
| ALGSMTWSPPPL | SEQ ID NO: 295 | HNLYMTPPSIMN | SEQ ID NO: 344 |
| QGSHNSSSAISW | SEQ ID NO: 296 | HAEKILSSPGPA | SEQ ID NO: 345 |
| SSIMNTAVLGHD | SEQ ID NO: 297 | HNMLPPRCCLLP | SEQ ID NO: 346 |
| STLWYRSDMTHG | SEQ ID NO: 298 | | |
| ASTVYQPYVVHA | SEQ ID NO: 299 | | |
| AARNDQVSHMHM | SEQ ID NO: 300 | | |
| EVFQNWPQSLHK | SEQ ID NO: 301 | | |
| QALTHPMTKPPT | SEQ ID NO: 302 | | |
| SYTKPDQHALAF | SEQ ID NO: 303 | | |
| DLFSAHHTGGAL | SEQ ID NO: 304 | | |
| LVGHQLNLHALR | SEQ ID NO: 305 | | |
| HGEVARLVPFRG | SEQ ID NO: 306 | | |
| ACKLEMGLSC | SEQ ID NO: 307 | | |
| SAIPTMGRHAHP | SEQ ID NO: 308 | | |
| QSTYSNIGRDDS | SEQ ID NO: 309 | | |
| KALSASEPLPQG | SEQ ID NO: 310 | | |
| VASRLTGSVASA | SEQ ID NO: 311 | | |
| SIGELSGPVRHQ | SEQ ID NO: 312 | | |
| QQNPYIPSSVTR | SEQ ID NO: 313 | | |
| NVFMGSLHASLV | SEQ ID NO: 314 | | |
| SPHSMLQNPSGP | SEQ ID NO: 315 | | |
| NEELTSHTNQHL | SEQ ID NO: 316 | | |
| YLPSTFAPPLPL | SEQ ID NO: 317 | | |
| SVQGSPLDSTNH | SEQ ID NO: 318 | | |
| FSTDDSPFPFAA | SEQ ID NO: 319 | | |
| VQQATSGLARPH | SEQ ID NO: 320 | | |
| SDQASLLDGWRF | SEQ ID NO: 321 | | |
| NTLMINPTQAHL | SEQ ID NO: 322 | | |
| AHEGRNYGLVIK | SEQ ID NO: 323 | | |
| GDSTLFNTWQSS | SEQ ID NO: 324 | | |
| IVRVTDGTPSPG | SEQ ID NO: 325 | | |
| SSPLQTSPPWPY | SEQ ID NO: 326 | | |

FIG._1D

| Binding Peptide | SEQ ID NO: | Binding Peptide | SEQ ID NO: |
|---|---|---|---|
| TQPPGSS | SEQ ID NO: 347 | ANHWIASPYWSL | SEQ ID NO: 396 |
| MKPQLST | SEQ ID NO: 348 | TVGTHSMRTPRC | SEQ ID NO: 397 |
| HSLFYSWGPSLD | SEQ ID NO: 349 | YFQATELSPNNP | SEQ ID NO: 398 |
| VRMQMNTGLPQR | SEQ ID NO: 350 | SSPHLTE | SEQ ID NO: 399 |
| PHTNEIV | SEQ ID NO: 351 | KYPENMEVIRPF | SEQ ID NO: 400 |
| PYMQLRN | SEQ ID NO: 352 | TSSGSNL | SEQ ID NO: 401 |
| ARPTPLL | SEQ ID NO: 353 | SPSLPRMDVSTP | SEQ ID NO: 402 |
| LDTIDTNPPVHS | SEQ ID NO: 354 | ITLPHAAMHRAY | SEQ ID NO: 403 |
| PTHPLPT | SEQ ID NO: 355 | HYFPNPLSAHPP | SEQ ID NO: 404 |
| NSWCAAT | SEQ ID NO: 356 | MVPSYMR | SEQ ID NO: 405 |
| IPTSLMAHPHPA | SEQ ID NO: 357 | TEPHKAN | SEQ ID NO: 406 |
| QGQSQQS | SEQ ID NO: 358 | ASAQHKVNFPRW | SEQ ID NO: 407 |
| NAPAMKL | SEQ ID NO: 359 | PHHSRAR | SEQ ID NO: 408 |
| TLWPPRA | SEQ ID NO: 360 | SLHYNQA | SEQ ID NO: 409 |
| GQQDRREPIII | SEQ ID NO: 361 | SPTTGQS | SEQ ID NO: 410 |
| RIPAEKV | SEQ ID NO: 362 | PYLPSIP | SEQ ID NO: 411 |
| MPSPTYQ | SEQ ID NO: 363 | PSLPSIP | SEQ ID NO: 412 |
| KSTWQGL | SEQ ID NO: 364 | KHPQSPP | SEQ ID NO: 413 |
| SLPAQPRLTHLW | SEQ ID NO: 365 | PPRYAEL | SEQ ID NO: 414 |
| HWNTAALNHMRF | SEQ ID NO: 366 | SQLALQQ | SEQ ID NO: 415 |
| THQTTELLPRAS | SEQ ID NO: 367 | DSNSIQV | SEQ ID NO: 416 |
| VLALVKTSLNEP | SEQ ID NO: 368 | NWHPTLP | SEQ ID NO: 417 |
| GTYNLPNPPPPL | SEQ ID NO: 369 | SPTLPPP | SEQ ID NO: 418 |
| LPNRTPV | SEQ ID NO: 370 | SKHPPSSPHQSP | SEQ ID NO: 419 |
| GGTCFLA | SEQ ID NO: 371 | HDWAHPL | SEQ ID NO: 420 |
| RTESFSPLSFSS | SEQ ID NO: 372 | MTSHTQA | SEQ ID NO: 421 |
| ETVSNFSNVSTK | SEQ ID NO: 373 | EPTTTLPTVGR | SEQ ID NO: 422 |
| SEPARTP | SEQ ID NO: 374 | QAHNFTS | SEQ ID NO: 423 |
| GSSPLPLKFTGP | SEQ ID NO: 375 | KVSRENYTLVAL | SEQ ID NO: 424 |
| IPNHYTHYASPP | SEQ ID NO: 376 | TVLSPLTQTLYF | SEQ ID NO: 425 |
| TWGQPHG | SEQ ID NO: 377 | ITFDRTQQRVDD | SEQ ID NO: 426 |
| LKAQEFKATPPV | SEQ ID NO: 378 | YTKPYP | SEQ ID NO: 427 |
| APRSDSLILSPS | SEQ ID NO: 379 | HYSSQSNLADSH | SEQ ID NO: 428 |
| LRPPTALSAALH | SEQ ID NO: 380 | STVLLTD | SEQ ID NO: 429 |
| LRDTHAI | SEQ ID NO: 381 | LTPSSAP | SEQ ID NO: 430 |
| FNMTTFSLARSS | SEQ ID NO: 382 | DMPPWRD | SEQ ID NO: 431 |
| FNPKTPKIAPNI | SEQ ID NO: 383 | HAPFPRLTEISQ | SEQ ID NO: 432 |
| TLPNVLR | SEQ ID NO: 384 | VDLSSVP | SEQ ID NO: 433 |
| SRNIPLPSHFLS | SEQ ID NO: 385 | | |
| SRPGSPV | SEQ ID NO: 386 | | |
| NLNRQPVMKHWP | SEQ ID NO: 387 | | |
| FQTTATRLGFAP | SEQ ID NO: 388 | | |
| LSVSPRMTPFVT | SEQ ID NO: 389 | | |
| KSHTSMEQLNSQ | SEQ ID NO: 390 | | |
| ESFSVTWLPART | SEQ ID NO: 391 | | |
| GQWQADRLRSLP | SEQ ID NO: 392 | | |
| FDVSTVLSSSTH | SEQ ID NO: 393 | | |
| QVDGTNDTRPSR | SEQ ID NO: 394 | | |
| KASNLSPILGLP | SEQ ID NO: 395 | | |

FIG._1E

```
MISQAIGAVA  LGLAVIGGSS  VDARSVAGRS  TDMPSGLTKR  QTQLSPPLAL  YEVPLPIPPL   60
KAPNTVPNPN  TGEDILYYEM  EIRPFSHQIY  PDLEPANMVG  YDGMSPGPTI  IVPRGTESVV  120
RFVNSGENTS  PNSVLHGSF   SRAPFDGWAE  DTTQPGEYKD  YYYPNRQAAR  MLWYHDHAMS  180
ITAENAYMGQ  AGVYMIQDPA  EDALNLPSGY  GEFDIPLVLT  AKRYNADGTL  FSTNGEVSSF  240
WGDVIQVNGQ  PWPMLNVQPR  KYRFRFLNAA  VSRSFALYLA  TSEDSETRLP  FQVIAADGGL  300
LEGPVDTDTL  YISMAERWEV  VIDFSTFAGQ  SIDIRNLPGA  DGLGVEPEFD  NTDKVMRFVV  360
DEVLESPDTS  EVPANLRDVP  FPEGGNWDPA  NPTDDETFTF  GRANGQWTIN  GVTFSDVENR  420
LLRNVPRDTV  EIWRLENNSN  GWTHPVHIHL  VDFRVLSRST  ARGVEPYEAA  GLKDVVWLAR  480
REVVYVEAHY  APFPGVYMLH  CHNLIHEDHD  MMAAFNVTVL  GDYGYNYTEF  IDPMEPLWRP  540
RPFLLGEFEN  GSGDFSELAI  TDRIQEMASF  NPYAQADDDA  AEE                    583
```

The translated amino acid sequence of the Stachybotrys oxidase B gene.

FIG._2

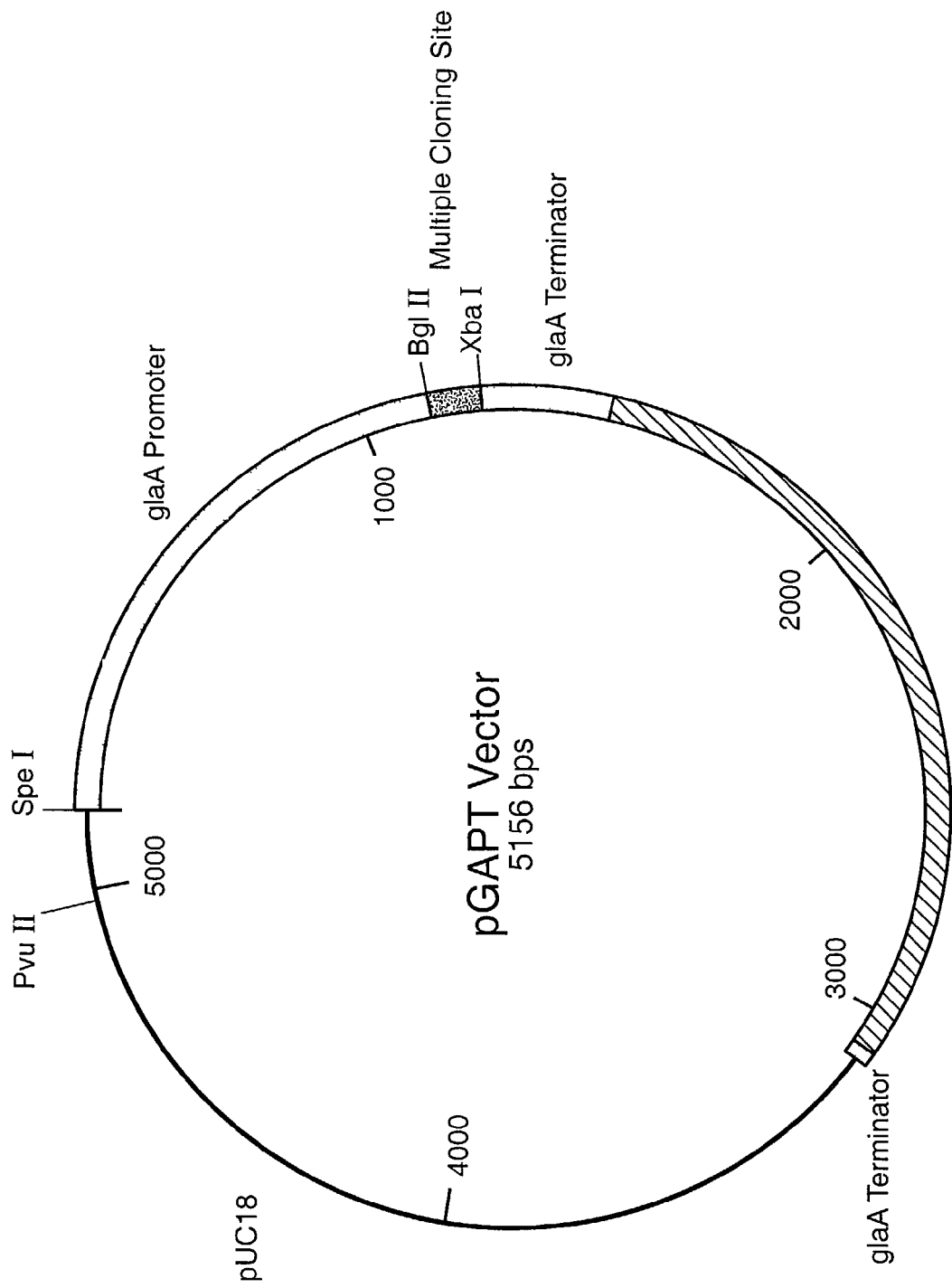
FIG._3

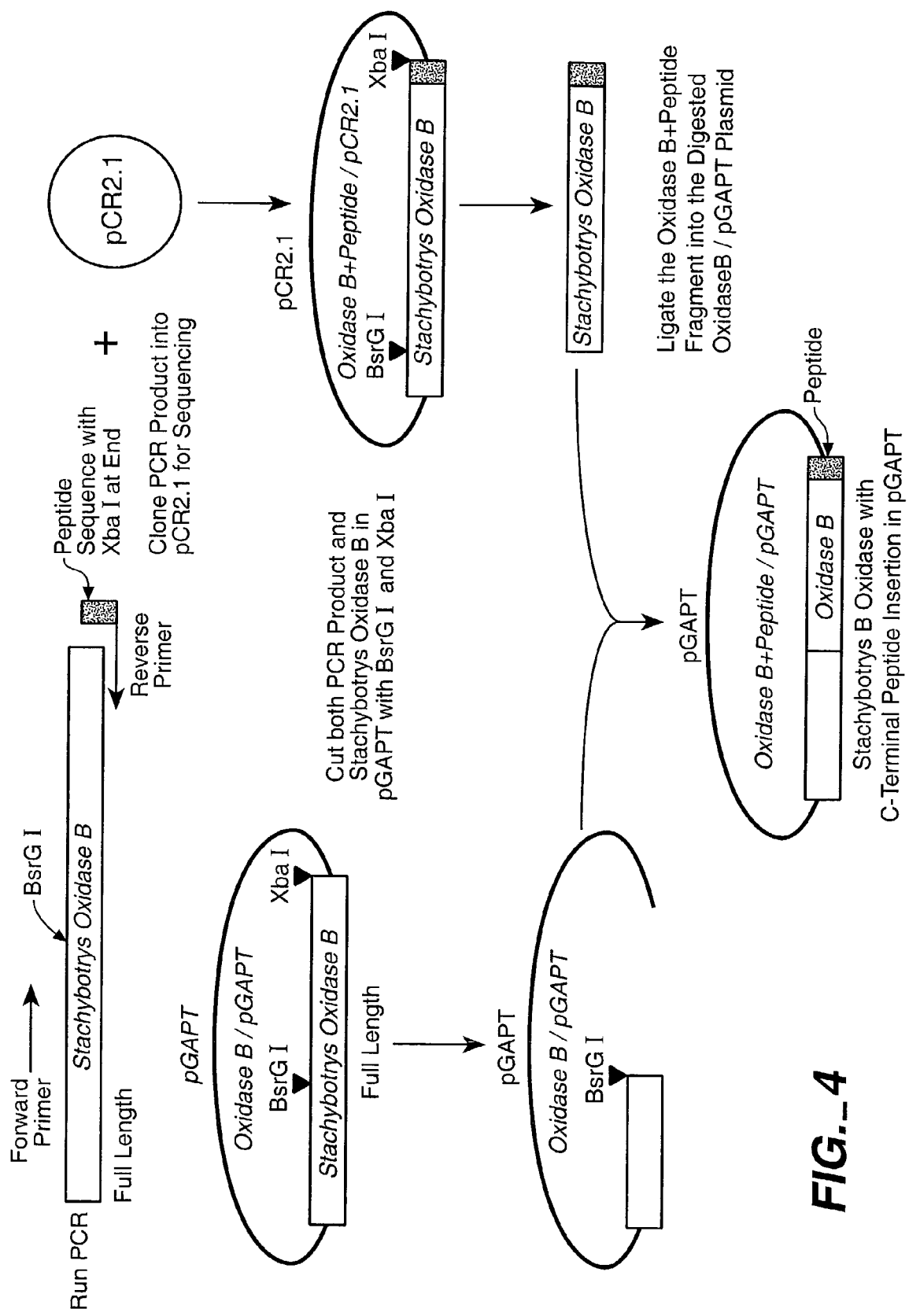
FIG._4

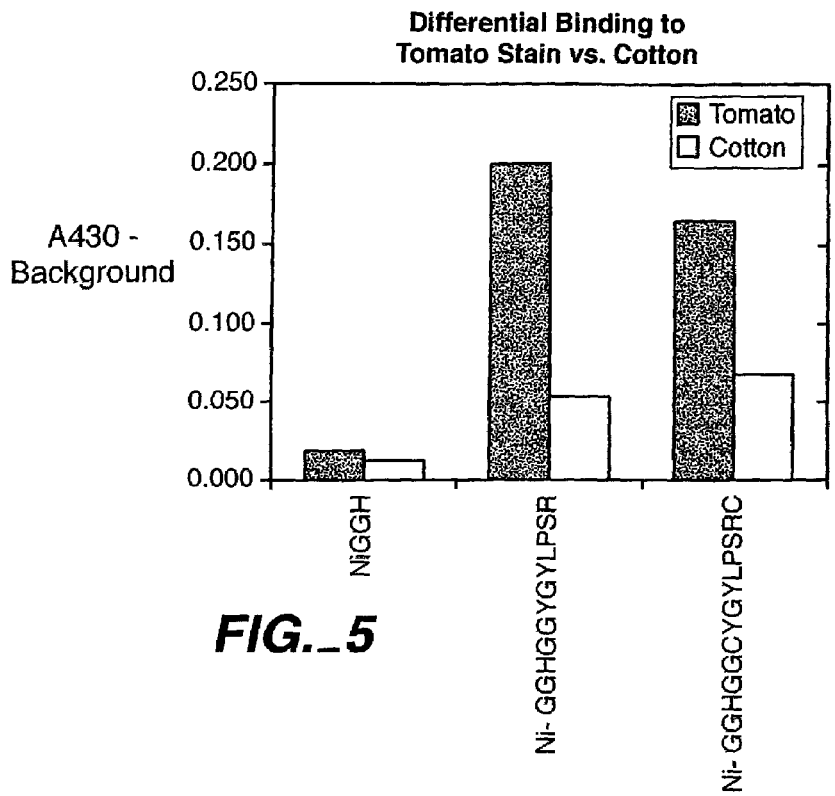
FIG._5
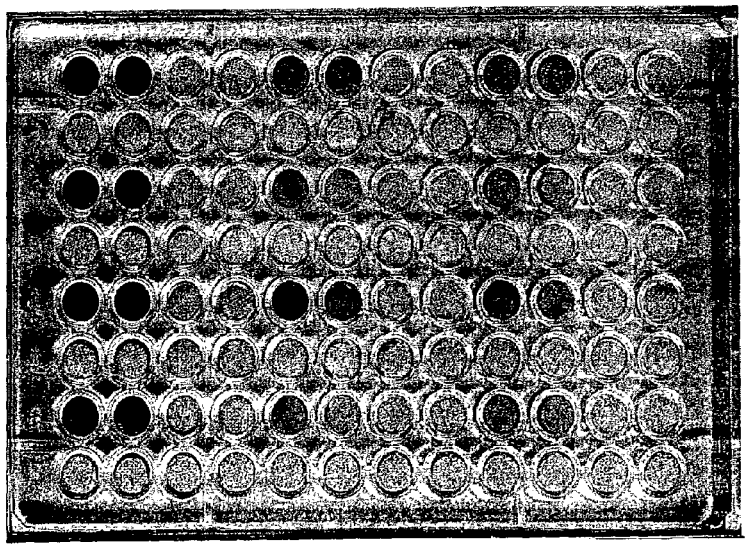
FIG._6

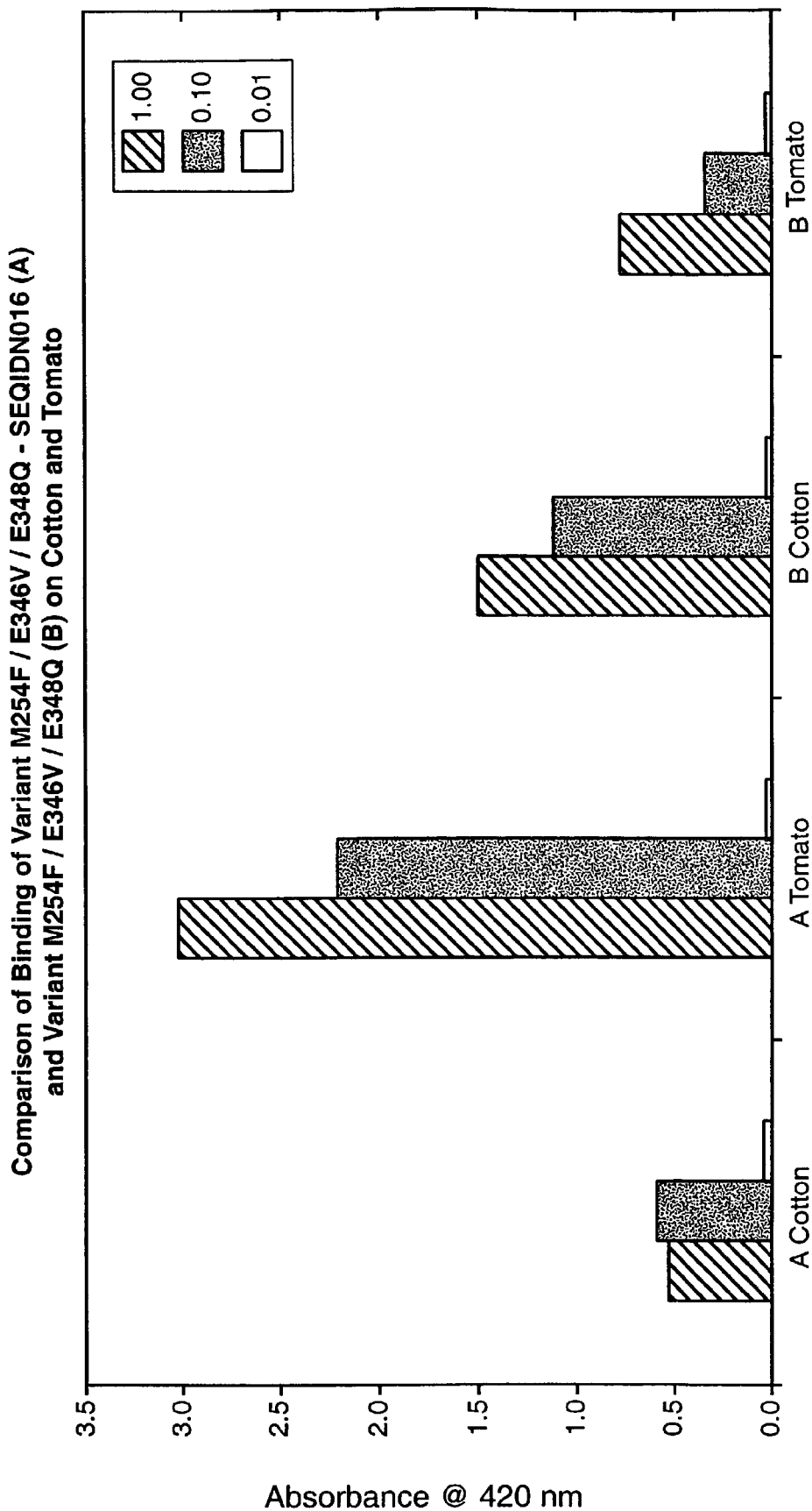
FIG._7

NUCLEIC ACIDS AND EXPRESSION VECTORS COMPRISING CAROTENOID BINDING PEPTIDES

The present application is a Continuation-in-Part of U.S. patent application Ser. No. 09/954,385, filed Sep. 21, 2001, now abandoned.

FIELD OF THE INVENTION

The present invention relates to peptides which bind to a selective target stain and relates to a phenol oxidizing enzyme-peptide complex, which includes the binding peptide conjugated with a phenol-oxidizing enzyme. The phenol oxidizing enzyme-peptide complex may be used in enzymatic compositions, particularly detergent compositions to specifically target stains.

BACKGROUND OF THE INVENTION

Phenol oxidizing enzymes function by catalyzing redox reactions, i.e., the transfer of electrons from an electron donor (usually a phenolic compound) to molecular oxygen (which acts as an electron acceptor) which is reduced to $H_2O$ or $H_2O_2$. While being capable of using a wide variety of different phenolic compounds as electron donors, phenol oxidizing enzymes are very specific for molecular oxygen as the electron acceptor.

Phenol oxidizing enzymes can be utilized for a wide variety of applications, including in the detergent industry, the paper and pulp industry, the textile industry, and the food industry. Phenol oxidizing enzymes are specifically used for their color modifying ability for example for pulp and paper bleaching, for bleaching the color of stains on fabric, and for anti-dye transfer in detergent and textile applications. While the prior art does teach various phenol oxidizing enzymes useful in the above mentioned applications, there remains a need for new and more effective phenol oxidizing enzymes having stain bleaching ability, anti-dye transfer properties, and selective stain removal ability. It is a purpose of the present application to create phenol oxidizing enzyme-peptide complexes with increased binding ability to target stains when compared to the corresponding phenol oxidizing enzyme without the binding peptide. A further purpose of the present invention is to provide a phenol oxidizing enzyme-peptide complex having bleaching ability and particularly to provide a phenol oxidizing enzyme-peptide complex having an ability to remove stains obtained from carotenoid chromophore containing compounds such as those found in tomato and paprika.

SUMMARY OF THE INVENTION

In one aspect the invention pertains to a binding peptide having an amino acid sequence illustrated in any one of SEQ ID NOS: 2 through 433 wherein the peptide binds to a colored substance and particularly to a stain from a carotenoid compound. In one preferred embodiment the binding peptides are the peptides listed in Table 1. In another preferred embodiment the binding peptides are the peptides designated as SEQ ID NOS: 4, 16, 24, 92, 94, 104, 105, 120, 198, 233, 247, 256, 279, 293, 300, 304 and 317. In yet another preferred embodiment the binding peptides further include a cysteine amino acid residue added to each end of the binding peptide.

In a second aspect, the invention pertains to a binding peptide comprising a repeatable motif of 3 to 6 amino acids. In one preferred embodiment, the repeatable motif is selected from the group consisting of SAPA (SEQ ID NO:511), TAPP (SEQ ID NO:528), APAL (SEQ ID NO:452), PPP (SEQ ID NO:547), PPPP (SEQ ID NO:495), SSPH (SEQ ID NO:524), SSP (SEQ ID NO:548), SSK (SEQ ID NO:549), SPT (SEQ ID NO:550), LPAQ (SEQ ID NO:475), PPPL (SEQ ID NO:551), PTPL (SEQ ID NO:506), SPTT (SEQ ID NO:521), PLVP (SEQ ID NO:493), PLP (SEQ ID NO:552), YTKP (SEQ ID NO:546), SLH (SEQ ID NO:553), SLLNA (SEQ ID NO:516), SPL (SEQ ID NO:554), SNLA (SEQ ID NO:517), SPLTQ (SEQ ID NO:519), TTT (SEQ ID NO:555), AARND (SEQ ID NO:448), AARN (SEQ ID NO:447), ARND (SEQ ID NO:453), LSPG (SEQ ID NO:478), NPNN (SEQ ID NO:485), NLAT (SEQ ID NO:556), NTS (SEQ ID NO:557), PHSM (SEQ ID NO:491), PPWM (SEQ ID NO:499), PTSP (SEQ ID NO:507), TGGA (SEQ ID NO:532), YLPS (SEQ ID NO:545), YTKP (SEQ ID NO:546), PGSL (SEQ ID NO:490), APS (SEQ ID NO:558), TPV (SEQ ID NO:559), TTTS (SEQ ID NO:542) and LNAT (SEQ ID NO:483), where the binding peptide has 6 to 15 amino acid residues and binds to a carotenoid compound stain on a fabric.

In a third aspect, the invention pertains to polynucleotides encoding the binding peptides.

In a fourth aspect, the invention pertains to a phenol oxidizing enzyme-peptide complex comprising a phenol oxidizing enzyme and a peptide comprising an amino acid sequence illustrated in any one of SEQ ID NOS: 2 through 433 or a peptide having a repeatable motif as illustrated in Table 2, wherein the complex binds to a colored substance and particularly to a carotenoid compound. In one embodiment the phenol oxidizing enzyme-peptide complex comprises a binding peptide selected from the group consisting of SEQ ID NOS: 4, 16, 24, 92, 94, 104, 105, 120, 198, 233, 247, 256, 279, 293, 300, 304, and 317. In one preferred embodiment the phenol oxidizing enzyme is a laccase and most preferably the laccase is obtainable from a *Stachybotrys* species. In a further preferred embodiment the laccase has the amino acid sequence illustrated in SEQ ID NO: 1. In yet another preferred embodiment the laccase-peptide complex comprises a variant of sequence SEQ ID NO: 1, wherein said variant differs from SEQ ID NO: 1 in at least one of the positions 48, 67, 70, 76, 83, 98, 115, 119, 134, 171, 175, 177, 179, 188, 236, 246, 253, 269, 272, 296, 302, 308, 318, 329, 331, 346, 348, 349, 365, 390, 391, 394, 404, 415, 423, 425, 428, 434, 465, 479, 481, 483, 499, 550, 562, 570, and 573 or sequence positions corresponding thereto and wherein said complex is capable of modifying the color associated with colored compounds. In another preferred embodiment the binding peptide is attached to the C-terminus of the phenol oxidizing enzyme. In yet another embodiment the binding peptide is combined with the phenol oxidizing enzyme in an internal site, preferably by insertion or substitution.

In a fifth aspect, the invention pertains to expression vectors and host cells incorporating the expression vectors comprising a polynucleotide encoding a phenol oxidizing enzyme-peptide complex or a polynucleotide encoding a binding peptide according to the invention. In one preferred embodiment the host cell is a fungal cell.

In a sixth aspect, the invention pertains to a method of enhancing the binding of a laccase enzyme to a target stain and particularly to a carotenoid compound stain. The method includes obtaining a binding peptide of the invention, combining the peptide with a laccase to form a laccase-peptide complex, and exposing a target stain to the laccase-peptide complex under suitable conditions to allow the complex to bind with the target stain.

In a seventh aspect, the invention pertains to detergent and enzyme compositions comprising one or more surfactants and/or additives and the phenol oxidizing enzyme-peptide complex of the invention, wherein said complex selectively binds to a target stain during a wash cycle that includes agitation. In one preferred embodiment the phenol oxidizing enzyme is a laccase. In another preferred embodiment the compositions include one or more enzymes other than laccase.

In an eighth aspect, the invention pertains to a method for producing a host cell comprising a polynucleotide encoding a laccase-peptide complex, comprising (a) obtaining a polynucleotide encoding a laccase having at least 68% identity to the amino acid sequence disclosed in SEQ ID NO: 1; (b) obtaining a polynucleotide encoding a binding peptide having an amino acid sequence as illustrated in any one SEQ ID NOS: 2-433; conjugating the polynucleotide of (a) with (b); introducing said conjugated polynucleotide into a host cell; and growing said host cell under conditions suitable for the production of said laccase-peptide complex.

In a ninth aspect, the invention pertains to a method of using a binding peptide to target a stain on a textile comprising obtaining a binding peptide as illustrated in any one of SEQ ID NOS: 2-433; and exposing said binding peptide to a target stain, wherein said binding peptide binds to said stain and not to said textile.

In a tenth aspect, the invention pertains to a method of enhancing the selectivity of a phenol oxidizing enzyme to a target stain which comprises, derivatizing a laccase with a binding peptide as illustrated in any one of SEQ ID NOS: 2-433 to form a laccase-peptide complex; and exposing the laccase-peptide complex to a target stain, wherein selectivity of the laccase-peptide complex to the target stain is greater than the selectivity of the a non-derivatized laccase having the same amino acid sequence as the laccase of the laccase-peptide complex.

BRIEF DESCRIPTION OF THE DRAWINGS

FIGS. 1A-1E disclose the amino acid sequence of peptides represented by SEQ ID NOS: 2-433 according to the invention. These peptides bind to tomato or paprika stains on cotton using a cyclic 7-mer (FIGS. 1A and 1C), a linear 12-mer (FIGS. 1B and 1D) or mixed population (FIG. 1E) of a phage random peptide library as further discussed in the examples.

FIG. 2 illustrates the amino acid sequence (SEQ ID NO: 1) for the enzyme designated herein as the *Stachybotrys* phenol oxidase B having MUCL accession number 38898. (Also reference is made to U.S. Pat. No. 6,168,936)

FIG. 3 provides an illustration of the vector pGAPT which was used for the expression of *Stachybotrys* phenol oxidase B (SEQ ID NO: 1) and variants thereof in either derivatized form (as a laccase-peptide complex) or in nonderivatized form (the laccase backbone with no binding peptide combination) in *Aspergillus niger*. Base 1 to 1134 contains *Aspergillus niger* glucoamylase gene promoter. Base 1227 to 1485 and 3079 to 3100 contains *Aspergillus niger* glucoamylase terminator. *Aspergillus nidulans* pyrG gene was inserted from 1486 to 3078 as a marker for fungal transformation. The rest of the plasmid contains pUC18 sequence for propagation in *E. coli*. Nucleic acid encoding the *Stachybotrys* phenol oxidase B of SEQ ID NO: 1 was cloned into the BGl II and Xba I restriction sites.

FIG. 4 illustrates the scheme for C-terminus insertion of a binding peptide in *Stachybotrys* phenol oxidase B.

FIG. 5 illustrates the preferential binding of peptide, YGYLPSR (SEQ ID NO: 16) to tomato stained cotton swatches as compared to unsoiled cotton swatches.

FIG. 6 illustrates the oxidation of ABTS by laccase-peptide complexes:
 (a) SEQ ID NO: 1-IERSAPATAPPP (SEQ ID NO: 92);
 (b) SEQ ID NO: 1-KASAPAL (SEQ ID NO: 24);
 (c) SEQ ID NO: 1—C—C derivative of SEQ ID NO: 24; and
 (d) non-derivatized SEQ ID NO: 1.

FIG. 7 illustrates the difference in binding of a derivatized laccase (A) with the corresponding non-derivatized laccase (B) on tomato stained and non-stained cotton swatches. The laccase is provided at a concentration of 1.00 mg/ml, 0.10 mg/ml and 0.01 mg/ml. The derivatized laccase is the M254F/E346V/E348Q variant attached at the C-terminus to YGYLPSR (SEQ ID NO: 16) and the non-derivatized laccase is the M254F/E346V/E348Q variant.

DETAILED DESCRIPTION OF THE INVENTION

General Terms

Unless defined otherwise, all technical and scientific terms used herein have the same meaning as commonly understood by one of ordinary skill in the art to which this invention pertains. For the purpose of the present invention, the following terms are used to describe the invention herein.

The term "peptide" refers to an oligomer in which the monomer units are amino acids (typically, but not limited to L-amino acids) linked by an amide bond. Peptides may be two or more amino acids in length. Peptides that are greater than 100 amino acids in length are generally referred to as polypeptides. However, the terms, peptide, polypeptide and protein may be used interchangeably. Standard abbreviations for amino acids are used herein and reference is made to Singleton et al., (1987) Dictionary of Microbiology and Molecular Biology, 2nd Ed. page 35.

"Percent sequence identity" with respect to peptide or polynucleotide sequences refers to the percentage of residues that are identical in the two sequences. Thus 95% amino acid sequence identity means that 95% of the amino acids in the sequences are identical. Percent identity can be determined by direct comparison of the sequence information provided between two sequences and can be determined by various commercially available computer programs such as BEST-FIT, FASTA, TFASTA and BLAST.

A "binding peptide" according to the invention is a peptide that binds to a target with a binding affinity of at least about $10^{-2}$ M, at least about $10^{-3}$ M, at least about $10^{-4}$ M, at least about $10^{-5}$ M and preferably between about $10^{-2}$ M to $10^{-15}$ M, between about $10^{-2}$ M to $10^{-10}$ M and between about $10^{-2}$ M to $10^{-9}$ M.

The binding affinity of a peptide for its target or the binding affinity of a phenol oxidizing enzyme-peptide complex for its target may be described by the dissociation constant ($K_D$). $K_D$ is defined by $k_{off}/k_{on}$. The $k_{off}$ value defines the rate at which a bound-target complex breaks apart or separates. This term is sometimes referred to in the art as the kinetic stability of the peptide-target complex or the ratio of any other measurable quantity that reflects the ratio of binding affinity such as an enzyme-linked immunosorbent assay (ELISA) signal. $K_{on}$ describes the rate at which the target and the peptide (or the enzyme-peptide complex) combine to form a bound-target complex. In one aspect, the $k_{off}$ value for the bound-target complex will be less that about $10^{-2}$ sec$^{-1}$, less that about $10^{-3}$ sec$^{-1}$, less than about $10^{-4}$ sec$^{-1}$ and also less than about $10^{-5}$ sec$^{-1}$.

Selectivity is defined herein as enhanced binding of a peptide or protein to a target compared to the binding of the peptide or protein to a non-target. Selectivity may also be defined as the enhanced binding of a derivatized phenol oxidizing enzyme (a phenol oxidizing enzyme -binding peptide) to a target compared to the binding of a non-derivatized phenol oxidizing enzyme (a phenol oxidizing enzyme without the binding peptide) to the target. Selectivity may be in the range of about 1.25:1 to 25:1; about 1.5:1 to 15:1; about 1.5:1 to 10:1; and about 1.5:1 to 5:1. Preferably the selectively is at least 4:1, 3:1 or 2:1 for either a) the binding of a peptide to a target compared to the binding of the peptide to a non-target or b) the binding of a derivatized phenol oxidizing enzyme to a target compared to the binding of the nonderivatized phenol oxidizing enzyme to the target.

As used herein a phenol oxidizing enzyme refers to those enzymes which are capable of catalyzing redox reactions wherein the electron donor is usually a phenolic compound and which are specific for molecular oxygen or hydrogen peroxide as the electron acceptor. Examples of such enzymes are laccases (EC1.10.3.2), bilirubin oxidases (EC1.3.3.5), phenol oxidases (EC 1.14.18.1) and catechol oxidases (EC 1.10.3.1). Preferred phenol oxidizing enzymes are laccases. The phenol oxidizing enzymes useful according to the invention may be naturally occurring or recombinant enzymes.

A recombinant phenol oxidizing enzyme is one in which a nucleic acid sequence encoding the enzyme is modified to produce a variant nucleic acid sequence which encodes the substitution, deletion or insertion of one or more amino acids in the naturally occurring amino acid sequence. Phenol oxidizing enzyme variants may include the mature form of the enzyme variant, as well as the pro- and prepro-forms of such variants and post-translational modification such as glycosylation.

A "phenol oxidizing enzyme-peptide complex" means a phenol oxidizing enzyme combined with a binding peptide according to the invention, and is also referred to as a derivatized enzyme. A "laccase-peptide complex" means a laccase enzyme combined with a binding peptide according to the invention. The binding peptide may be combined with the phenol oxidizing enzyme by various means, for example; the binding peptide may be attached to the carbon (C )-terminus or the amino (N)-terminus of the enzyme. The binding peptide may replace an internal sequence of the enzyme or be inserted into an internal sequence of the enzyme or any combination thereof. Additionally, more than one copy of the same or different binding peptide may be combined with the phenol oxidizing enzyme of interest. A non-derivatized phenol oxidizing enzyme is one wherein a binding peptide has not been combined with the phenol oxidizing enzyme.

A preferred target of the binding peptides and phenol oxidizing enzyme-peptide complexes of the invention is a stain. A stain is defined herein as a colored compound which undergoes oxidation by phenol oxidizing enzymes. A coloured compound is a substance that adds colour to a textile or to substances which result in the visual appearances of stains. Targeted classes of coloured substances which may appear as a stain include the following;

a) porphyrin derived structures, such as heme in blood stain or chlorophyll in plants;

b) tannins and polyphenols (see P. Ribéreau-Gayon, Plant Phenolics, Ed. Oliver & Boyd, Edinburgh, 1972, pp. 169-198) which occur in tea stains, wine stains, banana stains, and peach stains;

c) carotenoids and carotenoid derivatives, which are the red, orange and yellow pigments occurring in fruits and vegetables such as tomato, mango, carrots, paprika and leafy green vegetables. Commonly known carotenoids include alpha and beta carotene, lycopene, lutein, zeaxanthin, and cryptoxantin. These compounds include the oxygenated carotenoids, xanthophylls. Reference is made to G. E. Bartley et al., The Plant Cell (1995), Vol. 7, 1027-1038, Biochemical Nomenclature and Related Documents, 2nd Ed. Portland Press (1992), pages 226-238, and Pure Appl. Chem, (1974) 41:407-431). The carotenoids, carotenoid derivatives and oxygenated carotenoids are herein collectively referred to as carotenoids;

d) anthocyanins, the highly coloured molecules which occur in many fruits and flowers (P. Ribéreau-Gayon, Plant Phenolics, Ed. Oliver & Boyd, Edinburgh, 1972, 135-169); and e) Maillard reaction products, the yellow/brown coloured substances which appear upon heating of mixtures of carbohydrate molecules in the presence of protein/peptide structures, such as found in cooking oil.

A coloured compound may also be a dye that is incorporated into a fiber by chemical reaction, adsorption or dispersion. Examples include direct Blue dyes, acid Blue dyes, reactive Blue dyes, and reactive Black dyes.

Particularly preferred targets of the invention include carotenoid stains as defined above. A stain may occur on a fabric or other surface material. Nonlimiting examples of fabric include, cotton, wool, silk, polyester, rayon, linen, nylon and blends thereof. Nonlimiting examples of a surface material include, ceramic, glass, wood and paper.

The phrase "modify the colour associated with a coloured compound" means that the coloured compound is changed through oxidation, either directly or indirectly, such that the colour appears modified i.e. the colour visually appears to be increased, decreased, decoloured, bleached or removed, particularly bleached.

As used herein the term "enhancer" or "mediator" refers to any compound that is able to modify the colour associated with a coloured compound in association with a phenol oxidizing enzyme or a compound which increases the oxidative activity of the phenol oxidizing enzyme. The enhancing agent is typically an organic compound.

As used herein, *Stachybotrys* refers to any *Stachybotrys* species which produces a phenol oxidizing enzyme and particularly a laccase enzyme capable of modifying the colour associated with coloured compounds. The present invention encompasses derivatives of natural isolates of *Stachybotrys* including progeny, mutants or variants as long as the derivative is able to produce a phenol oxidizing enzyme, and particularly a laccase, capable of modifying the colour associated with coloured compounds.

As used in the specification and claims, the singular "a", "an" and "the" include the plural references unless the context clearly dictates otherwise. For example, the term a vector may include a plurality of vectors.

The following references describe the general techniques employed herein: Sambrook et al (1989) *Molecular Cloning: A Laboratory Manual,* Cold Spring Harbour Laboratory Press, Cold Spring Harbour, N.Y.; and Ausubel et al. (1987) *Current Protocols in Molecular Biology,* Greene-Publishing & Wiley Interscience N.Y. (Supplemented through 1999).

The contents of all references, patents and published patent applications cited throughout this application are hereby incorporated by reference in their entirety.

B. Binding Peptides

The binding peptides of the invention may be obtained using methods well known in the art. Preferably the binding peptides are identified by using random peptide libraries which are screened using techniques including phage display, biopanning and acid elution. These techniques are described in various references such as, Scott and Smith (1990) Science 249:386; Smith and Scott (1993) Methods Enzymol. 217: 228; Cwirla et al., (1990) Proc. Natl. Acad. Sci. USA 87:6378; Parmley et al., (1988) Gene 73:305; Balass et al., (1996) Anal. Biochem., 243:264 and Huls et al., (1996) Nature Biotechnol., 7:276).

While a random peptide library is a preferred library used to identify binding peptides according to the invention, the binding peptides useful in the invention are not limited to identification using a random peptide library. Binding peptides of the invention may be identified from use of synthetic peptide libraries, peptide loop libraries, antibody libraries and protein libraries. Those skilled in the art are aware of commercially available libraries from sources such as New England BioLabs and Dyax Corporation.

Display methods that may be used to screen for binding peptides include phage display, yeast display and ribosome display. Once the peptide library is screened, the peptides that bind to a specific target may be identified by various means well-known in the art including, acid elution, polymerase chain reaction (PCR), sequencing, and other well-known methods.

Preferably the binding peptides of the invention are between 4 and 50 amino acids in length, also between 4-25 amino acids in length, between 4-20 amino acids in length and between 6-15 amino acids in length.

The binding peptides according to the invention include the peptides listed in FIG. 1A-E (SEQ ID NOS: 2-433). These peptides bind to carotenoid compounds and particularly to carotenoid stains on a textile obtained from tomato and paprika. In one embodiment, preferred binding peptides are listed in Table 1.

TABLE 1

| | |
|---|---|
| SLLNATK | SEQ ID NO: 4 |
| YGYLPSR | SEQ ID NO: 16 |
| KASAPAL | SEQ ID NO: 24 |
| IERSAPATAPPP | SEQ ID NO: 92 |
| HVQILQLAAPAL | SEQ ID NO: 94 |
| YHTPSTGGASPV | SEQ ID NO: 104 |
| SSDVPQAARNDA | SEQ ID NO: 105 |
| QIWHPHNYPGSL | SEQ ID NO: 120 |
| TTAPPTT | SEQ ID NO: 198 |
| STPGSLQ | SEQ ID NO: 233 |
| PSMLNAT | SEQ ID NO: 247 |
| RLSDPMH | SEQ ID NO: 256 |
| QTTNSNMAPALS | SEQ ID NO: 279 |
| LPAQYQTIPGSL | SEQ ID NO: 293 |
| AARNDQVSHMHM | SEQ ID NO: 300 |
| DLFSAHHTGGAL | SEQ ID NO: 304 |
| YLPSTFAPPLPL | SEQ ID NO: 317 |

Particularly preferred binding peptides are SEQ ID NOS: 4, 16, 24, 92, 256 and 317.

In a further embodiment, the binding peptides according to the invention may include cysteine residues on each end of the peptide. These binding peptides are more specifically referred to herein as binding peptide C—C derivatives. For example, the binding peptide PSMLNAT may also exist in the form CPSMLNATC and is considered a binding peptide according to the invention. When a binding peptide according to the invention is used as an internal replacement or insert for internal loops or turns in the phenol oxidizing enzyme, the binding peptide may be used in the C—C derivative form or non C—C derivative form. While any of the peptides listed in FIGS. 1A-1E may include the C—C derivatized form, particularly preferred are the peptides listed in FIG. 1A and FIG. 1C.

Additionally, a linker molecule (also sometimes referred to as a spacer moiety in the prior art) may be added to either end of a binding peptide (L-P or P-L). The linker molecule may enhance the binding of the peptide to its target. A linker molecule may be for example, a short peptide, such as the amino acid triad GGH or GGHGG, a carbon chain, such as $(CH_2)_n$ wherein n equals 1 to 10, a polymer, such as PEG $(CH_2-O)_n$ wherein n equals 2-20, a sugar, a lipid or the like. In one embodiment the linker is GGH or GGHGG. In another embodiment the linker is attached to Ni-GGH or Ni-GGHGG.

The linker molecule may be attached to the binding peptide alone or the linker molecule may be part of the enzyme-peptide complex. For example when the linker is placed between the binding peptide and the enzyme (E-L-P) or when the linker is attached to the peptide at the non-enzyme complexed end (E-P-L).

Non-limiting specific examples of the linker attached to the binding peptide alone include:
a) Ni-GGH-[SLLNATK, (SEQ ID NO: 4)];
b) Ni-GGH-[YGYLPSR, (SEQ ID NO: 16)];
c) Ni-GGH-[KASAPAL, (SEQ ID NO: 24)];
d) Ni-GGHGG-[RLSDPMH, (SEQ ID NO: 256)];
e) Ni-GGHGG-[YGYLPRS, (SEQ ID NO: 16)]; and the like.

Non-limiting specific examples of the linker attached to the enzyme-binding peptide complex wherein the linker is attached to the C-terminus of the enzyme include:
a) SEQ ID NO: 1—Ni-GGH-[SLLNATK, (SEQ ID NO: 4)];
b) the 254 variant SEQ ID NO: 1—Ni-GGH-[KASAPAL, (SEQ ID NO: 24)];
c) the 254/346/348 variant of SEQ ID NO: 1—Ni-GGHGG-[SLLNATK, (SEQ ID NO: 4)];
d) the 254/346/348 variant of SEQ ID NO: 1—Ni-GGHGG-[IERSAPATAPPP, (SEQ ID NO: 92)] and the like.

The linker molecules may be attached to any of the binding peptides represented as SEQ ID NOS: 2-433.

The invention further includes binding peptides having at least 60% but less than 100% amino acid sequence identity to the binding peptides listed in FIG. 1. For example at least 65%, at least 70%, at least 75%, at least 80%, at least 85%, at least 90%, at least 93%, at least 95%, at least 97%, at least 99% amino acid sequence identity. A peptide having at least 60% sequence identity to a binding peptide listed in FIG. 1 will also have a binding affinity for the same target in the range of $10^{-2}$M to $10^{-15}$M, generally at least about $10^{-2}$M, at least about $10^{-3}$M, at least about $10^{-4}$M and at least about $10^{-5}$M.

Repeatable motifs (also referred to herein as consensus sequences) have been observed in a number of the binding peptides listed in FIG. 1. Repeatable motifs include at least three amino acid residues and may include four, five or six amino acid residues in common with the binding peptide listed in FIG. 1.

Repeatable motifs of the binding peptides include the following amino acid residues as listed in Table 2. Also included in Table 2 are sequence identifiers for representative binding peptides of FIG. 1 which include said repeatable motif.

TABLE 2

| CONSENSUS SEQUENCE | Binding Peptide SEQ ID NO: | CONSENSUS SEQUENCE | Binding Peptide SEQ ID NO: |
|---|---|---|---|
| AARND | 105, 300 | PPWM | 208, 249 |
| APAL | 24, 94, 279 | SAPA | 24, 92 |
| AARN | 105, 300 | LNAT | 4, 247 |
| ARND | 105, 300 | LSPG | 103, 240 |
| SPL | 132, 289, 326, 372, 375, 425 | PPPP | 127, 153, 156, 179, 186 |
| LTQ | 179, 289, 327, 425 | PAR | 141, 290, 374, 391 |
| NTSI | 14, 124 | TAPP | 92, 198 |
| PTSP | 95, 242 | TGGA | 104, 304 |
| PSST | 56, 227 | NPNN | 204, 223 |
| SLLNA | 4, 77 | PGN(C) | 48, 240 |
| SSP | 38, 190, 326, 375, 399, 419 | PLP | 164, 310, 317, 332, 385 |
| SPLTQ | 289, 425 | PLVP | 112, 186, 332 |
| TATHL | 103, 142 | PPPF | 179, 197 |
| NTS | 14, 18, 41, 124 | PQSP | 292, 412 |
| SPT | 49, 118, 245, 410 | PSAT | 158, 232 |
| LPAQ | 163, 293, 365 | PART | 374, 391 |
| PGSL | 120, 233, 293 | PPSSP | 190, 419 |
| PHSM | 221, 315, 330 | YTKP | 145, 303, 427 |
| PLTQ | 289, 327 | ALH(C) | 234, 263 |
| PPPL | 136, 295, 369 | ALSA | 310, 380 |
| YLPS | 16, 317 | (C)APS | 20, 72, 211, 259 |
| PSTH | 127, 333 | (C)ISD | 12, 44 |
| PTPL | 112, 353, 417 | (C)KAS | 24, 66 |
| PTTT | 93, 422 | (C)KLN | 27, 207 |
| QLQL | 108, 143 | (C)KPT | 22, 217 |
| RLAQ | 110, 334 | (C)LQS | 30, 193, 275 |
| (C)TTT | 93, 215, 246, 254, 328 | (C)SLH | 2, 32, 98, 196, 301, 314 |
| SIMN | 297, 344 | (C)SSK | 15, 31, 100, 150 |
| SNLA | 237, 428 | SAQN | 119, 152 |
| SPTT | 118, 410 | HSML | 42, 315 |
| SPV(C) | 3, 292 | IPST | 108, 333 |
| SSVP | 294, 433 | KAPS | 176, 211 |
| TFAP | 161, 317 | LNAN | 27, 174 |
| TFPL | 185, 281 | LPLK | 231, 375 |
| LPQR | 49, 100 | TIPG | 293, 328 |
| LSSS | 286, 392 | TPV(C) | 163, 214, 294 |
| LVPL | 185, 291 | TSHT | 316 |
| NLAT | 242, 339 | TSLL | 77, 246 |
| NPTS | 57, 94 | TSLM | 232, 357 |
| VASA | 310, 329 | TSPP | 242, 326 |
| NFSN | 176, 372 | ESFS | 372, 391 |
| AITA | 133, 141 | DVST | 393, 402 |
| PPSL | 148, 182 | IPLP | 332, 385 |
| NFSN | 176, 372 | PSLP | 149, 399 |
| NPKT | 235, 382 | SFTK | 75, 259 |
| PPRA | 341, 359 | SGLA | 320, 331 |
| SSPH | 37, 398, 418 | SSPL | 326, 375 |
| THPL | 38, 358 | TQPP | 179, 347 |
| TPSS | 338, 429 | SPPW | 326, 329 |
| PRLT | 364, 431 | SRSP | 166, 177 |
| KHPP | 340, 418 | MHTT | 169, 227 |
| STVL | 392, 428 | TTTT | 246, 422 |
| GLAS | 50, 330 | SNLSP | 123, 395 |

Preferred repeatable motifs include SAPA, TAPP, APAL, PPP, PPPP, SSPH, SSP, SSK, SPT, LPAQ, PPPL, PTPL, SPTT, PLVP, PLP, YTKP, SLH, SLLNA, SPL, SNLA, SPLTQ, TTT, AARND, AARN, ARND, LSPG, NPNN, NLAT, NTS, PHSM, PPWM, PTSP, TGGA, YLPS, YTKP, PGSL, APS, TPV, TTTS and LNAT. In one embodiment preferred repeatable motifs include SAPA, TAPP, APAL, PPPP, SSPH, LPAQ, PPPL, PTPL, SPTT, PLVP, YTKP, SNLA, AARN, ARND, LSPG, NPNN, NLAT, PHSM, PPWM, PTSP, TGGA, YLPS, YTKP, PGSL, TTTS and LNAT. In another embodiment preferred repeatable motifs are SAPA, TAPP, APAL, PHSM, YLPS, AARND, ARND, SLLNA, PPPP, SNLA and NLAT.

The repeatable motif may also include a cysteine residue at the beginning and/or end of the motif, for example SPV (SPVC); TPV (TPVC); SLH (CSLH); LQS (CLQS) and KAS (CKAS). Particularly preferred are (C)SLH, (C)TTT, (C)SSK, (C)LQS, and TPV(C).

In general, the repeatable motifs may occur alone in a binding peptide, as multiple motifs in the same binding peptide, in sequential order, or overlapping one another. For example the binding peptide HVQILQLA<u>APAL</u> (SEQ ID NO: 94) includes the repeatable motif APAL. The binding peptide YG<u>YLPS</u>R (SEQ ID NO: 16) includes the repeatable motif YLPS. The binding peptides SL<u>LNAT</u>K (SEQ ID NO: 3) and PSM<u>LNAT</u> (SEQ ID NO: 247) include the repeatable motif LNAT. The binding peptide T<u>TAPP</u>TT (SEQ ID NO: 198) includes the repeatable motif TAPP. The binding peptides INT<u>PHSM</u> (SEQ ID NO: 221), S<u>PHSM</u>LQNPSGP (SEQ ID NO: 315) and VASAN<u>PHSM</u>TSW (SEQ ID NO: 330) include the repeatable motif PHSM. The binding peptides <u>VASANPHSM</u>TSW (SEQ ID NO: 330), <u>ESFS</u>VTWL<u>PART</u> (SEQ ID NO: 391), and <u>LPAQ</u>YQTI<u>PGSL</u> (SEQ ID NO: 297) include multiple motifs, two repeatable motifs, in the same sequence. The binding peptide IER<u>SAPATAPP</u>P (SEQ ID NO: 92) includes two repeatable motifs (SAPA and TAPP) in sequential order. The binding peptide KA<u>SAPAL</u> (SEQ ID NO: 24) includes two overlapping repeatable motifs (SAPA and APAL).

Peptides other than the peptides illustrated in FIG. 1, which have a repeatable motif as illustrated in Table 2, are referred to herein as homologous motif binding peptides. Homologous motif binding peptides will include 6-25 amino acid residues and preferably will include 6-15 amino acid residues. Further the homologous motif binding peptides will bind to a target with a binding affinity similar or greater to the binding affinity of the binding peptides of FIG. 1 having the same repeatable motif. Preferably the target will be a stain, preferably a carotenoid stain and the binding affinity will be at least about $10^{-2}$M, about $10^{-3}$M, about $10^{-4}$M, about $10^{-6}$M and generally between about $10^{-2}$M and $10^{-9}$M. A homologous motif binding peptide will include not only a repeatable motif as defined herein, but will have between 20% and 95% amino acid sequence identity with a sequence illustrated in FIG. 1 having the same repeatable motif, that is at least 25% sequence identity, at least 30% sequence identity, at least 40% sequence, at least 50% sequence identity, at least 60% sequence identity, at least 70% sequence identity, at least 80% sequence identity, at least 90% sequence identity or at least 95% sequence identity to a binding peptide illustrated in FIG. 1 which includes the same repeatable motif. Preferably if the homologous motif binding peptide is a 7 amino acid residue peptide, the homologous motif binding peptide will have at least 30% sequence identity with a binding peptide illustrated in FIG. 1 having the same repeatable motif when the peptides are aligned with no gaps. If the homologous motif binding peptide is a 12 amino acid residue peptide, the peptide will have at least 25% sequence identity with a binding peptide illustrated in FIGS. 1A-1E having the same repeatable motif when the peptides are aligned with no gaps.

In one embodiment, the binding peptides having identical repeatable motifs will bind to stains with structurally and/or biochemically related chromophores with about the same binding affinity. Preferably in one aspect, the homologous motif binding peptides including one or more repeatable motifs will bind to the carotenoids, such as lycopene and beta-carotene. In another aspect, the homologous motif binding peptides having one or more identical repeatable motifs will bind to the carotenoids such as the xanthophylls and particularly to casporubins and capsoxanthins.

Additionally binding peptides of the invention may include peptides having sequence clusters. A sequence cluster is defined herein as including a repeatable motif followed by 1 or 2 identical amino acid residues, wherein the repeatable motif and the identical amino acid residues are separated by 1 to 10, preferably 1 to 3 amino acids residues. Numerous examples of sequence clusters may be found in FIG. 1. Two such examples are SEQ ID NOS: 103 and 142 wherein the repeatable motif TATHL is separated from the amino acid residue P by one amino acid residue and SEQ ID NOS: 93 and 422 wherein the repeatable motif PTTT is separated from the amino acid residue T by three amino acid residues.

The binding peptides according to the invention may be made by various well known techniques in the art and include recombinant genetic engineering, chemical synthesis, PCR, and amplification.

C. Polynucleotides Encoding the Binding Peptides

The present invention encompasses polynucleotides which encode binding peptides according to the invention. Specifically polynucleotides include nucleic acid sequences encoding peptides illustrated in FIG. 1 (SEQ ID NOS: 2-433) and their C—C derivatives. Particularly preferred polynucleotides encode the binding peptides illustrated in Table 1 and their C—C derivatives. Additionally, polynucleotides which encode homologous motif binding peptides having identical repeatable motifs as those listed in Table 2 are part of the invention. As will be understood by the skilled artisan, due to the degeneracy of the genetic code, a variety of polynucleotides can encode a binding peptide of the invention such as those disclosed in FIG. 1, the C—C derivatives or a homologous motif binding peptide including a repeatable motif as illustrated in Table 2. The present invention encompasses all such polynucleotides.

A polynucleotide which encodes a binding peptide of the invention may be obtained by standard procedures known in the art, for example, by chemical synthesis, by PCR and by direct isolation and amplification.

D. Phenol Oxidizing Enzymes

In one embodiment the phenol oxidizing enzyme of the invention is a fungal phenol oxidizing enzyme. Phenol oxidizing enzymes are known to be produced by a wide variety of fungi and include but are not limited to species of the genii *Aspergillus, Neurospora, Podospora, Botrytis, Pleurotus, Fomes, Coprinus, Phlebia, Trametes, Polyporus, Rhizoctonia, Bipolaris, Curvularia, Amerosporium, Lentinus, Myrothecium, Chaetomium, Humicola, Trichoderma, Myceliophthora, Scytalidium* and *Stachybotrys*.

Preferred phenol oxidizing enzymes and particularly laccases are derived from *Stachybotrys* including *S. chartarum, S. parvispora, S. kampalensis, S. theobromae, S. bisbyi, S. cylindrospora, S. dichroa, S. oenanthes* and *S. nilagerica; Myceliophthora* including *M. thermophilum; Coprinus* including *C. cinereus; Polyporus* including *P. pinsitus; Rhizoctonia* including *R. solani; Bipolaris* including *B. spicifera; Curvularia* including *C. pallescens; Amerosporium* including *A. atrum;* and *Scytalidium* including *S. thermophilum*.

Many of the phenol oxidizing enzymes useful according to the invention may be obtained or produced from phenol oxidizing producing microorganisms in publicly available databases such as Belgian Coordinated Collections of Microorganisms, Mycothàque de l'Università Catholiquede Louvain (MUCL). Illustrative is *Stachybotrys* strains (such as *S. parvispora* having accession number MUCL 38996, *S. chartarum* having accession number MUCL 38898, and *S. chartarum* having accession number MUCL 30782). These microorganisms may be grown under aerobic conditions in nutrient medium containing assimilable carbon and nitrogen together with other essential nutrients. The medium can be composed in accordance with principles well-known in the art.

During cultivation, the phenol oxidizing enzyme producing strains secrete the enzyme extracellularly. This permits the isolation and purification (recovery) of the enzyme to be achieved by, for example, separation of cell mass from a culture broth (e.g. by filtration or centrifugation). The resulting cell-free culture broth can be used as such or, if desired, may first be concentrated (e.g. ultrafiltration). If desired, the phenol oxidizing enzyme can then be separated from the cell-free broth and purified to the desired degree by conventional methods, e.g. by column chromatography.

The phenol oxidizing enzymes according to the present invention may be isolated and purified from the culture broth into which they are extracellularly secreted by concentration of the supernatant of the host culture, followed by hydrophobic interaction chromatography or anion exchange chromatography.

Numerous references are available on suitable phenol oxidizing enzymes which may be combined or derivatized with the binding peptides of the invention, and reference is made to WO 98/38286; WO 99/49020; WO 00/37654; WO 01/21809; and U.S. Pat. No. 6,168,936;

The phenol oxidizing enzyme comprising the enzyme-peptide complex may be a recombinant enzyme of a naturally occurring phenol oxidizing enzyme and methods for introducing mutations into phenol oxidizing enzymes encoding DNA sequences are known and reference is made to U.S. Pat. No. 4,760,025; U.S. Pat. No. 5,770,419; U.S. Pat. No. 5,985,818; U.S. Pat. No. 6,060,442; WO 98/27197 and WO 98/27198.

In an illustrative embodiment, a laccase enzyme which may be combined with a binding peptide to form a phenol oxidizing enzyme-peptide complex according to the invention is obtainable from any *Stachybotrys* species which produces a laccase capable of modifying the color associated with colored compounds. A preferred phenol oxidizing enzyme is *Stachybotrys* oxidase B having the amino acid sequence shown in SEQ ID NO: 1 and enzymatically active variants thereof. Typical variant enzymes in accordance with the invention will have at least 60% and less than 100% sequence identity to the amino acid sequence of SEQ ID NO: 1. That is at least 60% and less than 100%; at least 65% and less than 100%; at least 70% and less than 100%; at least 75% and less than 100%; at least 80% and less than 100%; at least 85% and less than 100%; at least 90% and less than 100%; at least 95% and less than 100%; and at least 97% and less than 100% sequence identity to the amino acid sequence disclosed in SEQ ID NO: 1.

The present invention encompasses laccase variants where the variant comprises a sequence that differs from that of SEQ ID NO: 1 in at least one of the following positions: 48, 67, 70, 76, 83, 98, 115, 119, 134, 171, 175, 177, 179, 188, 236, 246, 253, 254, 269, 272, 296, 302, 308, 318, 329, 331, 346, 348, 349, 365, 390, 391, 394, 404, 415, 423, 425, 428, 434, 465, 479, 481, 483, 499, 550, 562, 570, and 573 or sequence positions corresponding thereto. These amino acid position numbers refer to those assigned to the *Stachybotrys* oxidase B enzyme sequence presented in SEQ ID NO: 1.

Preferred variants include a sequence that differs from that of SEQ ID NO: 1 in at least one of the following positions 188, 254, 272, 346, 348, 394, and 425. One such variant includes an amino acid substitution in position 254 (the 254 variant) substituted with F, N, L, K, A, I, E, S, H, V, T, P, G or C, preferably F. In a further embodiment, the 254 variant is combined with at least one further substitution selected from the group consisting of positions 48, 67, 70, 76, 83, 98, 115, 119, 134, 171, 175, 177, 179, 188, 236, 246, 253, 269, 272, 296, 302, 308, 318, 329, 331, 346, 348, 349, 365, 390, 391, 394, 404, 415, 423, 425, 428, 434, 465, 479, 481, 483, 499, 550, 562, 570, and 573. Preferably the additional substituted positions are selected from 76, 188, 272, 302, 346, 348, 394 and 425. Further preferred variants include the following amino acid substitution sets:

(a) 76/188/254/302, (76/188/254/302 variant);

(b) 76/254/302, (76/254/302 variant);

(c) 254/394, (254/394 variant);

(d) 254/346/348, (254/346/348 variant) and specifically 254F/E346V/E348Q, (M254F/E346V/E348Q variant);

(e) 188/254/346/348/394, (88/254/346/348/394 variant); and (f) 171/179/188/254/346/348/394, (171/179/188/254/346/348/394 variant).

Still other preferred variants of SEQ ID NO: 1 include the substitution of amino acid residues at positions 394/425, (394/425 variant) specifically D394N/V425M. The 394/425 variant may further include an amino acid substitution in at least one of the positions 76, 254 and 302.

Yet another preferred variant of SEQ ID NO: 1 includes an amino acid substitution in position 272, (272 variant), and additionally a substitution of amino acid position 272 combined with a substitution at position 254, specifically M254F/S272L.

Polynucleotides encoding a phenol oxidizing enzyme and specifically a laccase, may be obtained by standard procedures known in the art for example, by cloned DNA (e.g. a DNA "library"), by chemical synthesis, by cDNA cloning, by PCR or by the cloning of genomic DNA or fragments thereof, purified from a desired cell, such as a *Stachybotrys* species. Nucleic acid sequences derived from genomic DNA may contain regulatory regions in addition to coding regions. These methods are well known and reference is made to Sambrook et al., 1989, Molecular cloning, A Laboratory Manual, 2d Ed. Cold Spring Harbor Laboratory Press, Cold Spring Harbor, N.Y.; Benton and Davies, 1977, Science 196: 180; Grunstein and Hogness 1975, Proc. Natl. Acad. Sci. USA 72:3961; and U.S. Pat. Nos. 4,683,202 and 6,168,936. In one embodiment, preferred polynucleotides encode the laccase as illustrated in SEQ ID NO: 1.

E. Making the Phenol Oxidizing Enzyme-Peptide Complex

The phenol oxidizing enzyme-peptide complex (also referred to as the derivatized phenol oxidizing enzyme) may be constructed by methods well known in the art including use of PCR. A binding peptide according to the invention may a) be inserted into a phenol oxidizing enzyme, b) replace an internal loop or turn, c) be attached to the carbon or nitrogen terminus of the enzyme or d) include a combination of the above. For example, a combination of formats can include a binding peptide combined with a phenol oxidizing enzyme at the C terminus end of the phenol oxidizing enzyme and a binding peptide inserted into an internal loop of the enzyme wherein the binding peptide is the same or different at each location. More specifically, as a non-limiting example, the binding peptide SEQ ID NO: 16 may be attached to the C-terminus of a laccase having SEQ ID NO: 1 and may also be inserted into an internal loop of the laccase enzyme. In a preferred embodiment the binding peptide is attached to the carbon terminus.

F. Expression Systems

The present invention provides host cells, expression methods and systems for the production of the phenol oxidizing enzyme-peptide complex in host microorganisms, such as fungus, yeast and bacteria.

Molecular biology techniques are disclosed in Sambrook et al., Molecular Biology Cloning: A Laboratory Manual, Second Edition (1989) Cold Spring Harbor Laboratory Press, Cold Spring Harbor, N.Y. (1989). A polynucleotide encoding a phenol oxidizing enzyme-peptide complex is obtained and transformed into a host cell using appropriate vectors. A variety of vectors and transformation and expression cassettes suitable for the cloning, transformation and expression in fungus, yeast, plants and bacteria are known by those of skill in the art.

Typically, the vector or cassette contains sequences directing transcription and translation of the phenol oxidizing enzyme-peptide complex, a selectable marker, and sequences allowing autonomous replication or chromosomal integration. Suitable vectors comprise a region 5' of the gene which harbors transcriptional initiation controls and a region 3' of the DNA fragment which controls transcriptional termination. These control regions may be derived from genes homologous or heterologous to the host as long as the control region selected is able to function in the host cell.

Initiation control regions or promoters, which are useful to drive expression of the phenol oxidizing enzymes in a host cell are known to those skilled in the art. Virtually any promoter capable of driving these phenol oxidizing enzymes is suitable for the present invention. Nucleic acid encoding the phenol oxidizing enzyme is linked operably through initiation codons to selected expression control regions for effective expression of the oxidative or reducing enzymes. Once suitable cassettes are constructed they are used to transform the host cell.

Suitable hosts include fungus, yeast, plants and bacteria. In one embodiment the host cell is a filamentous fungus including a *Aspergillus* species, a *Trichoderma* species and a *Mucor* species. In a further embodiment, the fungus includes *Trichoderma reesei, Aspergillus niger* and *Aspergillus oryzae*. In yet another embodiment, the host cell is a yeast which includes *Saccharomyces, Pichia, Hansenula, Schizosaccharomyces, Kluyveromyces* and *Yarrowia* species. In yet another embodiment the host cell is a gram positive bacteria such as a *Bacillus* species or a gram negative bacteria such as a *Escherichia* species General transformation procedures are taught in Current Protocols In Molecular Biology (vol. 1, edited by Ausubel et al., John Wiley & Sons, Inc. 1987, Chapter 9) and include calcium phosphate methods, transformation using PEG and electroporation. For *Aspergillus* and *Trichoderma,* PEG and Calcium mediated protoplast transformation can be used (Finkelstein, DB 1992 Transformation. In Biotechnology of Filamentous Fungi. Technology and Products (eds. by Finkelstein & Bill) 113-156. Electroporation of protoplast is disclosed in Finkelestein, DB 1992 Transformation. In Biotechnology of Filamentous Fungi. Technology and Products (eds. by Finkelstein & Bill) 113-156. Microprojection bombardment on conidia is described in Fungaro et al. (1995) Transformation of *Aspergillus nidulans* by microprojection bombardment on intact conidia. FEMS Microbiology Letters 125 293-298. *Agrobacterium* mediated transformation is disclosed in Groot et al. (1998) *Agrobacterium tumefaciens*-mediated transformation of filamentous fungi. Nature Biotechnology 16 839-842. For transformation of *Saccharomyces,* lithium acetate mediated transformation and PEG and calcium mediated protoplast transformation as well as electroporation techniques are known by those of skill in the art.

As discussed above for the production of phenol oxidizing enzymes, the phenol oxidizing enzyme-peptide complex may be produced by cultivation of a host cell which includes a polynucleotide encoding the phenol oxidizing-peptide complex under aerobic conditions in nutrient media containing assimilable carbon and nitrogen together with other essential nutrient. These conditions are well known in the art.

Host cells that contain the coding sequence for a phenol oxidizing enzyme-peptide complex of the present invention and express the phenol oxidizing enzyme may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

Once a phenol oxidizing enzyme-peptide complex is encoded the derivatized enzyme may be isolated and purified from the host cell by well-known techniques such as, cell separation and concentration of the cell free broth by ultrafiltration, ammonium sulfate fractionation, purification by gel filtration, ion exchange or hydrophobic interaction chromatography, PEG extraction and crystallization.

One example of purification includes small-scale purification (e.g., less than 1 g) of derivatized enzyme using hydrophobic interaction chromatography. Samples may be filtered and loaded onto a column containing 20HP2 resin (Perceptives Biosystems), hooked up to a BioCad workstation (Perceptives Biosystems). The column may be washed with ammonium sulfate in buffer. Elution of the derivatized phenol oxidizing enzyme activity can be performed using a salt gradient ranging from 35% to 0% of a 3M ammonium sulfate solution in 30 mM Mes Bis Tris Propane buffer at pH 5.4. The fractions enriched in the derivatized phenol oxidizing enzyme activity can be monitored using UV absorbance at 280 nm and a qualitative ABTS activity assay. The samples can be pooled, concentrated and diafiltered against water. Derivatized samples purified according to this method are estimated to be at least about 70% pure.

F. Applications

1. Enzyme and Detergent Compositions

A phenol oxidizing enzyme-peptide complex of the present invention may be used to produce, for example, enzymatic compositions for use in detergent or cleaning compositions; such as for removing food stains on fabrics; and in textiles, that is in the treatment, processing, finishing, polishing, or production of fibers.

Enzymatic compositions may also comprise additional components, such as for example, for formulation or as performance enhancers. For example, detergent compositions may comprise, in addition to the phenol oxidizing enzyme-peptide complex, conventional detergent ingredients such as surfactants, builders and further enzymes such as, for example, proteases, amylases, lipases, cutinases, cellulases or peroxidases (U.S. Pat. No. 4,689,297). Other ingredients include enhancers, stabilizing agents, bactericides, optical brighteners and perfumes. The enzymatic compositions may take any suitable physical form, such as a powder, an aqueous or non-aqueous liquid, a paste or a gel. Reference is made to U.S. Pat. No. 3,929,678; U.S. Pat. No. 4,760,025; U.S. Pat. No. 5,011,681; WO 96/06930; WO 95/01426 and McCutcheon's Detergents and Emulsifiers, North American Ed. (1986) Allured Publishing Co.

A phenol oxidizing enzyme-peptide complex of the present invention can act to modify the color associated with dyes or colored compounds in the presence or absence of enhancers depending upon the characteristics of the compound. If a compound is able to act as a direct substrate for the phenol oxidizing enzyme, the phenol oxidizing enzyme will modify the color associated with a dye or colored compound in the absence of an enhancer, although an enhancer may still be preferred for optimum phenol oxidizing enzyme activity. For other colored compounds unable to act as a direct substrate for the phenol oxidizing enzyme or not directly accessible to the phenol oxidizing enzyme, an enhancer may be required for optimum phenol oxidizing enzyme activity and modification of the color.

Enhancers are described in for example WO 95/01426, WO 96/06930, and WO 97/11217. Enhancers include but are not limited to phenothiazine-10-propionic acid (PTP), 10-methylphenothiazine (MPT), phenoxazine-10-propionic acid (PPO), 10-methylphenoxazine (MPO), 10-ethylphenothiazine-4-carboxylic acid (EPC) acetosyringone, syringaldehyde, methylsyringate, 2,2'-azino-bis (3-ethylbenzothiazoline-6-sulfonate (ABTS), 2,6 dimethoxyphenol (2,6-DMP), and guaiacol (2-methoxyphenol).

Phenol oxidizing enzymes and their use in enzyme and detergent compositions is well known. However, a main advantage of the phenol oxidizing enzyme-peptide complex according to the invention is the binding of the complex to a target stain comprising a carotenoid compound.

2. Other Applications

The phenol oxidizing enzyme-peptide complexes may also be useful in applications other than enzyme and detergent compositions for stain removal. In one preferred embodiment the peptides according to the invention bind preferentially to carotenoid compounds. Therefore, other applications may include personal care applications, for example in skin cosmetics as skin tanners, food industry applications, for example as fruit ripening agents or in diagnostic uses, such as in pharmaceutical applications, for example to localize the presence of carotenoids in tissue.

Having thus described the binding peptides and the phenol oxidizing enzyme-peptide complexes of the present invention, the following examples are now presented for the purposes of illustration and are neither meant to be, nor should they be, read as being restrictive. Dilutions, quantities, etc. which are expressed herein in terms of percentages are, unless otherwise specified, percentages given in terms of per cent weight per volume (w/v). As used herein, dilutions, quantities, etc., which are expressed in terms of % (v/v), refer to percentage in terms of volume per volume. Temperatures referred to herein are given in degrees centigrade (C).

EXPERIMENTAL

EXAMPLE 1

Selection of the Binding Peptides on Stained Cotton

While a number of selection techniques may be used to screen for binding peptides, the majority of the binding peptides according to the invention were selected according to the method described herein below.

10 microliters of a commercially (New England Biolabs) available phage display library either a cyclic 7-mer (at 2.10E13 pfu/ml) or a linear 12-mer (at 4.10E12 pfu/ml) were pre-incubated with a cotton swatch in a pre-blocked and washed 96 well plate in the presence of a 150 µl TBS solution (at 2.10E-5 g/l for the cyclic 7-mer, 2.10E-3 g/l for the linear 12-mer) of detergent, pH 10 for 20 minutes using gentle shaking. The solution was pipetted off and added to a second cotton swatch for 20 minutes under gentle shaking. This process was repeated a third time. The solution was pipetted off and added to a tomato (Textile Innovators, NC) or paprika (Test Fabrics, PA) stained swatch for 60 minutes under gentle agitation. The solution was drawn off and discarded. The stained swatch was washed 5× for 5 minutes each with 200 µl of TBST (TBS containing 0.1% Tween 20). The swatch was transferred to an empty well using sterile tips, washed as described above, and transferred to another empty well. 15 µl of a glycine 0.2M solution pH 2.2 was added to the stained swatch and the plate was shaken for less than 10 minutes. This solution was neutralized by the addition of 100 µl of a Tris HCL 1M solution, pH 9.1 for 10 minutes. The solution, which constitutes the acid eluted peptide population was pipetted off and stored at 4° C. until further use.

4×20 µl of the acid eluted phage peptide population was used to infect 4×400 µl E. coli (New England BioLabs) grown to an OD at 610 nm of 0.3 to 0.65 from a 100× dilution in LB of an overnight culture. The cells were plated on 4×140 mm LB plates in the presence of IPTG (Sigma) (40 µl at 20 mg/ml per plate) and Xgal (Sigma) (40 µl at 40 mg/ml of DMF per plate) added to 5 mls of melted top agarose, and left to incubate overnight at 37° C. The 4 plates were scraped with a sterile glass microscope slide and the scrapings were pushed through an 18.5 gage needle of a 60 ml syringe into a sterile conical tube; 50 ml of TBS was added to the tube and the capped tube was left to shake on a rocker at room temperature for at least 14 hrs. The contents of the tube were centrifuged at 10,000 rpm for 30 minutes in sterile Oakridge tubes at 4° C. The supernatant was collected and the phage precipitated by adding ⅙ volume of a 20% polyethylene glycol (PEG)/2.5 M NaCl solution. This was left to incubate at 4° C. for at least 4 hours and preferably overnight. The solution was then spun at 10,000 rpm for 30 minutes at 4° C. and the supernatant discarded. The pellet was resuspended in 1 ml of TBS and transferred to a sterile Eppendorff tube. The phage was reprecipitated with ⅙ volume of a 20% PEG/2.5 M NaCl solution with incubation on ice for at least 1 hour. This was followed by another centrifugation at 10,000 rpm for 10 min at 4° C. The supernatant was discarded, the tube re-spun briefly, and residual supernatant removed. The pellet was resuspended in 200 µl TBS/0.02% $NaN_3$, spun to remove insoluble material and transferred.

The amplified phage peptide populations from the first round of deselection on cotton/selection of stained cotton swatches were submitted to another round of deselection and selection as described above. For the cyclic 7-mer peptide library 2.10E-4 g/l TBS was used, and for the linear 12-mer peptide library 2.10E-2 g/l TBS was used. After acid elution and amplification of the phage, a third round of biopanning was performed. The third round used 2.10E-3 g/l TBS of detergent for the cyclic 7-mer phage peptides and 2.10E-1 g/l TBS for the linear 12-mer phage peptides. After acid elution and amplification a fourth round of biopanning was used and 2 g/l of detergent dissolved in water in one experiment and TBS in another were used for both types of phage peptides. The phage peptides were acid eluted and amplified from the fourth round of biopanning and selected in a fifth round of biopanning wherein the Tween 20 concentration was increased from 0.1% to 0.8% in the wash conditions. Additionally a round of selection on tomato and paprika was performed using the phage peptides from the third round as described above. In this fourth round 2 g/l of detergent in water in the wash conditions was used. One skilled in the art is well aware that various parameters as described hereinabove may be varied without affecting the nature of the invention. The above described method is one method which may be used to screen for binding peptides of the invention.

EXAMPLE 2

Identification and Sequencing of the Phage Peptide Population

225 µl of a ¹⁄₁₀₀ dilution of an overnight culture of E. coli cells in LB broth were incubated with phage plaques using sterile toothpicks in a sterile 96-well V-bottom plate. A replica plate was made for glycerol stocks of the phage peptides. The plates were covered with porous Qiagen plate sealers and shaken for 4 hours at 37° C. at 280 rpm in a humidified shaker box and then spun at 4000 rpm for 30 min at 4° C. 160 µl of the phage peptides supernatant was transferred to another 96-well V-bottom plate containing 64 µl of 20% PEG/2.5 M NaCl. The plates were left to shake for 5 minutes and then left to stand for 10 minutes. The glycerol stock plate was prepared by adding 100 µl phage supernatant to 150 µl 75% glycerol solution in a sterile 96 well plate which was then sealed with parafilm, labeled, and stored at −70° C. until further use.

The PEG precipitated phage plate was centrifuged at 4000 rpm for 20 minutes at 4° C. The plate was inverted rapidly to remove excess PEG/NaCl and left upside down on a clean paper towel to drain residual fluid. 60 µl of iodide salt solution (10 mM Tris.HCl, pH 8.0, 1 mM EDTA, 4 M NaI) were added to each well and the phage pellets thoroughly resuspended by shaking the plate vigorously for 5 minutes. 150 µl of 100% EtOH were added and the plate was spun at 4000 rpm for 20 minutes at 4° C., the supernatants discarded and the plate blotted. The pellets were washed with 225 µl of 70% EtOH without disturbing the pellets; the plate was inverted and left to air-dry for at least 30 minutes. The pellets were resuspended in 30 µl of Tris.HCl 10 mM, pH 8.5 buffer by shaking the plate for 30 minutes at full speed. 1 µl of g96 reverse primer (obtained from New England BioLabs, 3.4 pmole per tube) was added to 11 µl of DNA pellet sample and the contents submitted for sequencing on a ABI Applied Biosystem 373XL.

FIGS. 1A-1E (SEQ ID NOS: 2-433) illustrate the amino acid sequence of numerous binding peptides determined according to the method herein described. Various repeatable motifs were found in these peptides by visual and computer analyzed methods and repeatable motifs of 3 to 5 amino acid residues are reported in Table 2 along with some representative sequence identifiers for binding peptides illustrated in FIGS. 1A-1E which include the repeatable motif.

EXAMPLE 3

Sites for Attachment and Substitution of Binding Peptides

A. Insertion into the C-Terminus of *Stachybotrys* oxidase B:

Primer Design

Reverse Primer:

```
3' ACTACGGCGACTCCTCNNNNNNNNNNNNNNNN (SEQ ID NO: 434)
NNNNNNNATTAGATCTGGGG 5'
``` wherein the 16 bp overlap with the polynucleotide sequence encoding SEQ ID NO: 1 is underlined, the section of N's symbolizes the polynucleotide encoding a binding peptide of the invention; the ATT stop codon is in bold letters, and the Xba I restriction site is doubled underlined. In a specific example the polynucleotide TTCCGGAGTCGAGGAC-GAAAC (SEQ ID NO: 435) encoding binding peptide KASAPAL (SEQ ID NO: 24) was added to the C-terminus.

Forward Primer HM 358 was used for all PCR reactions.

```
5' AAGGATCCATCAACATGATCAGCCAAG 3' (SEQ ID NO: 436)
```

Various 7-mer, 7-mer with cysteines and 12-mer binding peptides illustrated in FIGS. 1A-1E were inserted into the C-terminus of *Stachybotrys* phenol oxidase B (FIG. 2), and reference is made to FIGS. 3 and 4. Primers were designed as described above. The insertion location was just past E583 at the C-terminus of *Stachybotrys* phenol oxidase B. (Also see FIG. 1 of WO 01/21809). PCR was used for insertion of sequences. 3'-5' peptide primers were designed specifically for the reaction. Ten microliters of diluted DNA were added to a mixture which contained 0.2 mM of each nucleotide (A, G, C and T), 1× reaction buffer, 1.7 microgram of peptide insertion reverse primer and the common forward primer in a 100 μl reaction in an eppendorf tube. After a 5 minute incubation at 100° C., 2.5 units of Taq DNA polymerase was added to the reaction mix. The PCR reaction was begun at 95° C. for 1 minute, followed by primer annealing to the template at 50° C. for 1 minute and extension was done at 72° C. for 1 minute. The cycle was repeated 30 times with an additional cycle extension at 68° C. for 7 minutes, The final PCR product size was 975 bp. Stachybotrys phenol oxidase B (SEQ ID NO: 1) and specific variants thereof M254F and M254F/E346V/E348Q were used as the template for PCR. The fragment was purified with the Qiagen PCR Purification kit. After purification, the fragment was digested with the restriction enzymes BsrG I and Xba I in a joint digestion. The Xba I site was introduced in the PCR reaction. The BsrG I site was located 75 bp downstream from the beginning of the PCR product at I312. Also digested was the nonderivatized *Stachybotrys* B phenol oxidase/pGAPT (without a binding peptide insertion or substitution) in the pGAPT expression vector. *Stachybotrys* B phenol oxidase/pGAPT was also digested with BsrG I and XbaI in order to facilitate cloning of the PCR product into Stachybotrys B phenol oxidase. The digested PCR product was ethanol precipitated to clean and purify the fragment and the digested *Stachybotrys* B phenol oxidase/pGAPT sample was run on a gel to separate the two fragments produced by the reaction (BsrG I and Xba I are both single cutters in *Stachybotrys* B phenol oxidase/pGAPT). The larger of the fragments was 5.8 kb while the smaller of the fragments was 945 bp long. The 5.8 kb fragment was excised from the gel and purified using the Bio 101 Geneclean III kit. The purified PCR fragment and 5.8 kb *Stachybotrys* B phenol oxidase/pGAPT fragment were then ligated together. The ligated DNA was then transformed into Invitrogen Top10 *E.coli*. Individual colonies from the transformation plate were picked and cultured in LB+50 ppm carb. overnight. The plasmid DNA was then isolated and purified using the Qiagen Miniprep kit. The isolated DNA was sequenced to check if peptide sequences were inserted, in the correct location and were the correct sequence. Sequencing was also done earlier in the process after PCR to check insertion of peptide sequences. After PCR was run, the products were ligated into the Invitrogen pCR2.1 cloning vector and sequenced. Samples were then transformed into *Aspergillus niger*.

In addition to KASAPAL (SEQ ID NO: 24), the above procedure was repeated with 98 of the peptides listed in FIGS. 1A-1E. The specific peptides and corresponding sequence identifiers are listed in Table 3 below. Some of the binding were attached using the C—C derivative form. Corresponding 3'-5' primers for the peptides were mixed together and PCR was run with that primer mixture and the 5'-3' primer.

TABLE 3

| | | | |
|---|---|---|---|
| SLLNATK | (SEQ ID NO: 4) | HVQILQLAAPAL | (SEQ ID NO: 94) |
| YGYLPSR | (SEQ ID NO: 16) | YHTPSTGGASPV | (SEQ ID NO: 104) |
| IERSAPATAPPP | (SEQ ID NO: 92) | SSDVPQAARNDA | (SEQ ID NO: 105) |
| VSSPHIY | (SEQ ID NO: 38) | EATFHKD | (SEQ ID NO: 255) |
| MTHPLVH | (SEQ ID NO: 39) | RLSDPMH | (SEQ ID NO: 256) |
| HTFLQTH | (SEQ ID NO: 40) | TDFFGRV | (SEQ ID NO: 257) |
| NTSYQYR | (SEQ ID NO: 41) | GQNPMKS | (SEQ ID NO: 258) |
| GHSMLTN | (SEQ ID NO: 42) | TAPSFTK | (SEQ ID NO: 259) |
| MTPAKPS | (SEQ ID NO: 43) | FDSKNTP | (SEQ ID NO: 260) |
| ISDYPNP | (SEQ ID NO: 44) | QQLNTPR | (SEQ ID NO: 261) |
| DIQRMML | (SEQ ID NO: 45) | HIPSALL | (SEQ ID NO: 262) |

TABLE 3-continued

| | | | |
|---|---|---|---|
| FVLPPVS | (SEQ ID NO: 46) | ELTPALH | (SEQ ID NO: 263) |
| TMGTLLA | (SEQ ID NO: 47) | TPPTKKQ | (SEQ ID NO: 264) |
| HIRAPGN | (SEQ ID NO: 48) | SGIPRNS | (SEQ ID NO: 265) |
| HTSPTSH | (SEQ ID NO: 49) | VQPVTRY | (SEQ ID NO: 266) |
| SSDLPPY | (SEQ ID NO: 50) | KGMHTTD | (SEQ ID NO: 267) |
| WGLASQL | (SEQ ID NO: 51) | PMWGTHL | (SEQ ID NO: 268) |
| PNSHPHW | (SEQ ID NO: 52) | NAAKLEQ | (SEQ ID NO: 269) |
| PTRATPS | (SEQ ID NO: 53) | PQEALQL | (SEQ ID NO: 270) |
| PHPTNLA | (SEQ ID NO: 54) | SRDMHPH | (SEQ ID NO: 271) |
| QISQSQI | (SEQ ID NO: 55) | GPETPYQ | (SEQ ID NO: 272) |
| PSSTWHP | (SEQ ID NO: 56) | SLVQSLE | (SEQ ID NO: 273) |
| ITWDHIN | (SEQ ID NO: 57) | NLTPMAR | (SEQ ID NO: 274) |
| SPNPTST | (SEQ ID NO: 58) | LQSPPLK | (SEQ ID NO: 275) |
| QTSALSR | (SEQ ID NO: 59) | QKHAFRS | (SEQ ID NO: 276) |
| ERRPSKA | (SEQ ID NO: 60) | PWQIKLT | (SEQ ID NO: 277) |
| SMFSKAA | (SEQ ID NO: 61) | QIWHPHNYPGSL | (SEQ ID NO: 120) |
| GHRPHAIKPPPP | (SEQ ID NO: 130) | SSPLQTSPPWPY | (SEQ ID NO: 326) |
| SDYSSAATYYGH | (SEQ ID NO: 131) | KAIGMSTGPLTQ | (SEQ ID NO: 327) |
| SSTSPLLPHMLL | (SEQ ID NO: 132) | LHVTTTIPGGLR | (SEQ ID NO: 328) |
| TSEHTLASKYQS | (SEQ ID NO: 133) | SVPSPSPPWSRP | (SEQ ID NO: 329) |
| SHGIATSETTSN | (SEQ ID NO: 134) | VASANPHSMTSW | (SEQ ID NO: 330) |
| MNPSSSQHKNSH | (SEQ ID NO: 135) | QDATSRFSGLAS | (SEQ ID NO: 331) |
| PWASITPPPLLR | (SEQ ID NO: 136) | AEAITAIPLPVP | (SEQ ID NO: 332) |
| QNLQPPQGFTLG | (SEQ ID NO: 137) | MDPFATIPSTHP | (SEQ ID NO: 333) |
| TTSFSEGILIRS | (SEQ ID NO: 138) | EGNARLAQSLIQ | (SEQ ID NO: 334) |
| NVPTSNTHFGLH | (SEQ ID NO: 139) | MHSPFCSSPCSP | (SEQ ID NO: 335) |
| TGSMRLWTLQTQ | (SEQ ID NO: 140) | SGMPPTITWTRP | (SEQ ID NO: 336) |
| SPARSTVGPYEL | (SEQ ID NO: 141) | WEATPNFMSKII | (SEQ ID NO: 337) |
| SHAITATHLEPS | (SEQ ID NO: 142) | AVSLVPPNLATH | (SEQ ID NO: 338) |
| LQLQLLPYAFPV | (SEQ ID NO: 143) | VPNMTPSSYLSA | (SEQ ID NO: 339) |
| NNLAFTPSGTLR | (SEQ ID NO: 144) | LQPQTWSWARGA | (SEQ ID NO: 340) |
| HFAYTKPMRIPQ | (SEQ ID NO: 145) | TEPTVKHPPLRI | (SEQ ID NO: 341) |
| SSWLHDLPVLPL | (SEQ ID NO: 146) | VALPNQPPRAGL | (SEQ ID NO: 342) |
| SVTYQNYGMNTM | (SEQ ID NO: 147) | GLGYWVMPAPTS | (SEQ ID NO: 343) |
| YAHAGKTTFLLG | (SEQ ID NO: 148) | HNLYMTPPSIMN | (SEQ ID NO: 344) |
| HPPSLPNNVVHP | (SEQ ID NO: 149) | HAEKILSSPGPA | (SEQ ID NO: 345) |
| HLSRFESLMHLM | (SEQ ID NO: 150) | HNMLPPRCCLLP | (SEQ ID NO: 346) |
| WLHLPGSAQNHL | (SEQ ID NO: 151) | | |
| RNRPHIIRPPPP | (SEQ ID NO: 152) | | |

B. Insertion and Substitution into *Stachybotrys* Oxidase B and Variants Thereof:

```
(1) Primer
Design (7-mer, Insertion)
5' NNNNNNNNNNNNNNNNNNNNNNNCCTTTCCCC  (SEQ ID NO: 437)

GAGGGCGG 3'

3' GGTTGGAGGCTCTACAANNNNNNNNNNNNNN  (SEQ ID NO: 438)

NNNNNNNN 5'
``` wherein the overlap with the polynucleotide sequence encoding SEQ ID NO: 1 is underlined and the section of N's indicates the binding peptide coding region.

```
(2) Primer
Design (7-mer, Substitution)
5' GAGGGCGGCAACNNNNNNNNNNNNNNNNNN  (SEQ ID NO: 439)

NNNGATGACGAGACTTTCACC 3'

3' AAGGGGCTCCCGCCGTTGNNNNNNNNNNNN  (SEQ ID NO: 440)

NNNNNNNNNNCTACTGCTCTG 5'
``` wherein the overlap with the polynucleotide sequence encoding SEQ ID NO: 1 is underlined and the section of N's indicates the binding peptide coding region.

In a specific example the primers for insertion of binding peptide sequence SSLNATK (SEQ ID NO: 4) are:

```
Forward Primer
5' TCCCTTCTTAACGCTACTAAGACCTTCTCGG  (SEQ ID NO: 441)

ATGTCGAG 3'

Reverse Primer
3' CCTGTTAGTTGCCTCAAAGGGAAGAATTGCG  (SEQ ID NO: 442)

ATGATTC 5'

In a specific example the
primers for substitution
of binding peptide sequence
SSLNATK (SEQ ID NO: 4) are:
Forward Primer
5' GAGGGCGGCAACTCCCTTCTTAACGCTACTA  (SEQ ID NO: 443)

AGGATGACGAGACTTTCACC 3'

Reverse Primer
3' AAGGGGCTCCCGCCGTTGAGGGAAGAATTGC  (SEQ ID NO: 444)

GATGATTCCTACTGCTCTG 5'
```

Three sites within *Stachybotrys* B phenol oxidase (SEQ ID NO: 1) were chosen for 7-mer and 12-mer peptide insertion: site A located between V379 and P380; site B located between V412 and T413; and site C located between L422 and R423. The amino acid sequence W387, D388, P389, A390, N391, P392, and T393 was chosen for the site of 7-mer peptide substitution. All of the peptides were inserted into the *Stachybotrys* B phenol oxidase sequence using mutagenesis PCR. The PCR reaction allowed the peptide coding sequence to be inserted/substituted into the Stachybotrys B phenol oxidase/pGAPT plasmid without the need for cloning procedures such as restriction digest and ligation. After PCR was run, the plasmid was sequenced to verify the insertion/substitution reaction. PCR was run with the *Stachybotrys* B phenol oxidase/pGAPT full plasmid as the template for the reaction. The DNA was diluted 1:10 to 74.4 ng/μl and either 1.8 or 3.7 μl was added to the reaction, which also contained 0.2 mM of each nucleotide, 1× reaction buffer, and 182 nanograms of primer. 2.5 units of Stratagene PFU Turbo polymerase was added to the reaction mixture. The PCR reaction was done at 95° C. for 35 seconds followed by primer annealing to the template at 55° C. for 1 minute 5 seconds. Extension was done at 68° C. for 15 minutes and 30 seconds. The cycle was repeated 16 times. After the full length plasmid PCR product was purified with the Qiagen PCR purification kit, samples were sequenced for confirmation of peptide insertion/substitution. Successfully inserted or substituted peptides sequences in pGAPT plasmid were transformed into *Aspergillus niger* for expression.

EXAMPLE 4

Expression of Laccase-Peptide Complexes by *Aspergillus* Host Cells

The DNA fragment containing nucleic acid encoding the *Stachybotrys* phenol oxidase B (SEQ ID NO: 1) with the introduced binding peptide followed by a stop codon and an Xba I site was isolated by PCR. The PCR fragment was cloned into the plasmid vector pCR2.1 and subjected to nucleic acid sequencing for verification. The DNA fragment was cloned into the BsrG I to Xba I site to create a plasmid pGAPT (see FIGS. 3 and 4). The pGAPT plasmid was co-transformed with a pHELP1 plasmid (Current Genetics 24:520-524 (1993)) in *Aspergillus niger* to generate transformants containing the replicating plasmid. This process was performed for each of the binding peptide listed in Table 3 Transformants were selected on plates without uridine and grown for 3 days. Spores from the transformants were resuspended in 200 μl of Robosoy media in a 96-well plate and grown for 30° C. for 4 days. Samples were filtered and analyzed for laccase expression.

EXAMPLE 5

Purification of Laccase from Fermentation Cultures

Samples obtained as described in Example 4 were purified using small-scale hydrophobic interaction chromatography. Fermentation cultures were filtered over miracloth to separate the cells from the broth. The filtrate was further filtered through a 0.2 μm Steritop (GP) filter unit. The material was loaded onto a column containing the HIC resin 20 HP2 (Perkin Elmer), connected to a BioCad/Sprint workstation (Perkin Elmer) after the resin had been equilibrated with 1.05 M ammonium sulfate in 30 mM Mes, Bis-tris Propane, pH 5.4 buffer. After washing the column to an ammonium sulfate concentration of 0.75M, the enzyme-peptide complex was eluted using ammonium sulfate gradient going from 0.75M to 0.0M over 5 CVs. All fractions were quickly checked for ABTS activity using a qualitative assay in which 50 μL of fraction were added to 100 μL of an ABTS solution (4.5mM) in a 96 well titer plate; apparition of a teal green color in less than 10 sec indicated the enriched presence of laccase. Reference is made to U.S. Pat. No. 6,168,936 and WO 01/21809. In parallel, the fractions were loaded onto a SDS gel (Nu PAGE, 4-12%, Invitrogen) to assess the purity of the fractions. The enriched and purified fractions were pooled, concentrated using a Pellicon XL unit (MWCO: 8000 Da, Millipore), further concentrated and diafiltered against Milli-Q water using YM-10 centripreps until the permeate reached a conductivity of around 5 μS. The enriched fraction was then frozen at −70° C. in 1 ml aliquots until further use. The purity of the enzyme obtained as described was often superior to 80-90%.

EXAMPLE 6

Preferential Binding of the Binding Peptide YGYLPSR (SEQ ID NO: 16) to Tomato Stain The following stock solutions were prepared:
2 g/L Lever "Multi Acao" detergent (Unilever, Brazil)
10 mM $NiSO_4$
2 mM (GGHGGYGYLPSR) (SEQ ID NO: 455), (referred to as stained peptide (STP) #1)
2 mM (GGHGGCYGYLPSRC) (SEQ ID NO:456), (referred to as stained peptide (STP) #2) 10 mM GGH
OPD (o-phenylene diamine, Sigma P-8287 10 mg tablet/22.5 mL buffer (50 mM HEPES, pH 8.0)
100 mM $H_2O_2$ stock Appropriate amounts of $NiSO_4$ and GGHGGYGYLPSR (SEQ ID NO: 455) stock solutions were mixed to prepare 0.125-1.0 mM Ni-(STP #1) solutions. The resulting solutions were mixed for at least 10 minutes before use to form the Ni-peptide complex. Appropriate amounts of $NiSO_4$ and GGHGGCYGYLPSRC (SEQ ID NO: 456) stock solutions were mixed to prepare 0.125-1.0 mM Ni-(STP #2) solutions. The resulting solutions were mixed for at least 10 minutes before use to form the Ni-peptide complex. Appropriate amounts of $NiSO_4$ and GGH stock solutions were mixed to prepare 0.125-1.0 mM Ni-GGH solutions. The resulting solutions were mixed for at least 10 minutes before use to form the Ni-peptide complex.

An appropriate number of tomato stained cotton swatches and unstained cotton swatches were added to a 96 well plate. 100 μL nickel peptide stock solutions were added to the 96 well plate with the swatches and the resulting mixture incubated for 90 minutes at room temperature with gentle shaking. After incubation, the solution was removed with suction and each swatch rinsed 2 times in 200 μL $dH_2O$ by shaking for 3 minutes. 200 μL OPD solution and 50 μL of $H_2O_2$ solution were added to each well and the plate place on a shaker at moderate speed. The mixture was allowed to incubate overnight and then 200 μL was transferred from each well to a new 96 well plate. Absorbance was read at 430 nm.

FIG. 5 shows a comparison of binding to tomato stain vs. unsoiled cotton from a starting concentration of 0.5 mM Ni-peptide. The NiGGH values were adjusted for higher activity by dividing by 3; to bring the absorbance values in line with the other Ni-peptide values and provide an equal basis of comparison. The plot shows Ni-SEQ ID NO: 455, binds to tomato stain about 4× more than to cotton, Ni-SEQ ID NO: 456, binds to tomato stain about 3× more than to cotton, and NiGGH shows no preferential binding.

EXAMPLE 7

Laccase-Peptide Complex Binding

Four samples were used to test the binding ability and other properties of 3 laccase-peptide complexes according to the invention. As discussed above, the laccase-peptide complex comprised a binding peptide that was attached to the laccase at the C-terminus. The samples included (a) SEQ ID NO: 1-IERSAPATAPPP (SEQ ID NO: 92); (b) SEQ ID NO: 1-KASAPAL (SEQ ID NO: 24); (c) SEQ ID NO: 1—the C—C derivative of KASAPAL (SEQ ID NO: 24); and non-derivatized laccase SEQ ID NO: 1.

A 96 well plate was filled with cotton swatches stained with tomato (Textile Innovators). 90 μL of 83.5 mM sodium carbonate, pH 10 buffer were added to the swatches. 50 μL of purified enzyme dilutions, protein concentrations of 0.6 mg/ml, 0.3 mg/ml and 0.1 mg/ml, were added and the plate was left to incubate at room temperature for an hour using mild shaking. The solution was pipetted off and the swatches rinsed with 150 μL of MilliQ water using strong agitation for 5 min. The rinse pipetted off; the swatches received 150 μL of an ABTS solution (4.5 mM in 50 mM sodium acetate, pH 5). Qualitative estimation of binding of the complex was observed and evaluated by visual determination of the dark green color caused by ABTS oxidation (FIG. 6). As observed the results indicate the superior binding on a protein basis of the laccase-peptide complex versus the original nonderivatized laccase.

Additionally a guaiacol assay and protein concentration were determined as outlined below with results represented in Table 4.

TABLE 4

| SAMPLE | Av ABTS U/ml | Av Guaiacol pH 8.5 U/ml | Av Guaiacol pH 10.0 U/ml | Guaiacol Ratio 10/8.5 | Protein Concentration Mg/ml |
|---|---|---|---|---|---|
| SEQ ID NO: 1-IERSAPATAPPP (SEQ ID NO: 92) | 16.13 | 6.375 | 8.348 | 1.31 | 0.623 |
| SEQ ID NO: 1-KASAPAL (SEQ ID NO: 24) | 18.48 | 8.462 | 11.735 | 1.39 | 1.23 |
| SEQ ID NO: 1-C-SEQ ID NO: 24-C | 21.25 | 11.119 | 14.173 | 1.28 | 0.657 |
| SEQ ID NO: 1 | 12.55 | 7.326 | 7.731 | 1.06 | 1.19 |

The guaiacol assay is also useful for determining phenol oxidizing activity, especially at higher pH levels. The following reagents are used: 50 mM Tris-HCl buffer pH 8.5 (To make 1 L: dissolve 7.8g of Tris-HCL in 1 L of DI water. Mix gently. Calibrate pH probes and adjust pH to 8.5. Buffer should be filter sterilized using a 0.2 um filter); 50 mM Guaiacol in Milli-Q-$H_2O$ (To make 20 mL of 50 mM Guaiacol: dissolve 124 uL of Guaiacol (Sigma catalog number 6-5502) in Milli-Q- $H_2O$. Guaiacol is light sensitive; solutions containing Guaiacol should be kept away from light by shielding container. This reagent solution should be made fresh daily for quality purposes.

The reagents are combined as follows:

| Guaiacol stock solution | final [conc] |
|---|---|
| 750 μL of pH 8.5 Tris-HCl 50 mM buffer | 42 mM Tris-HCl |
| 100 μL of 50 mM Guaiacol | 5.6 mM Guaiacol |

The enzyme-peptide complex sample is diluted in water, if necessary. 750 μL of Tris-HCl buffer, 100 μL of guaiacol, and 50 μL of enzyme are added to a disposable 1.5 mL cuvette. The reaction is allowed to proceed for 30 seconds at ambient room temperature of 21° C. and a reading is taken every 2 seconds using a spectrophotometer at a lambda of 470 nm. Before the first reading, mix the reaction solution well in the cuvette.

The following calculation can be carried out:

$$\text{Specific activity} = ((\Delta\text{OD units/min})/(0.050\ \text{mL}))/([\text{protein}]\ \text{mg/mL})$$

$$= \Delta\text{OD units/min/mg protein}$$

Protein concentration can be estimated, for example, using the BCA protein assay (See, e.g., Smith, P. K., et al (1985) "Measurement of protein using bicinchoninic acid." Anal. Biochem. 150: 76-85).

In an exemplary procedure, employing the Pierce BCA Protein Assay Reagent Kit (Product Cat. 23225) (Pierce; Rockford, Ill.) [Reference: Pierce Protein Assay Reagent Kit Instructions (for protein assay)]:
1) Prepare Pierce BCA Protein kit Working Reagent (WR):
   a) Mix 50 parts of Reagent A (Sodium carbonate, sodium bicarbonate, BCA detection reagent and sodium tartarate in 0.1 M NaOH) with 1 part of Reagent B (4% $CuSO_{4.5}H_2O$)
2) Prepare BSA std.s using 2 mg/mL BSA std. stock soln. See Mfrs. Instructions (diln.s prepared in Milli-Q water)

Chill 20% TCA thoroughly:
1) 50 uL of Sample/Std.s & 50 uL of 20% TCA>mix>put on ice for 20 min.
2) Centrifuge for 10 minutes>Decant>Dry in Speed Vac -Speed Vac: Bring to speed>turn on vac.>run 2 min.>turn vac.
   off>stop and remove samples
3) Resuspend in 50 uL of WR
4) Add 1 mL WR to each tube
5) Incubate at 37° for 30 minutes
6) Cool to Rm. Temp. and read at $562_{nm}$ Plot Standards and Determine Protein Concentrations:
1) Do Scatter plot on Standards
2) Determine trend line
3) Display equation and $R^2$ value:
   use the equation to determine protein conc.: y=mx+b
   where: y=562 nm reading, and x=ug/mL Protein determination in connection with unpurified complexes can be done by way of a different protocol; for example, the protein can be quantified via densitometry on Coomassie stained SDS gels.

EXAMPLE 8

Binding of Laccase-YGYLPSR (SEQ ID NO: 16) to Tomato

Tomato stained cotton swatches (Textile Innovators Corp.) and non-stained cotton swatches (Textile Innovators Corp.) were placed in wells of a 96 well titer plate, previously blocked with a solution of BSA in PBS (Superblock, Pierce), for 2 days at room temperature and rinsed three times with MilliQ water (with 150 ul per well), Dilutions (100 ul) of SEQ ID NO:1, variant M254F/E346V/E348Q-YGYLPSR (SEQ ID NO: 16) or the same variant without SEQ ID NO: 16 (1 mg/ml, 0.1 mg/ml and 0.01 mg/ml) in a commercial detergent solution were added in duplicate to the non-stained cotton swatches and to the tomato stained cotton swatches. Incubation was at 1 hr at room temperature with moderate shaking. The incubation solution was pipetted off and the swatches were washed twice with 150 ul MilliQ water for 1 minute with moderate shaking. 150 ul of a 4.5 mM solution of ABTS in sodium acetate 50 mM, pH 5 buffer were added to each swatch. After 5 minutes incubation under moderate agitation, 100 ul of the ABTS solutions were placed in an empty 96 well plate and the absorbance at 420 nm was read (end point assay) against blanks containing only the original ABTS substrate solution, The average absorbance (n=2) for each concentration of laccase for each type of swatch is depicted in FIG. 7.

The results indicate the derivatized laccase (the M254F/E346V/E348Q variant-SEQ ID NO:16), designated as (A) bound at least 4 to 6 times greater to tomato stained swatches than to non-stained cotton swatches. The results also indicate the nonderivatized laccase (the M254F/E346V/E348Q variant), designated as (B) bound 2 times better to cotton swatches than to tomato stained swatches, and further the nonderivatized laccase (B) bound 2 to 3 times better to cotton swatches than the derivatized laccase (A).

Binding and bleaching experiments were performed with stained tomato cotton swatches, as outlined herein above, for the laccase-peptide complex, variant M254F/E346V/E348Q-SLLNATK (SEQ ID NO: 4) and the corresponding non-derivatized laccase (variant M254F/E346V/E348Q). The laccase-peptide complex resulted in improved bleaching and enhanced binding on a protein basis. (Data not shown)

The Sequence Listing is contained on separately submitted CD-ROM entitled GC690-2-SEQLIST.TXT (81.3 KB) created Nov. 21, 2002 which is incorporated in entirety by reference herewith.

What is claimed is:

1. An isolated polynucleotide sequence encoding a binding peptide having the amino acid sequence of SEQ ID NO:24, wherein said peptide binds to a carotenoid compound.

2. An expression vector comprising a polynucleotide encoding the phenol oxidizing enzyme-peptide complex comprising the amino acid sequence of SEQ ID NO:24.

3. A host cell comprising the vector of claim 2.

* * * * *

SEQUENCE LISTING

<160> NUMBER OF SEQ ID NOS: 446

<210> SEQ ID NO 1
<211> LENGTH: 583
<212> TYPE: PRT
<213> ORGANISM: Stachybotrys chartarum

<400> SEQUENCE: 1

Met Ile Ser Gln Ala Ile Gly Ala Val Ala Leu Gly Leu Ala Val Ile
 1               5                  10                  15

Gly Gly Ser Ser Val Asp Ala Arg Ser Val Ala Gly Arg Ser Thr Asp
            20                  25                  30

Met Pro Ser Gly Leu Thr Lys Arg Gln Thr Gln Leu Ser Pro Pro Leu

```
                    35                  40                  45
Ala Leu Tyr Glu Val Pro Leu Pro Ile Pro Pro Leu Lys Ala Pro Asn
             50                  55                  60

Thr Val Pro Asn Pro Asn Thr Gly Glu Asp Ile Leu Tyr Tyr Glu Met
 65                  70                  75                  80

Glu Ile Arg Pro Phe Ser His Gln Ile Tyr Pro Asp Leu Glu Pro Ala
                 85                  90                  95

Asn Met Val Gly Tyr Asp Gly Met Ser Pro Gly Pro Thr Ile Ile Val
                100                 105                 110

Pro Arg Gly Thr Glu Ser Val Val Arg Phe Val Asn Ser Gly Glu Asn
            115                 120                 125

Thr Ser Pro Asn Ser Val His Leu His Gly Ser Phe Ser Arg Ala Pro
130                 135                 140

Phe Asp Gly Trp Ala Glu Asp Thr Thr Gln Pro Gly Glu Tyr Lys Asp
145                 150                 155                 160

Tyr Tyr Tyr Pro Asn Arg Gln Ala Ala Arg Met Leu Trp Tyr His Asp
                165                 170                 175

His Ala Met Ser Ile Thr Ala Glu Asn Ala Tyr Met Gly Gln Ala Gly
            180                 185                 190

Val Tyr Met Ile Gln Asp Pro Ala Glu Asp Ala Leu Asn Leu Pro Ser
        195                 200                 205

Gly Tyr Gly Glu Phe Asp Ile Pro Leu Val Leu Thr Ala Lys Arg Tyr
    210                 215                 220

Asn Ala Asp Gly Thr Leu Phe Ser Thr Asn Gly Glu Val Ser Ser Phe
225                 230                 235                 240

Trp Gly Asp Val Ile Gln Val Asn Gly Gln Pro Trp Pro Met Leu Asn
                245                 250                 255

Val Gln Pro Arg Lys Tyr Arg Phe Arg Phe Leu Asn Ala Ala Val Ser
            260                 265                 270

Arg Ser Phe Ala Leu Tyr Leu Ala Thr Ser Glu Asp Ser Glu Thr Arg
        275                 280                 285

Leu Pro Phe Gln Val Ile Ala Ala Asp Gly Gly Leu Leu Glu Gly Pro
    290                 295                 300

Val Asp Thr Asp Thr Leu Tyr Ile Ser Met Ala Glu Arg Trp Glu Val
305                 310                 315                 320

Val Ile Asp Phe Ser Thr Phe Ala Gly Gln Ser Ile Asp Ile Arg Asn
                325                 330                 335

Leu Pro Gly Ala Asp Gly Leu Gly Val Glu Pro Glu Phe Asp Asn Thr
            340                 345                 350

Asp Lys Val Met Arg Phe Val Val Asp Glu Val Leu Glu Ser Pro Asp
        355                 360                 365

Thr Ser Glu Val Pro Ala Asn Leu Arg Asp Val Pro Phe Pro Glu Gly
    370                 375                 380

Gly Asn Trp Asp Pro Ala Asn Pro Thr Asp Glu Thr Phe Thr Phe
385                 390                 395                 400

Gly Arg Ala Asn Gly Gln Trp Thr Ile Asn Gly Val Thr Phe Ser Asp
                405                 410                 415

Val Glu Asn Arg Leu Leu Arg Asn Val Pro Arg Asp Thr Val Glu Ile
            420                 425                 430

Trp Arg Leu Glu Asn Asn Ser Asn Gly Trp Thr His Pro Val His Ile
        435                 440                 445

His Leu Val Asp Phe Arg Val Leu Ser Arg Ser Thr Ala Arg Gly Val
    450                 455                 460
```

```
Glu Pro Tyr Glu Ala Ala Gly Leu Lys Asp Val Val Trp Leu Ala Arg
465                 470                 475                 480

Arg Glu Val Val Tyr Val Glu Ala His Tyr Ala Pro Phe Pro Gly Val
                485                 490                 495

Tyr Met Leu His Cys His Asn Leu Ile His Glu Asp His Asp Met Met
            500                 505                 510

Ala Ala Phe Asn Val Thr Val Leu Gly Asp Tyr Gly Tyr Asn Tyr Thr
            515                 520                 525

Glu Phe Ile Asp Pro Met Glu Pro Leu Trp Arg Pro Arg Pro Phe Leu
        530                 535                 540

Leu Gly Glu Phe Glu Asn Gly Ser Gly Asp Phe Ser Glu Leu Ala Ile
545             550                 555                 560

Thr Asp Arg Ile Gln Glu Met Ala Ser Phe Asn Pro Tyr Ala Gln Ala
                565                 570                 575

Asp Asp Asp Ala Ala Glu Glu
            580
```

```
<210> SEQ ID NO 2
<211> LENGTH: 7
<212> TYPE: PRT
<213> ORGANISM: Artificial Sequence
<220> FEATURE:
<223> OTHER INFORMATION: binding peptide

<400> SEQUENCE: 2

Thr Gly Met Ser Leu His His
1               5

<210> SEQ ID NO 3
<211> LENGTH: 7
<212> TYPE: PRT
<213> ORGANISM: Artificial Sequence
<220> FEATURE:
<223> OTHER INFORMATION: binding peptide

<400> SEQUENCE: 3

Pro Leu Thr Thr Ser Pro Val
1               5

<210> SEQ ID NO 4
<211> LENGTH: 7
<212> TYPE: PRT
<213> ORGANISM: Artificial Sequence
<220> FEATURE:
<223> OTHER INFORMATION: binding peptide

<400> SEQUENCE: 4

Ser Leu Leu Asn Ala Thr Lys
1               5

<210> SEQ ID NO 5
<211> LENGTH: 7
<212> TYPE: PRT
<213> ORGANISM: Artificial Sequence
<220> FEATURE:
<223> OTHER INFORMATION: binding peptide

<400> SEQUENCE: 5

Gln Asn Glu His Asn Leu Ala
1               5

<210> SEQ ID NO 6
```

```
<211> LENGTH: 7
<212> TYPE: PRT
<213> ORGANISM: Artificial Sequence
<220> FEATURE:
<223> OTHER INFORMATION: binding peptide

<400> SEQUENCE: 6

Pro Phe Asn Thr Leu Asp Arg
 1               5

<210> SEQ ID NO 7
<211> LENGTH: 7
<212> TYPE: PRT
<213> ORGANISM: Artificial Sequence
<220> FEATURE:
<223> OTHER INFORMATION: binding peptide

<400> SEQUENCE: 7

Arg Asn Tyr Thr Gly Ala Ala
 1               5

<210> SEQ ID NO 8
<211> LENGTH: 7
<212> TYPE: PRT
<213> ORGANISM: Artificial Sequence
<220> FEATURE:
<223> OTHER INFORMATION: binding peptide

<400> SEQUENCE: 8

Leu Pro Gly Pro Ser His Phe
 1               5

<210> SEQ ID NO 9
<211> LENGTH: 7
<212> TYPE: PRT
<213> ORGANISM: Artificial Sequence
<220> FEATURE:
<223> OTHER INFORMATION: binding peptide

<400> SEQUENCE: 9

Ser Lys Asn Glu Gly Arg Thr
 1               5

<210> SEQ ID NO 10
<211> LENGTH: 7
<212> TYPE: PRT
<213> ORGANISM: Artificial Sequence
<220> FEATURE:
<223> OTHER INFORMATION: binding peptide

<400> SEQUENCE: 10

Trp Tyr Ala Asn Lys Thr Met
 1               5

<210> SEQ ID NO 11
<211> LENGTH: 7
<212> TYPE: PRT
<213> ORGANISM: Artificial Sequence
<220> FEATURE:
<223> OTHER INFORMATION: binding peptide

<400> SEQUENCE: 11

Phe Pro Lys Thr Thr Pro Ile
 1               5

<210> SEQ ID NO 12
<211> LENGTH: 7
```

```
<212> TYPE: PRT
<213> ORGANISM: Artificial Sequence
<220> FEATURE:
<223> OTHER INFORMATION: binding peptide

<400> SEQUENCE: 12

Ile Ser Asp Phe Lys Phe Met
1               5

<210> SEQ ID NO 13
<211> LENGTH: 7
<212> TYPE: PRT
<213> ORGANISM: Artificial Sequence
<220> FEATURE:
<223> OTHER INFORMATION: binding peptide

<400> SEQUENCE: 13

Gly Asn Ser Ala Trp Phe Phe
1               5

<210> SEQ ID NO 14
<211> LENGTH: 7
<212> TYPE: PRT
<213> ORGANISM: Artificial Sequence
<220> FEATURE:
<223> OTHER INFORMATION: binding peptide

<400> SEQUENCE: 14

Asn Thr Ser Ile Gln Arg Asn
1               5

<210> SEQ ID NO 15
<211> LENGTH: 7
<212> TYPE: PRT
<213> ORGANISM: Artificial Sequence
<220> FEATURE:
<223> OTHER INFORMATION: binding peptide

<400> SEQUENCE: 15

Ser Ser Lys Trp His Tyr Asn
1               5

<210> SEQ ID NO 16
<211> LENGTH: 7
<212> TYPE: PRT
<213> ORGANISM: Artificial Sequence
<220> FEATURE:
<223> OTHER INFORMATION: binding peptide

<400> SEQUENCE: 16

Tyr Gly Tyr Leu Pro Ser Arg
1               5

<210> SEQ ID NO 17
<211> LENGTH: 7
<212> TYPE: PRT
<213> ORGANISM: Artificial Sequence
<220> FEATURE:
<223> OTHER INFORMATION: binding peptide

<400> SEQUENCE: 17

Thr Pro Ser Tyr Trp Gln Asp
1               5

<210> SEQ ID NO 18
<211> LENGTH: 7
<212> TYPE: PRT
```

<213> ORGANISM: Artificial Sequence
<220> FEATURE:
<223> OTHER INFORMATION: binding peptide

<400> SEQUENCE: 18

Asn Thr Ser Arg Leu Phe His
1               5

<210> SEQ ID NO 19
<211> LENGTH: 7
<212> TYPE: PRT
<213> ORGANISM: Artificial Sequence
<220> FEATURE:
<223> OTHER INFORMATION: binding peptide

<400> SEQUENCE: 19

Ser Gln Gln Gln Arg Gln Tyr
1               5

<210> SEQ ID NO 20
<211> LENGTH: 7
<212> TYPE: PRT
<213> ORGANISM: Artificial Sequence
<220> FEATURE:
<223> OTHER INFORMATION: binding peptide

<400> SEQUENCE: 20

Ala Pro Ser Glu Asn Gln Val
1               5

<210> SEQ ID NO 21
<211> LENGTH: 7
<212> TYPE: PRT
<213> ORGANISM: Artificial Sequence
<220> FEATURE:
<223> OTHER INFORMATION: binding peptide

<400> SEQUENCE: 21

Lys Tyr Leu Asn Asp Gln Arg
1               5

<210> SEQ ID NO 22
<211> LENGTH: 7
<212> TYPE: PRT
<213> ORGANISM: Artificial Sequence
<220> FEATURE:
<223> OTHER INFORMATION: binding peptide

<400> SEQUENCE: 22

Lys Pro Thr Ala Thr Asn Ile
1               5

<210> SEQ ID NO 23
<211> LENGTH: 7
<212> TYPE: PRT
<213> ORGANISM: Artificial Sequence
<220> FEATURE:
<223> OTHER INFORMATION: binding peptide

<400> SEQUENCE: 23

Ala Pro Pro Ala Gln Gly Ser
1               5

<210> SEQ ID NO 24
<211> LENGTH: 7
<212> TYPE: PRT
<213> ORGANISM: Artificial Sequence

```
<220> FEATURE:
<223> OTHER INFORMATION: binding peptide

<400> SEQUENCE: 24

Lys Ala Ser Ala Pro Ala Leu
 1               5

<210> SEQ ID NO 25
<211> LENGTH: 7
<212> TYPE: PRT
<213> ORGANISM: Artificial Sequence
<220> FEATURE:
<223> OTHER INFORMATION: binding peptide

<400> SEQUENCE: 25

Lys Ser Asp His Trp Lys Asn
 1               5

<210> SEQ ID NO 26
<211> LENGTH: 7
<212> TYPE: PRT
<213> ORGANISM: Artificial Sequence
<220> FEATURE:
<223> OTHER INFORMATION: binding peptide

<400> SEQUENCE: 26

Leu Val Asn Lys His Gln Ser
 1               5

<210> SEQ ID NO 27
<211> LENGTH: 7
<212> TYPE: PRT
<213> ORGANISM: Artificial Sequence
<220> FEATURE:
<223> OTHER INFORMATION: binding peptide

<400> SEQUENCE: 27

Lys Leu Asn Ala Asn Asn Phe
 1               5

<210> SEQ ID NO 28
<211> LENGTH: 7
<212> TYPE: PRT
<213> ORGANISM: Artificial Sequence
<220> FEATURE:
<223> OTHER INFORMATION: binding peptide

<400> SEQUENCE: 28

Thr Gln His Met Lys Lys Ala
 1               5

<210> SEQ ID NO 29
<211> LENGTH: 7
<212> TYPE: PRT
<213> ORGANISM: Artificial Sequence
<220> FEATURE:
<223> OTHER INFORMATION: binding peptide

<400> SEQUENCE: 29

Ser His Ser Pro Tyr Ser Arg
 1               5

<210> SEQ ID NO 30
<211> LENGTH: 7
<212> TYPE: PRT
<213> ORGANISM: Artificial Sequence
<220> FEATURE:
```

```
<223> OTHER INFORMATION: binding peptide

<400> SEQUENCE: 30

Leu Gln Ser His Lys Asp His
 1               5

<210> SEQ ID NO 31
<211> LENGTH: 7
<212> TYPE: PRT
<213> ORGANISM: Artificial Sequence
<220> FEATURE:
<223> OTHER INFORMATION: binding peptide

<400> SEQUENCE: 31

Ser Ser Lys Ser Leu Ala Val
 1               5

<210> SEQ ID NO 32
<211> LENGTH: 7
<212> TYPE: PRT
<213> ORGANISM: Artificial Sequence
<220> FEATURE:
<223> OTHER INFORMATION: binding peptide

<400> SEQUENCE: 32

His Asp Ser Leu His Gly Lys
 1               5

<210> SEQ ID NO 33
<211> LENGTH: 7
<212> TYPE: PRT
<213> ORGANISM: Artificial Sequence
<220> FEATURE:
<223> OTHER INFORMATION: binding peptide

<400> SEQUENCE: 33

Thr Asp Trp Asn Gly Trp His
 1               5

<210> SEQ ID NO 34
<211> LENGTH: 7
<212> TYPE: PRT
<213> ORGANISM: Artificial Sequence
<220> FEATURE:
<223> OTHER INFORMATION: binding peptide

<400> SEQUENCE: 34

Val Pro Trp Leu Thr Asn Ser
 1               5

<210> SEQ ID NO 35
<211> LENGTH: 7
<212> TYPE: PRT
<213> ORGANISM: Artificial Sequence
<220> FEATURE:
<223> OTHER INFORMATION: binding peptide

<400> SEQUENCE: 35

Leu Ser Pro Gln Asp Arg Tyr
 1               5

<210> SEQ ID NO 36
<211> LENGTH: 7
<212> TYPE: PRT
<213> ORGANISM: Artificial Sequence
<220> FEATURE:
<223> OTHER INFORMATION: binding peptide
```

```
<400> SEQUENCE: 36

Leu Thr His Gly Pro Lys His
1               5

<210> SEQ ID NO 37
<211> LENGTH: 7
<212> TYPE: PRT
<213> ORGANISM: Artificial Sequence
<220> FEATURE:
<223> OTHER INFORMATION: binding peptide

<400> SEQUENCE: 37

His Leu Asn Gln His His Thr
1               5

<210> SEQ ID NO 38
<211> LENGTH: 7
<212> TYPE: PRT
<213> ORGANISM: Artificial Sequence
<220> FEATURE:
<223> OTHER INFORMATION: binding peptide

<400> SEQUENCE: 38

Val Ser Ser Pro His Ile Tyr
1               5

<210> SEQ ID NO 39
<211> LENGTH: 7
<212> TYPE: PRT
<213> ORGANISM: Artificial Sequence
<220> FEATURE:
<223> OTHER INFORMATION: binding peptide

<400> SEQUENCE: 39

Met Thr His Pro Leu Val His
1               5

<210> SEQ ID NO 40
<211> LENGTH: 7
<212> TYPE: PRT
<213> ORGANISM: Artificial Sequence
<220> FEATURE:
<223> OTHER INFORMATION: binding peptide

<400> SEQUENCE: 40

His Thr Phe Leu Gln Thr His
1               5

<210> SEQ ID NO 41
<211> LENGTH: 7
<212> TYPE: PRT
<213> ORGANISM: Artificial Sequence
<220> FEATURE:
<223> OTHER INFORMATION: binding peptide

<400> SEQUENCE: 41

Asn Thr Ser Tyr Gln Tyr Arg
1               5

<210> SEQ ID NO 42
<211> LENGTH: 7
<212> TYPE: PRT
<213> ORGANISM: Artificial Sequence
<220> FEATURE:
<223> OTHER INFORMATION: binding peptide
```

```
<400> SEQUENCE: 42

Gly His Ser Met Leu Thr Asn
1               5

<210> SEQ ID NO 43
<211> LENGTH: 7
<212> TYPE: PRT
<213> ORGANISM: Artificial Sequence
<220> FEATURE:
<223> OTHER INFORMATION: binding peptide

<400> SEQUENCE: 43

Met Thr Pro Ala Lys Pro Ser
1               5

<210> SEQ ID NO 44
<211> LENGTH: 7
<212> TYPE: PRT
<213> ORGANISM: Artificial Sequence
<220> FEATURE:
<223> OTHER INFORMATION: binding peptide

<400> SEQUENCE: 44

Ile Ser Asp Tyr Pro Asn Pro
1               5

<210> SEQ ID NO 45
<211> LENGTH: 7
<212> TYPE: PRT
<213> ORGANISM: Artificial Sequence
<220> FEATURE:
<223> OTHER INFORMATION: binding peptide

<400> SEQUENCE: 45

Asp Ile Gln Arg Met Met Leu
1               5

<210> SEQ ID NO 46
<211> LENGTH: 7
<212> TYPE: PRT
<213> ORGANISM: Artificial Sequence
<220> FEATURE:
<223> OTHER INFORMATION: binding peptide

<400> SEQUENCE: 46

Phe Val Leu Pro Pro Val Ser
1               5

<210> SEQ ID NO 47
<211> LENGTH: 7
<212> TYPE: PRT
<213> ORGANISM: Artificial Sequence
<220> FEATURE:
<223> OTHER INFORMATION: binding peptide

<400> SEQUENCE: 47

Thr Met Gly Thr Leu Leu Ala
1               5

<210> SEQ ID NO 48
<211> LENGTH: 7
<212> TYPE: PRT
<213> ORGANISM: Artificial Sequence
<220> FEATURE:
<223> OTHER INFORMATION: binding peptide

<400> SEQUENCE: 48
```

His Ile Arg Ala Pro Gly Asn
1               5

<210> SEQ ID NO 49
<211> LENGTH: 7
<212> TYPE: PRT
<213> ORGANISM: Artificial Sequence
<220> FEATURE:
<223> OTHER INFORMATION: binding peptide

<400> SEQUENCE: 49

His Thr Ser Pro Thr Ser His
1               5

<210> SEQ ID NO 50
<211> LENGTH: 7
<212> TYPE: PRT
<213> ORGANISM: Artificial Sequence
<220> FEATURE:
<223> OTHER INFORMATION: binding peptide

<400> SEQUENCE: 50

Ser Ser Asp Leu Pro Pro Tyr
1               5

<210> SEQ ID NO 51
<211> LENGTH: 7
<212> TYPE: PRT
<213> ORGANISM: Artificial Sequence
<220> FEATURE:
<223> OTHER INFORMATION: binding peptide

<400> SEQUENCE: 51

Trp Gly Leu Ala Ser Gln Leu
1               5

<210> SEQ ID NO 52
<211> LENGTH: 7
<212> TYPE: PRT
<213> ORGANISM: Artificial Sequence
<220> FEATURE:
<223> OTHER INFORMATION: binding peptide

<400> SEQUENCE: 52

Pro Asn Ser His Pro His Trp
1               5

<210> SEQ ID NO 53
<211> LENGTH: 7
<212> TYPE: PRT
<213> ORGANISM: Artificial Sequence
<220> FEATURE:
<223> OTHER INFORMATION: binding peptide

<400> SEQUENCE: 53

Pro Thr Arg Ala Thr Pro Ser
1               5

<210> SEQ ID NO 54
<211> LENGTH: 7
<212> TYPE: PRT
<213> ORGANISM: Artificial Sequence
<220> FEATURE:
<223> OTHER INFORMATION: binding peptide

<400> SEQUENCE: 54

```
Pro His Pro Thr Asn Leu Ala
1               5

<210> SEQ ID NO 55
<211> LENGTH: 7
<212> TYPE: PRT
<213> ORGANISM: Artificial Sequence
<220> FEATURE:
<223> OTHER INFORMATION: binding peptide

<400> SEQUENCE: 55

Gln Ile Ser Gln Ser Gln Ile
1               5

<210> SEQ ID NO 56
<211> LENGTH: 7
<212> TYPE: PRT
<213> ORGANISM: Artificial Sequence
<220> FEATURE:
<223> OTHER INFORMATION: binding peptide

<400> SEQUENCE: 56

Pro Ser Ser Thr Trp His Pro
1               5

<210> SEQ ID NO 57
<211> LENGTH: 7
<212> TYPE: PRT
<213> ORGANISM: Artificial Sequence
<220> FEATURE:
<223> OTHER INFORMATION: binding peptide

<400> SEQUENCE: 57

Ile Thr Trp Asp His Ile Asn
1               5

<210> SEQ ID NO 58
<211> LENGTH: 7
<212> TYPE: PRT
<213> ORGANISM: Artificial Sequence
<220> FEATURE:
<223> OTHER INFORMATION: binding peptide

<400> SEQUENCE: 58

Ser Pro Asn Pro Thr Ser Thr
1               5

<210> SEQ ID NO 59
<211> LENGTH: 7
<212> TYPE: PRT
<213> ORGANISM: Artificial Sequence
<220> FEATURE:
<223> OTHER INFORMATION: binding peptide

<400> SEQUENCE: 59

Gln Thr Ser Ala Leu Ser Arg
1               5

<210> SEQ ID NO 60
<211> LENGTH: 7
<212> TYPE: PRT
<213> ORGANISM: Artificial Sequence
<220> FEATURE:
<223> OTHER INFORMATION: binding peptide

<400> SEQUENCE: 60

Glu Arg Arg Pro Ser Lys Ala
```

```
<210> SEQ ID NO 61
<211> LENGTH: 7
<212> TYPE: PRT
<213> ORGANISM: Artificial Sequence
<220> FEATURE:
<223> OTHER INFORMATION: binding peptide

<400> SEQUENCE: 61

Ser Met Phe Ser Lys Ala Ala
1               5

<210> SEQ ID NO 62
<211> LENGTH: 7
<212> TYPE: PRT
<213> ORGANISM: Artificial Sequence
<220> FEATURE:
<223> OTHER INFORMATION: binding peptide

<400> SEQUENCE: 62

Gln Pro Thr Leu Gly Gln Met
1               5

<210> SEQ ID NO 63
<211> LENGTH: 7
<212> TYPE: PRT
<213> ORGANISM: Artificial Sequence
<220> FEATURE:
<223> OTHER INFORMATION: binding peptide

<400> SEQUENCE: 63

Thr Arg Thr Met Asn Phe Thr
1               5

<210> SEQ ID NO 64
<211> LENGTH: 7
<212> TYPE: PRT
<213> ORGANISM: Artificial Sequence
<220> FEATURE:
<223> OTHER INFORMATION: binding peptide

<400> SEQUENCE: 64

Lys Pro Trp Asn Ala Glu Lys
1               5

<210> SEQ ID NO 65
<211> LENGTH: 7
<212> TYPE: PRT
<213> ORGANISM: Artificial Sequence
<220> FEATURE:
<223> OTHER INFORMATION: binding peptide

<400> SEQUENCE: 65

Arg Ala Asp Thr Ser Gly His
1               5

<210> SEQ ID NO 66
<211> LENGTH: 7
<212> TYPE: PRT
<213> ORGANISM: Artificial Sequence
<220> FEATURE:
<223> OTHER INFORMATION: binding peptide

<400> SEQUENCE: 66

Lys Ala Ser Val Ala Gln Gln
1               5
```

```
<210> SEQ ID NO 67
<211> LENGTH: 7
<212> TYPE: PRT
<213> ORGANISM: Artificial Sequence
<220> FEATURE:
<223> OTHER INFORMATION: binding peptide

<400> SEQUENCE: 67

Ser Gly Leu Trp Pro Gly Phe
 1               5

<210> SEQ ID NO 68
<211> LENGTH: 7
<212> TYPE: PRT
<213> ORGANISM: Artificial Sequence
<220> FEATURE:
<223> OTHER INFORMATION: binding peptide

<400> SEQUENCE: 68

Asn Arg Ser Ala Glu Gly Val
 1               5

<210> SEQ ID NO 69
<211> LENGTH: 7
<212> TYPE: PRT
<213> ORGANISM: Artificial Sequence
<220> FEATURE:
<223> OTHER INFORMATION: binding peptide

<400> SEQUENCE: 69

Ser Thr Arg Leu Thr Thr Glu
 1               5

<210> SEQ ID NO 70
<211> LENGTH: 7
<212> TYPE: PRT
<213> ORGANISM: Artificial Sequence
<220> FEATURE:
<223> OTHER INFORMATION: binding peptide

<400> SEQUENCE: 70

Pro Pro His Gly Ala Leu Arg
 1               5

<210> SEQ ID NO 71
<211> LENGTH: 7
<212> TYPE: PRT
<213> ORGANISM: Artificial Sequence
<220> FEATURE:
<223> OTHER INFORMATION: binding peptide

<400> SEQUENCE: 71

Asn Gly Thr Trp Ser Ala Lys
 1               5

<210> SEQ ID NO 72
<211> LENGTH: 7
<212> TYPE: PRT
<213> ORGANISM: Artificial Sequence
<220> FEATURE:
<223> OTHER INFORMATION: binding peptide

<400> SEQUENCE: 72

Ala Pro Ser Arg Met Met Ile
 1               5
```

```
<210> SEQ ID NO 73
<211> LENGTH: 7
<212> TYPE: PRT
<213> ORGANISM: Artificial Sequence
<220> FEATURE:
<223> OTHER INFORMATION: binding peptide

<400> SEQUENCE: 73

Asn Thr Leu Trp Gln Ser Pro
 1               5

<210> SEQ ID NO 74
<211> LENGTH: 7
<212> TYPE: PRT
<213> ORGANISM: Artificial Sequence
<220> FEATURE:
<223> OTHER INFORMATION: binding peptide

<400> SEQUENCE: 74

Lys His Thr His Met Thr Ala
 1               5

<210> SEQ ID NO 75
<211> LENGTH: 7
<212> TYPE: PRT
<213> ORGANISM: Artificial Sequence
<220> FEATURE:
<223> OTHER INFORMATION: binding peptide

<400> SEQUENCE: 75

Ser Phe Thr Lys Asn Asn Trp
 1               5

<210> SEQ ID NO 76
<211> LENGTH: 7
<212> TYPE: PRT
<213> ORGANISM: Artificial Sequence
<220> FEATURE:
<223> OTHER INFORMATION: binding peptide

<400> SEQUENCE: 76

Lys His Ser Ser Leu Thr Thr
 1               5

<210> SEQ ID NO 77
<211> LENGTH: 7
<212> TYPE: PRT
<213> ORGANISM: Artificial Sequence
<220> FEATURE:
<223> OTHER INFORMATION: binding peptide

<400> SEQUENCE: 77

Ser Thr Ser Leu Leu Asn Ala
 1               5

<210> SEQ ID NO 78
<211> LENGTH: 7
<212> TYPE: PRT
<213> ORGANISM: Artificial Sequence
<220> FEATURE:
<223> OTHER INFORMATION: binding peptide

<400> SEQUENCE: 78

Lys Tyr Gln Tyr Lys His Ala
 1               5
```

```
<210> SEQ ID NO 79
<211> LENGTH: 7
<212> TYPE: PRT
<213> ORGANISM: Artificial Sequence
<220> FEATURE:
<223> OTHER INFORMATION: binding peptide

<400> SEQUENCE: 79

Pro Tyr Ser His Ser Arg Phe
 1               5

<210> SEQ ID NO 80
<211> LENGTH: 7
<212> TYPE: PRT
<213> ORGANISM: Artificial Sequence
<220> FEATURE:
<223> OTHER INFORMATION: binding peptide

<400> SEQUENCE: 80

Glu Ser Ala Arg Trp Ser Leu
 1               5

<210> SEQ ID NO 81
<211> LENGTH: 7
<212> TYPE: PRT
<213> ORGANISM: Artificial Sequence
<220> FEATURE:
<223> OTHER INFORMATION: binding peptide

<400> SEQUENCE: 81

Leu Pro Gln Ile Gln Arg Ile
 1               5

<210> SEQ ID NO 82
<211> LENGTH: 7
<212> TYPE: PRT
<213> ORGANISM: Artificial Sequence
<220> FEATURE:
<223> OTHER INFORMATION: binding peptide

<400> SEQUENCE: 82

Asn Pro Asp Leu Arg His Asn
 1               5

<210> SEQ ID NO 83
<211> LENGTH: 7
<212> TYPE: PRT
<213> ORGANISM: Artificial Sequence
<220> FEATURE:
<223> OTHER INFORMATION: binding peptide

<400> SEQUENCE: 83

Leu Pro Thr Pro Lys Ala His
 1               5

<210> SEQ ID NO 84
<211> LENGTH: 7
<212> TYPE: PRT
<213> ORGANISM: Artificial Sequence
<220> FEATURE:
<223> OTHER INFORMATION: binding peptide

<400> SEQUENCE: 84

Thr Gln Thr Ser Leu Thr Lys
 1               5

<210> SEQ ID NO 85
```

<211> LENGTH: 7
<212> TYPE: PRT
<213> ORGANISM: Artificial Sequence
<220> FEATURE:
<223> OTHER INFORMATION: binding peptide

<400> SEQUENCE: 85

Phe Ser Leu Tyr Asp Ala Thr
1               5

<210> SEQ ID NO 86
<211> LENGTH: 7
<212> TYPE: PRT
<213> ORGANISM: Artificial Sequence
<220> FEATURE:
<223> OTHER INFORMATION: binding peptide

<400> SEQUENCE: 86

Pro Val His Thr His Asn Trp
1               5

<210> SEQ ID NO 87
<211> LENGTH: 7
<212> TYPE: PRT
<213> ORGANISM: Artificial Sequence
<220> FEATURE:
<223> OTHER INFORMATION: binding peptide

<400> SEQUENCE: 87

Ser Met Tyr Val Glu Gly Asn
1               5

<210> SEQ ID NO 88
<211> LENGTH: 7
<212> TYPE: PRT
<213> ORGANISM: Artificial Sequence
<220> FEATURE:
<223> OTHER INFORMATION: binding peptide

<400> SEQUENCE: 88

Thr Ser Gln His Tyr Arg Ser
1               5

<210> SEQ ID NO 89
<211> LENGTH: 7
<212> TYPE: PRT
<213> ORGANISM: Artificial Sequence
<220> FEATURE:
<223> OTHER INFORMATION: binding peptide

<400> SEQUENCE: 89

His Tyr Thr Thr Asp Arg His
1               5

<210> SEQ ID NO 90
<211> LENGTH: 12
<212> TYPE: PRT
<213> ORGANISM: Artificial Sequence
<220> FEATURE:
<223> OTHER INFORMATION: binding peptide

<400> SEQUENCE: 90

Ser Phe Gly His Ser Thr Phe Trp His Pro Val Leu
1               5                   10

<210> SEQ ID NO 91
<211> LENGTH: 12

```
<212> TYPE: PRT
<213> ORGANISM: Artificial Sequence
<220> FEATURE:
<223> OTHER INFORMATION: binding peptide

<400> SEQUENCE: 91

Thr Pro Pro Ile Tyr Trp His Arg Met Ala Asp Thr
 1               5                  10

<210> SEQ ID NO 92
<211> LENGTH: 12
<212> TYPE: PRT
<213> ORGANISM: Artificial Sequence
<220> FEATURE:
<223> OTHER INFORMATION: binding peptide

<400> SEQUENCE: 92

Ile Glu Arg Ser Ala Pro Ala Thr Ala Pro Pro Pro
 1               5                  10

<210> SEQ ID NO 93
<211> LENGTH: 12
<212> TYPE: PRT
<213> ORGANISM: Artificial Sequence
<220> FEATURE:
<223> OTHER INFORMATION: binding peptide

<400> SEQUENCE: 93

Asn Pro Thr Thr Thr Tyr Lys Met Thr Pro Thr Met
 1               5                  10

<210> SEQ ID NO 94
<211> LENGTH: 12
<212> TYPE: PRT
<213> ORGANISM: Artificial Sequence
<220> FEATURE:
<223> OTHER INFORMATION: binding peptide

<400> SEQUENCE: 94

His Val Gln Ile Leu Gln Leu Ala Ala Pro Ala Leu
 1               5                  10

<210> SEQ ID NO 95
<211> LENGTH: 12
<212> TYPE: PRT
<213> ORGANISM: Artificial Sequence
<220> FEATURE:
<223> OTHER INFORMATION: binding peptide

<400> SEQUENCE: 95

His Val Thr Asn Pro Thr Ser Pro Arg Pro Val Ala
 1               5                  10

<210> SEQ ID NO 96
<211> LENGTH: 12
<212> TYPE: PRT
<213> ORGANISM: Artificial Sequence
<220> FEATURE:
<223> OTHER INFORMATION: binding peptide

<400> SEQUENCE: 96

Thr Pro Trp Met Gln Asn Thr Ile Tyr Arg Pro His
 1               5                  10

<210> SEQ ID NO 97
<211> LENGTH: 12
<212> TYPE: PRT
```

```
<213> ORGANISM: Artificial Sequence
<220> FEATURE:
<223> OTHER INFORMATION: binding peptide

<400> SEQUENCE: 97

Leu Pro Ser Leu Leu Val Ser His Leu Phe Asp Met
 1               5                  10

<210> SEQ ID NO 98
<211> LENGTH: 12
<212> TYPE: PRT
<213> ORGANISM: Artificial Sequence
<220> FEATURE:
<223> OTHER INFORMATION: binding peptide

<400> SEQUENCE: 98

Ser Phe Pro Gly Lys Phe Leu Ser Leu His Thr Ser
 1               5                  10

<210> SEQ ID NO 99
<211> LENGTH: 12
<212> TYPE: PRT
<213> ORGANISM: Artificial Sequence
<220> FEATURE:
<223> OTHER INFORMATION: binding peptide

<400> SEQUENCE: 99

Tyr Lys Asn Ala Ile Pro Glu Asp Leu Arg Glu Leu
 1               5                  10

<210> SEQ ID NO 100
<211> LENGTH: 12
<212> TYPE: PRT
<213> ORGANISM: Artificial Sequence
<220> FEATURE:
<223> OTHER INFORMATION: binding peptide

<400> SEQUENCE: 100

Ser Gly Glu Phe Asn Gln Trp Pro Ser Ser Lys Pro
 1               5                  10

<210> SEQ ID NO 101
<211> LENGTH: 12
<212> TYPE: PRT
<213> ORGANISM: Artificial Sequence
<220> FEATURE:
<223> OTHER INFORMATION: binding peptide

<400> SEQUENCE: 101

Ser Tyr Leu Asn His Leu Pro Gln Arg Pro Leu Ser
 1               5                  10

<210> SEQ ID NO 102
<211> LENGTH: 12
<212> TYPE: PRT
<213> ORGANISM: Artificial Sequence
<220> FEATURE:
<223> OTHER INFORMATION: binding peptide

<400> SEQUENCE: 102

Ala Gly Asn Tyr Met Phe Leu Gly Tyr Arg Ser Leu
 1               5                  10

<210> SEQ ID NO 103
<211> LENGTH: 12
<212> TYPE: PRT
<213> ORGANISM: Artificial Sequence
```

```
<220> FEATURE:
<223> OTHER INFORMATION: binding peptide

<400> SEQUENCE: 103

Thr Ala Thr His Leu Ser Pro Gly Ala Trp Arg Pro
 1               5                  10

<210> SEQ ID NO 104
<211> LENGTH: 12
<212> TYPE: PRT
<213> ORGANISM: Artificial Sequence
<220> FEATURE:
<223> OTHER INFORMATION: binding peptide

<400> SEQUENCE: 104

Tyr His Thr Pro Ser Thr Gly Gly Ala Ser Pro Val
 1               5                  10

<210> SEQ ID NO 105
<211> LENGTH: 12
<212> TYPE: PRT
<213> ORGANISM: Artificial Sequence
<220> FEATURE:
<223> OTHER INFORMATION: binding peptide

<400> SEQUENCE: 105

Ser Ser Asp Val Pro Gln Ala Ala Arg Asn Asp Ala
 1               5                  10

<210> SEQ ID NO 106
<211> LENGTH: 12
<212> TYPE: PRT
<213> ORGANISM: Artificial Sequence
<220> FEATURE:
<223> OTHER INFORMATION: binding peptide

<400> SEQUENCE: 106

Leu Ser Lys Lys Ile Thr Thr Asp Glu Trp Phe Ala
 1               5                  10

<210> SEQ ID NO 107
<211> LENGTH: 12
<212> TYPE: PRT
<213> ORGANISM: Artificial Sequence
<220> FEATURE:
<223> OTHER INFORMATION: binding peptide

<400> SEQUENCE: 107

Ser Gln Ile Lys His Pro His Ala Ser Ser Ser Ile
 1               5                  10

<210> SEQ ID NO 108
<211> LENGTH: 12
<212> TYPE: PRT
<213> ORGANISM: Artificial Sequence
<220> FEATURE:
<223> OTHER INFORMATION: binding peptide

<400> SEQUENCE: 108

Ser Met Gln Leu Gln Leu Ile Pro Ser Thr Pro Thr
 1               5                  10

<210> SEQ ID NO 109
<211> LENGTH: 12
<212> TYPE: PRT
<213> ORGANISM: Artificial Sequence
<220> FEATURE:
```

```
<223> OTHER INFORMATION: binding peptide

<400> SEQUENCE: 109

Tyr Asp His Asn Tyr Thr Met Asn Asn Ala Leu Asn
1               5                   10

<210> SEQ ID NO 110
<211> LENGTH: 12
<212> TYPE: PRT
<213> ORGANISM: Artificial Sequence
<220> FEATURE:
<223> OTHER INFORMATION: binding peptide

<400> SEQUENCE: 110

Asn Ala Phe Glu Thr Gln Arg Leu Ala Gln Leu Gly
1               5                   10

<210> SEQ ID NO 111
<211> LENGTH: 12
<212> TYPE: PRT
<213> ORGANISM: Artificial Sequence
<220> FEATURE:
<223> OTHER INFORMATION: binding peptide

<400> SEQUENCE: 111

Ala Gln Ala Ser Arg Ile Asn Thr Tyr Pro Pro Thr
1               5                   10

<210> SEQ ID NO 112
<211> LENGTH: 12
<212> TYPE: PRT
<213> ORGANISM: Artificial Sequence
<220> FEATURE:
<223> OTHER INFORMATION: binding peptide

<400> SEQUENCE: 112

His Gln Thr Ser Asn Gly Pro Thr Pro Leu Val Pro
1               5                   10

<210> SEQ ID NO 113
<211> LENGTH: 12
<212> TYPE: PRT
<213> ORGANISM: Artificial Sequence
<220> FEATURE:
<223> OTHER INFORMATION: binding peptide

<400> SEQUENCE: 113

Thr Phe Thr Pro Tyr Ala Tyr Gln Ser Asn Met Ser
1               5                   10

<210> SEQ ID NO 114
<211> LENGTH: 12
<212> TYPE: PRT
<213> ORGANISM: Artificial Sequence
<220> FEATURE:
<223> OTHER INFORMATION: binding peptide

<400> SEQUENCE: 114

Thr Thr Leu Thr Tyr Asn Trp Lys Ser Ala His Gln
1               5                   10

<210> SEQ ID NO 115
<211> LENGTH: 12
<212> TYPE: PRT
<213> ORGANISM: Artificial Sequence
<220> FEATURE:
<223> OTHER INFORMATION: binding peptide
```

<400> SEQUENCE: 115

Glu Met Val Ser Lys Lys Thr Leu Thr Ser Val Leu
1               5                   10

<210> SEQ ID NO 116
<211> LENGTH: 12
<212> TYPE: PRT
<213> ORGANISM: Artificial Sequence
<220> FEATURE:
<223> OTHER INFORMATION: binding peptide

<400> SEQUENCE: 116

Glu Leu Val Lys Asn Pro Tyr Thr Arg Ser Leu Thr
1               5                   10

<210> SEQ ID NO 117
<211> LENGTH: 12
<212> TYPE: PRT
<213> ORGANISM: Artificial Sequence
<220> FEATURE:
<223> OTHER INFORMATION: binding peptide

<400> SEQUENCE: 117

Leu Pro Pro Gln Pro Pro Phe Ile Thr Thr Met Leu
1               5                   10

<210> SEQ ID NO 118
<211> LENGTH: 12
<212> TYPE: PRT
<213> ORGANISM: Artificial Sequence
<220> FEATURE:
<223> OTHER INFORMATION: binding peptide

<400> SEQUENCE: 118

Ser Pro Thr Thr Leu Val Gln Met Pro Trp Pro Arg
1               5                   10

<210> SEQ ID NO 119
<211> LENGTH: 12
<212> TYPE: PRT
<213> ORGANISM: Artificial Sequence
<220> FEATURE:
<223> OTHER INFORMATION: binding peptide

<400> SEQUENCE: 119

Ser Ala Gln Asn Gly Val Ile Ser Tyr Asp Leu Gly
1               5                   10

<210> SEQ ID NO 120
<211> LENGTH: 12
<212> TYPE: PRT
<213> ORGANISM: Artificial Sequence
<220> FEATURE:
<223> OTHER INFORMATION: binding peptide

<400> SEQUENCE: 120

Gln Ile Trp His Pro His Asn Tyr Pro Gly Ser Leu
1               5                   10

<210> SEQ ID NO 121
<211> LENGTH: 12
<212> TYPE: PRT
<213> ORGANISM: Artificial Sequence
<220> FEATURE:
<223> OTHER INFORMATION: binding peptide -continued

```
<400> SEQUENCE: 121

Thr Asn Gln Leu His Arg Thr His Pro Ser Gly Gln
1               5                   10

<210> SEQ ID NO 122
<211> LENGTH: 12
<212> TYPE: PRT
<213> ORGANISM: Artificial Sequence
<220> FEATURE:
<223> OTHER INFORMATION: binding peptide

<400> SEQUENCE: 122

Asn Asp His Arg Glu Val Arg Thr Arg Leu Phe Leu
1               5                   10

<210> SEQ ID NO 123
<211> LENGTH: 12
<212> TYPE: PRT
<213> ORGANISM: Artificial Sequence
<220> FEATURE:
<223> OTHER INFORMATION: binding peptide

<400> SEQUENCE: 123

His Ser Phe Arg Val Thr Ser Asn Leu Ser Pro Pro
1               5                   10

<210> SEQ ID NO 124
<211> LENGTH: 12
<212> TYPE: PRT
<213> ORGANISM: Artificial Sequence
<220> FEATURE:
<223> OTHER INFORMATION: binding peptide

<400> SEQUENCE: 124

Tyr Asn Thr Ser Ile Met Gln Lys Ala Val Ser Pro
1               5                   10

<210> SEQ ID NO 125
<211> LENGTH: 12
<212> TYPE: PRT
<213> ORGANISM: Artificial Sequence
<220> FEATURE:
<223> OTHER INFORMATION: binding peptide

<400> SEQUENCE: 125

Ala Ser Pro Asn Thr His Thr Pro Ala Ala Arg Ala
1               5                   10

<210> SEQ ID NO 126
<211> LENGTH: 12
<212> TYPE: PRT
<213> ORGANISM: Artificial Sequence
<220> FEATURE:
<223> OTHER INFORMATION: binding peptide

<400> SEQUENCE: 126

Thr Leu Tyr Gln Asp Gln Lys Gln Lys Gln Arg Phe
1               5                   10

<210> SEQ ID NO 127
<211> LENGTH: 12
<212> TYPE: PRT
<213> ORGANISM: Artificial Sequence
<220> FEATURE:
<223> OTHER INFORMATION: binding peptide

<400> SEQUENCE: 127
```

```
Glu Ile Leu Tyr Met Pro Pro Ser Thr His Ala Leu
 1               5                   10
```

<210> SEQ ID NO 128
<211> LENGTH: 12
<212> TYPE: PRT
<213> ORGANISM: Artificial Sequence
<220> FEATURE:
<223> OTHER INFORMATION: binding peptide

<400> SEQUENCE: 128

```
Thr Pro Phe Ile Tyr Leu Lys Ser Ser Ser Leu Pro
 1               5                   10
```

<210> SEQ ID NO 129
<211> LENGTH: 12
<212> TYPE: PRT
<213> ORGANISM: Artificial Sequence
<220> FEATURE:
<223> OTHER INFORMATION: binding peptide

<400> SEQUENCE: 129

```
Asp Ile Pro Ser Phe Glu Thr Ile Pro Pro Arg Pro
 1               5                   10
```

<210> SEQ ID NO 130
<211> LENGTH: 12
<212> TYPE: PRT
<213> ORGANISM: Artificial Sequence
<220> FEATURE:
<223> OTHER INFORMATION: binding peptide

<400> SEQUENCE: 130

```
Gly His Arg Pro His Ala Ile Lys Pro Pro Pro Pro
 1               5                   10
```

<210> SEQ ID NO 131
<211> LENGTH: 12
<212> TYPE: PRT
<213> ORGANISM: Artificial Sequence
<220> FEATURE:
<223> OTHER INFORMATION: binding peptide

<400> SEQUENCE: 131

```
Ser Asp Tyr Ser Ser Ala Ala Thr Tyr Tyr Gly His
 1               5                   10
```

<210> SEQ ID NO 132
<211> LENGTH: 12
<212> TYPE: PRT
<213> ORGANISM: Artificial Sequence
<220> FEATURE:
<223> OTHER INFORMATION: binding peptide

<400> SEQUENCE: 132

```
Ser Ser Thr Ser Pro Leu Leu Pro His Met Leu Leu
 1               5                   10
```

<210> SEQ ID NO 133
<211> LENGTH: 12
<212> TYPE: PRT
<213> ORGANISM: Artificial Sequence
<220> FEATURE:
<223> OTHER INFORMATION: binding peptide

<400> SEQUENCE: 133

```
Thr Ser Glu His Thr Leu Ala Ser Lys Tyr Gln Ser
 1               5                  10
```

<210> SEQ ID NO 134
<211> LENGTH: 12
<212> TYPE: PRT
<213> ORGANISM: Artificial Sequence
<220> FEATURE:
<223> OTHER INFORMATION: binding peptide

<400> SEQUENCE: 134

```
Ser His Gly Ile Ala Thr Ser Glu Thr Thr Ser Asn
 1               5                  10
```

<210> SEQ ID NO 135
<211> LENGTH: 12
<212> TYPE: PRT
<213> ORGANISM: Artificial Sequence
<220> FEATURE:
<223> OTHER INFORMATION: binding peptide

<400> SEQUENCE: 135

```
Met Asn Pro Ser Ser Ser Gln His Lys Asn Ser His
 1               5                  10
```

<210> SEQ ID NO 136
<211> LENGTH: 12
<212> TYPE: PRT
<213> ORGANISM: Artificial Sequence
<220> FEATURE:
<223> OTHER INFORMATION: binding peptide

<400> SEQUENCE: 136

```
Pro Trp Ala Ser Ile Thr Pro Pro Pro Leu Leu Arg
 1               5                  10
```

<210> SEQ ID NO 137
<211> LENGTH: 12
<212> TYPE: PRT
<213> ORGANISM: Artificial Sequence
<220> FEATURE:
<223> OTHER INFORMATION: binding peptide

<400> SEQUENCE: 137

```
Gln Asn Leu Gln Pro Pro Gln Gly Phe Thr Leu Gly
 1               5                  10
```

<210> SEQ ID NO 138
<211> LENGTH: 12
<212> TYPE: PRT
<213> ORGANISM: Artificial Sequence
<220> FEATURE:
<223> OTHER INFORMATION: binding peptide

<400> SEQUENCE: 138

```
Thr Thr Ser Phe Ser Glu Gly Ile Leu Ile Arg Ser
 1               5                  10
```

<210> SEQ ID NO 139
<211> LENGTH: 12
<212> TYPE: PRT
<213> ORGANISM: Artificial Sequence
<220> FEATURE:
<223> OTHER INFORMATION: binding peptide

<400> SEQUENCE: 139

```
Asn Val Pro Thr Ser Asn Thr His Phe Gly Leu His
```

<210> SEQ ID NO 140
<211> LENGTH: 12
<212> TYPE: PRT
<213> ORGANISM: Artificial Sequence
<220> FEATURE:
<223> OTHER INFORMATION: binding peptide

<400> SEQUENCE: 140

Thr Gly Ser Met Glu Leu Trp Thr Leu Gln Thr Gln
1               5                   10

<210> SEQ ID NO 141
<211> LENGTH: 12
<212> TYPE: PRT
<213> ORGANISM: Artificial Sequence
<220> FEATURE:
<223> OTHER INFORMATION: binding peptide

<400> SEQUENCE: 141

Ser Pro Ala Arg Ser Thr Val Gly Pro Tyr Glu Leu
1               5                   10

<210> SEQ ID NO 142
<211> LENGTH: 12
<212> TYPE: PRT
<213> ORGANISM: Artificial Sequence
<220> FEATURE:
<223> OTHER INFORMATION: binding peptide

<400> SEQUENCE: 142

Ser His Ala Ile Thr Ala Thr His Leu Glu Pro Ser
1               5                   10

<210> SEQ ID NO 143
<211> LENGTH: 12
<212> TYPE: PRT
<213> ORGANISM: Artificial Sequence
<220> FEATURE:
<223> OTHER INFORMATION: binding peptide

<400> SEQUENCE: 143

Leu Gln Leu Gln Leu Leu Pro Tyr Ala Phe Pro Val
1               5                   10

<210> SEQ ID NO 144
<211> LENGTH: 12
<212> TYPE: PRT
<213> ORGANISM: Artificial Sequence
<220> FEATURE:
<223> OTHER INFORMATION: binding peptide

<400> SEQUENCE: 144

Asn Asn Leu Ala Phe Thr Pro Ser Gly Thr Leu Arg
1               5                   10

<210> SEQ ID NO 145
<211> LENGTH: 12
<212> TYPE: PRT
<213> ORGANISM: Artificial Sequence
<220> FEATURE:
<223> OTHER INFORMATION: binding peptide

<400> SEQUENCE: 145

His Phe Ala Tyr Thr Lys Pro Met Arg Ile Pro Gln
1               5                   10

<210> SEQ ID NO 146
<211> LENGTH: 12
<212> TYPE: PRT
<213> ORGANISM: Artificial Sequence
<220> FEATURE:
<223> OTHER INFORMATION: binding peptide

<400> SEQUENCE: 146

Ser Ser Trp Leu His Asp Leu Pro Val Leu Pro Leu
1               5                   10

<210> SEQ ID NO 147
<211> LENGTH: 12
<212> TYPE: PRT
<213> ORGANISM: Artificial Sequence
<220> FEATURE:
<223> OTHER INFORMATION: binding peptide

<400> SEQUENCE: 147

Ser Val Thr Tyr Gln Asn Tyr Gly Met Asn Thr Met
1               5                   10

<210> SEQ ID NO 148
<211> LENGTH: 12
<212> TYPE: PRT
<213> ORGANISM: Artificial Sequence
<220> FEATURE:
<223> OTHER INFORMATION: binding peptide

<400> SEQUENCE: 148

Tyr Ala His Ala Gly Lys Thr Thr Phe Leu Leu Gly
1               5                   10

<210> SEQ ID NO 149
<211> LENGTH: 12
<212> TYPE: PRT
<213> ORGANISM: Artificial Sequence
<220> FEATURE:
<223> OTHER INFORMATION: binding peptide

<400> SEQUENCE: 149

His Pro Pro Ser Leu Pro Asn Asn Val Val His Pro
1               5                   10

<210> SEQ ID NO 150
<211> LENGTH: 12
<212> TYPE: PRT
<213> ORGANISM: Artificial Sequence
<220> FEATURE:
<223> OTHER INFORMATION: binding peptide

<400> SEQUENCE: 150

Ser Ser Lys Asn Pro Leu Ala Asp Asn Pro Arg Gln
1               5                   10

<210> SEQ ID NO 151
<211> LENGTH: 12
<212> TYPE: PRT
<213> ORGANISM: Artificial Sequence
<220> FEATURE:
<223> OTHER INFORMATION: binding peptide

<400> SEQUENCE: 151

His Leu Ser Arg Phe Glu Ser Leu Met His Leu Met
1               5                   10

```
<210> SEQ ID NO 152
<211> LENGTH: 12
<212> TYPE: PRT
<213> ORGANISM: Artificial Sequence
<220> FEATURE:
<223> OTHER INFORMATION: binding peptide

<400> SEQUENCE: 152

Trp Leu His Leu Pro Gly Ser Ala Gln Asn His Leu
 1               5                  10

<210> SEQ ID NO 153
<211> LENGTH: 12
<212> TYPE: PRT
<213> ORGANISM: Artificial Sequence
<220> FEATURE:
<223> OTHER INFORMATION: binding peptide

<400> SEQUENCE: 153

Arg Asn Arg Pro His Ile Ile Arg Pro Pro Pro Pro
 1               5                  10

<210> SEQ ID NO 154
<211> LENGTH: 12
<212> TYPE: PRT
<213> ORGANISM: Artificial Sequence
<220> FEATURE:
<223> OTHER INFORMATION: binding peptide

<400> SEQUENCE: 154

Thr Lys Asn Trp Met Pro His Gln Asp Ala Pro Leu
 1               5                  10

<210> SEQ ID NO 155
<211> LENGTH: 12
<212> TYPE: PRT
<213> ORGANISM: Artificial Sequence
<220> FEATURE:
<223> OTHER INFORMATION: binding peptide

<400> SEQUENCE: 155

Gln Asn Gln Leu Asp Met Thr Lys Leu Thr Met Leu
 1               5                  10

<210> SEQ ID NO 156
<211> LENGTH: 12
<212> TYPE: PRT
<213> ORGANISM: Artificial Sequence
<220> FEATURE:
<223> OTHER INFORMATION: binding peptide

<400> SEQUENCE: 156

Asn Pro Pro Pro Pro Thr Pro Pro Ala Pro Pro
 1               5                  10

<210> SEQ ID NO 157
<211> LENGTH: 12
<212> TYPE: PRT
<213> ORGANISM: Artificial Sequence
<220> FEATURE:
<223> OTHER INFORMATION: binding peptide

<400> SEQUENCE: 157

Ser Tyr Thr Gln Ile Leu Ala His Pro Lys His Ala
 1               5                  10
```

```
<210> SEQ ID NO 158
<211> LENGTH: 12
<212> TYPE: PRT
<213> ORGANISM: Artificial Sequence
<220> FEATURE:
<223> OTHER INFORMATION: binding peptide

<400> SEQUENCE: 158

Gln Thr Gly Gln Ala His Gln Gln Pro Ser Ala Thr
 1               5                  10

<210> SEQ ID NO 159
<211> LENGTH: 12
<212> TYPE: PRT
<213> ORGANISM: Artificial Sequence
<220> FEATURE:
<223> OTHER INFORMATION: binding peptide

<400> SEQUENCE: 159

Asn Ile Pro Tyr Leu Ala Met Pro Thr Lys Arg Met
 1               5                  10

<210> SEQ ID NO 160
<211> LENGTH: 12
<212> TYPE: PRT
<213> ORGANISM: Artificial Sequence
<220> FEATURE:
<223> OTHER INFORMATION: binding peptide

<400> SEQUENCE: 160

Leu Arg Ser Asp Gln Tyr Phe His His Thr Thr Leu
 1               5                  10

<210> SEQ ID NO 161
<211> LENGTH: 12
<212> TYPE: PRT
<213> ORGANISM: Artificial Sequence
<220> FEATURE:
<223> OTHER INFORMATION: binding peptide

<400> SEQUENCE: 161

His Leu Tyr Arg Asn Asn Asp Thr Phe Ala Pro Arg
 1               5                  10

<210> SEQ ID NO 162
<211> LENGTH: 12
<212> TYPE: PRT
<213> ORGANISM: Artificial Sequence
<220> FEATURE:
<223> OTHER INFORMATION: binding peptide

<400> SEQUENCE: 162

Gly Ser Val Gly Tyr Met Arg Pro Pro Lys Val Tyr
 1               5                  10

<210> SEQ ID NO 163
<211> LENGTH: 12
<212> TYPE: PRT
<213> ORGANISM: Artificial Sequence
<220> FEATURE:
<223> OTHER INFORMATION: binding peptide

<400> SEQUENCE: 163

Leu Pro Ala Gln Met Thr Pro Val Ser Val Val Arg
 1               5                  10

<210> SEQ ID NO 164
```

-continued

```
<211> LENGTH: 12
<212> TYPE: PRT
<213> ORGANISM: Artificial Sequence
<220> FEATURE:
<223> OTHER INFORMATION: binding peptide

<400> SEQUENCE: 164

Gln Gln Leu Ile Asn Tyr Ser Met Pro Leu Pro Met
1               5                   10

<210> SEQ ID NO 165
<211> LENGTH: 12
<212> TYPE: PRT
<213> ORGANISM: Artificial Sequence
<220> FEATURE:
<223> OTHER INFORMATION: binding peptide

<400> SEQUENCE: 165

Tyr Pro Thr Phe Ser Tyr Val Ser Pro Glu Val Thr
1               5                   10

<210> SEQ ID NO 166
<211> LENGTH: 12
<212> TYPE: PRT
<213> ORGANISM: Artificial Sequence
<220> FEATURE:
<223> OTHER INFORMATION: binding peptide

<400> SEQUENCE: 166

Thr Tyr Thr Ser Gln Ser Arg Ser Pro Ala Asp Asp
1               5                   10

<210> SEQ ID NO 167
<211> LENGTH: 12
<212> TYPE: PRT
<213> ORGANISM: Artificial Sequence
<220> FEATURE:
<223> OTHER INFORMATION: binding peptide

<400> SEQUENCE: 167

Ala Tyr Trp Asp Phe Ile Gln Ala Lys Gln Ala Met
1               5                   10

<210> SEQ ID NO 168
<211> LENGTH: 12
<212> TYPE: PRT
<213> ORGANISM: Artificial Sequence
<220> FEATURE:
<223> OTHER INFORMATION: binding peptide

<400> SEQUENCE: 168

Gly Leu Gln Thr Ile Asp Leu Asn Leu Tyr Asn Ala
1               5                   10

<210> SEQ ID NO 169
<211> LENGTH: 12
<212> TYPE: PRT
<213> ORGANISM: Artificial Sequence
<220> FEATURE:
<223> OTHER INFORMATION: binding peptide

<400> SEQUENCE: 169

Thr Ile Met His Thr Thr Val Pro Gly His Leu Gln
1               5                   10

<210> SEQ ID NO 170
<211> LENGTH: 12
```

```
<212> TYPE: PRT
<213> ORGANISM: Artificial Sequence
<220> FEATURE:
<223> OTHER INFORMATION: binding peptide

<400> SEQUENCE: 170

Ile Thr Gln Thr Arg Phe Ile Ala Ala Pro Leu His
1               5                   10

<210> SEQ ID NO 171
<211> LENGTH: 12
<212> TYPE: PRT
<213> ORGANISM: Artificial Sequence
<220> FEATURE:
<223> OTHER INFORMATION: binding peptide

<400> SEQUENCE: 171

His Val Leu Arg His Pro Gly Asn Pro Asn Thr Phe
1               5                   10

<210> SEQ ID NO 172
<211> LENGTH: 12
<212> TYPE: PRT
<213> ORGANISM: Artificial Sequence
<220> FEATURE:
<223> OTHER INFORMATION: binding peptide

<400> SEQUENCE: 172

Ala His His Asp Asp Lys His Ser Ala Pro Asp Thr
1               5                   10

<210> SEQ ID NO 173
<211> LENGTH: 12
<212> TYPE: PRT
<213> ORGANISM: Artificial Sequence
<220> FEATURE:
<223> OTHER INFORMATION: binding peptide

<400> SEQUENCE: 173

Asp Pro Ser Asn Lys Arg Tyr Pro Gln Ser Tyr Lys
1               5                   10

<210> SEQ ID NO 174
<211> LENGTH: 12
<212> TYPE: PRT
<213> ORGANISM: Artificial Sequence
<220> FEATURE:
<223> OTHER INFORMATION: binding peptide

<400> SEQUENCE: 174

Leu Asn Ala Asn Leu Pro Ala Asn Ser Val Leu Ala
1               5                   10

<210> SEQ ID NO 175
<211> LENGTH: 12
<212> TYPE: PRT
<213> ORGANISM: Artificial Sequence
<220> FEATURE:
<223> OTHER INFORMATION: binding peptide

<400> SEQUENCE: 175

Asn Ile Asn Lys His Tyr Phe Gln Ser Pro Ile Met
1               5                   10

<210> SEQ ID NO 176
<211> LENGTH: 12
<212> TYPE: PRT
```

```
<213> ORGANISM: Artificial Sequence
<220> FEATURE:
<223> OTHER INFORMATION: binding peptide

<400> SEQUENCE: 176

Thr Gly Met Lys Ala Pro Ser Gly Ile Tyr Thr Gly
 1               5                  10

<210> SEQ ID NO 177
<211> LENGTH: 12
<212> TYPE: PRT
<213> ORGANISM: Artificial Sequence
<220> FEATURE:
<223> OTHER INFORMATION: binding peptide

<400> SEQUENCE: 177

Gln Val Asn Phe Ser Asn His Ser Ser Arg Ser Pro
 1               5                  10

<210> SEQ ID NO 178
<211> LENGTH: 12
<212> TYPE: PRT
<213> ORGANISM: Artificial Sequence
<220> FEATURE:
<223> OTHER INFORMATION: binding peptide

<400> SEQUENCE: 178

Asn Ser Pro Met Gln Ala Leu His Asp Pro His Ser
 1               5                  10

<210> SEQ ID NO 179
<211> LENGTH: 12
<212> TYPE: PRT
<213> ORGANISM: Artificial Sequence
<220> FEATURE:
<223> OTHER INFORMATION: binding peptide

<400> SEQUENCE: 179

Val Glu Asn Leu Thr Gln Pro Pro Pro Pro Phe Gly
 1               5                  10

<210> SEQ ID NO 180
<211> LENGTH: 12
<212> TYPE: PRT
<213> ORGANISM: Artificial Sequence
<220> FEATURE:
<223> OTHER INFORMATION: binding peptide

<400> SEQUENCE: 180

Gln Thr Leu Asn Met Glu Pro Arg Ser Tyr Ser Asn
 1               5                  10

<210> SEQ ID NO 181
<211> LENGTH: 12
<212> TYPE: PRT
<213> ORGANISM: Artificial Sequence
<220> FEATURE:
<223> OTHER INFORMATION: binding peptide

<400> SEQUENCE: 181

Ile Ala Pro Gly Gly Ser Ile Lys Ala Pro Pro Arg
 1               5                  10

<210> SEQ ID NO 182
<211> LENGTH: 12
<212> TYPE: PRT
<213> ORGANISM: Artificial Sequence
```

```
<220> FEATURE:
<223> OTHER INFORMATION: binding peptide

<400> SEQUENCE: 182

Asp Ser Leu Thr Ser Asn Ser Gln Pro Pro Ser Ser
 1               5                  10

<210> SEQ ID NO 183
<211> LENGTH: 12
<212> TYPE: PRT
<213> ORGANISM: Artificial Sequence
<220> FEATURE:
<223> OTHER INFORMATION: binding peptide

<400> SEQUENCE: 183

Thr Pro Pro Ser Leu Tyr Tyr Leu Gly Pro Leu Pro
 1               5                  10

<210> SEQ ID NO 184
<211> LENGTH: 12
<212> TYPE: PRT
<213> ORGANISM: Artificial Sequence
<220> FEATURE:
<223> OTHER INFORMATION: binding peptide

<400> SEQUENCE: 184

Gln Pro Met Leu Phe Gly Leu Arg Gly Ala Phe Ala
 1               5                  10

<210> SEQ ID NO 185
<211> LENGTH: 12
<212> TYPE: PRT
<213> ORGANISM: Artificial Sequence
<220> FEATURE:
<223> OTHER INFORMATION: binding peptide

<400> SEQUENCE: 185

His Asn Ala Met Leu Pro Gln Tyr Leu Leu Leu Ser
 1               5                  10

<210> SEQ ID NO 186
<211> LENGTH: 12
<212> TYPE: PRT
<213> ORGANISM: Artificial Sequence
<220> FEATURE:
<223> OTHER INFORMATION: binding peptide

<400> SEQUENCE: 186

Ser Phe Asn Tyr Ala Thr Phe Pro Leu Val Pro Leu
 1               5                  10

<210> SEQ ID NO 187
<211> LENGTH: 12
<212> TYPE: PRT
<213> ORGANISM: Artificial Sequence
<220> FEATURE:
<223> OTHER INFORMATION: binding peptide

<400> SEQUENCE: 187

Leu Met Ala Arg Leu Pro Asp Thr Tyr Thr Gln Val
 1               5                  10

<210> SEQ ID NO 188
<211> LENGTH: 12
<212> TYPE: PRT
<213> ORGANISM: Artificial Sequence
<220> FEATURE:
```

<223> OTHER INFORMATION: binding peptide

<400> SEQUENCE: 188

Thr Ala Pro Ile Ala Ser Leu Thr Tyr Pro Leu Ile
1               5                   10

<210> SEQ ID NO 189
<211> LENGTH: 12
<212> TYPE: PRT
<213> ORGANISM: Artificial Sequence
<220> FEATURE:
<223> OTHER INFORMATION: binding peptide

<400> SEQUENCE: 189

Thr His His Phe Gln Met Pro Pro Pro Pro Met Leu
1               5                   10

<210> SEQ ID NO 190
<211> LENGTH: 12
<212> TYPE: PRT
<213> ORGANISM: Artificial Sequence
<220> FEATURE:
<223> OTHER INFORMATION: binding peptide

<400> SEQUENCE: 190

Met Asp Leu Gln Pro Pro Ser Ser Pro Arg Ser Thr
1               5                   10

<210> SEQ ID NO 191
<211> LENGTH: 12
<212> TYPE: PRT
<213> ORGANISM: Artificial Sequence
<220> FEATURE:
<223> OTHER INFORMATION: binding peptide

<400> SEQUENCE: 191

Lys Met Met Ser Asn Ser Leu Thr Leu Arg Leu Pro
1               5                   10

<210> SEQ ID NO 192
<211> LENGTH: 12
<212> TYPE: PRT
<213> ORGANISM: Artificial Sequence
<220> FEATURE:
<223> OTHER INFORMATION: binding peptide

<400> SEQUENCE: 192

Thr Pro Pro Gln Glu Leu Ile Thr Ala Ser Arg Ala
1               5                   10

<210> SEQ ID NO 193
<211> LENGTH: 12
<212> TYPE: PRT
<213> ORGANISM: Artificial Sequence
<220> FEATURE:
<223> OTHER INFORMATION: binding peptide

<400> SEQUENCE: 193

Tyr Asn Lys Pro Leu Leu Gln Ser Gln Thr Leu Leu
1               5                   10

<210> SEQ ID NO 194
<211> LENGTH: 12
<212> TYPE: PRT
<213> ORGANISM: Artificial Sequence
<220> FEATURE:
<223> OTHER INFORMATION: binding peptide

```
<400> SEQUENCE: 194

His Ser Leu Ala Gly Ile Ala Arg Met Leu Met Glu
1               5                   10

<210> SEQ ID NO 195
<211> LENGTH: 7
<212> TYPE: PRT
<213> ORGANISM: Artificial Sequence
<220> FEATURE:
<223> OTHER INFORMATION: binding peptide

<400> SEQUENCE: 195

Ser Ala Ala Gln Leu Asn Met
1               5

<210> SEQ ID NO 196
<211> LENGTH: 7
<212> TYPE: PRT
<213> ORGANISM: Artificial Sequence
<220> FEATURE:
<223> OTHER INFORMATION: binding peptide

<400> SEQUENCE: 196

Ser Leu His Gln Ser Asn Tyr
1               5

<210> SEQ ID NO 197
<211> LENGTH: 7
<212> TYPE: PRT
<213> ORGANISM: Artificial Sequence
<220> FEATURE:
<223> OTHER INFORMATION: binding peptide

<400> SEQUENCE: 197

Leu Gly Pro Pro Pro Phe Arg
1               5

<210> SEQ ID NO 198
<211> LENGTH: 7
<212> TYPE: PRT
<213> ORGANISM: Artificial Sequence
<220> FEATURE:
<223> OTHER INFORMATION: binding peptide

<400> SEQUENCE: 198

Thr Thr Ala Pro Pro Thr Thr
1               5

<210> SEQ ID NO 199
<211> LENGTH: 7
<212> TYPE: PRT
<213> ORGANISM: Artificial Sequence
<220> FEATURE:
<223> OTHER INFORMATION: binding peptide

<400> SEQUENCE: 199

Pro Ser His Gln Gln Gln Val
1               5

<210> SEQ ID NO 200
<211> LENGTH: 7
<212> TYPE: PRT
<213> ORGANISM: Artificial Sequence
<220> FEATURE:
<223> OTHER INFORMATION: binding peptide
```

```
<400> SEQUENCE: 200

Pro Thr Phe Ile Lys Ser Asn
1               5

<210> SEQ ID NO 201
<211> LENGTH: 7
<212> TYPE: PRT
<213> ORGANISM: Artificial Sequence
<220> FEATURE:
<223> OTHER INFORMATION: binding peptide

<400> SEQUENCE: 201

Ser Tyr Pro Leu Ala Ser Arg
1               5

<210> SEQ ID NO 202
<211> LENGTH: 7
<212> TYPE: PRT
<213> ORGANISM: Artificial Sequence
<220> FEATURE:
<223> OTHER INFORMATION: binding peptide

<400> SEQUENCE: 202

Ser Lys Ile Ser Val Thr Leu
1               5

<210> SEQ ID NO 203
<211> LENGTH: 7
<212> TYPE: PRT
<213> ORGANISM: Artificial Sequence
<220> FEATURE:
<223> OTHER INFORMATION: binding peptide

<400> SEQUENCE: 203

Thr Asn Ala Ser Pro Leu His
1               5

<210> SEQ ID NO 204
<211> LENGTH: 7
<212> TYPE: PRT
<213> ORGANISM: Artificial Sequence
<220> FEATURE:
<223> OTHER INFORMATION: binding peptide

<400> SEQUENCE: 204

Pro Leu Asn Pro Asn Asn Met
1               5

<210> SEQ ID NO 205
<211> LENGTH: 7
<212> TYPE: PRT
<213> ORGANISM: Artificial Sequence
<220> FEATURE:
<223> OTHER INFORMATION: binding peptide

<400> SEQUENCE: 205

Ser Gly Arg Pro Tyr Glu Thr
1               5

<210> SEQ ID NO 206
<211> LENGTH: 7
<212> TYPE: PRT
<213> ORGANISM: Artificial Sequence
<220> FEATURE:
<223> OTHER INFORMATION: binding peptide

<400> SEQUENCE: 206
```

```
Gly Trp Thr Met Ala Gln Arg
 1               5
```

<210> SEQ ID NO 207
<211> LENGTH: 7
<212> TYPE: PRT
<213> ORGANISM: Artificial Sequence
<220> FEATURE:
<223> OTHER INFORMATION: binding peptide

<400> SEQUENCE: 207

```
Lys Leu Asn Asp Met Leu Leu
 1               5
```

<210> SEQ ID NO 208
<211> LENGTH: 7
<212> TYPE: PRT
<213> ORGANISM: Artificial Sequence
<220> FEATURE:
<223> OTHER INFORMATION: binding peptide

<400> SEQUENCE: 208

```
Arg Thr Thr Pro Pro Trp Met
 1               5
```

<210> SEQ ID NO 209
<211> LENGTH: 7
<212> TYPE: PRT
<213> ORGANISM: Artificial Sequence
<220> FEATURE:
<223> OTHER INFORMATION: binding peptide

<400> SEQUENCE: 209

```
Tyr Gln Ser Met Ser Tyr Ser
 1               5
```

<210> SEQ ID NO 210
<211> LENGTH: 7
<212> TYPE: PRT
<213> ORGANISM: Artificial Sequence
<220> FEATURE:
<223> OTHER INFORMATION: binding peptide

<400> SEQUENCE: 210

```
Thr Ser Gly Pro Ser Pro Met
 1               5
```

<210> SEQ ID NO 211
<211> LENGTH: 7
<212> TYPE: PRT
<213> ORGANISM: Artificial Sequence
<220> FEATURE:
<223> OTHER INFORMATION: binding peptide

<400> SEQUENCE: 211

```
His Ala Lys Ala Pro Ser Thr
 1               5
```

<210> SEQ ID NO 212
<211> LENGTH: 7
<212> TYPE: PRT
<213> ORGANISM: Artificial Sequence
<220> FEATURE:
<223> OTHER INFORMATION: binding peptide

<400> SEQUENCE: 212

-continued

Pro His Ser Arg Gly Leu Ala
1               5

<210> SEQ ID NO 213
<211> LENGTH: 7
<212> TYPE: PRT
<213> ORGANISM: Artificial Sequence
<220> FEATURE:
<223> OTHER INFORMATION: binding peptide

<400> SEQUENCE: 213

Gln Gln Ser Trp Pro Pro Phe
1               5

<210> SEQ ID NO 214
<211> LENGTH: 7
<212> TYPE: PRT
<213> ORGANISM: Artificial Sequence
<220> FEATURE:
<223> OTHER INFORMATION: binding peptide

<400> SEQUENCE: 214

Pro Asn Asn Ser Thr Pro Val
1               5

<210> SEQ ID NO 215
<211> LENGTH: 7
<212> TYPE: PRT
<213> ORGANISM: Artificial Sequence
<220> FEATURE:
<223> OTHER INFORMATION: binding peptide

<400> SEQUENCE: 215

Thr Thr Thr Trp Trp His Val
1               5

<210> SEQ ID NO 216
<211> LENGTH: 7
<212> TYPE: PRT
<213> ORGANISM: Artificial Sequence
<220> FEATURE:
<223> OTHER INFORMATION: binding peptide

<400> SEQUENCE: 216

Phe Ser Gln Ser Asp Pro Trp
1               5

<210> SEQ ID NO 217
<211> LENGTH: 7
<212> TYPE: PRT
<213> ORGANISM: Artificial Sequence
<220> FEATURE:
<223> OTHER INFORMATION: binding peptide

<400> SEQUENCE: 217

Lys Pro Thr Val Asp Arg Asn
1               5

<210> SEQ ID NO 218
<211> LENGTH: 7
<212> TYPE: PRT
<213> ORGANISM: Artificial Sequence
<220> FEATURE:
<223> OTHER INFORMATION: binding peptide

<400> SEQUENCE: 218

Asp Thr Trp Thr His Ser Ser

```
<210> SEQ ID NO 219
<211> LENGTH: 7
<212> TYPE: PRT
<213> ORGANISM: Artificial Sequence
<220> FEATURE:
<223> OTHER INFORMATION: binding peptide

<400> SEQUENCE: 219

Lys Asp Met Pro Thr Gln Phe
1               5

<210> SEQ ID NO 220
<211> LENGTH: 7
<212> TYPE: PRT
<213> ORGANISM: Artificial Sequence
<220> FEATURE:
<223> OTHER INFORMATION: binding peptide

<400> SEQUENCE: 220

Ile Ser Asn Asn Thr His Asn
1               5

<210> SEQ ID NO 221
<211> LENGTH: 7
<212> TYPE: PRT
<213> ORGANISM: Artificial Sequence
<220> FEATURE:
<223> OTHER INFORMATION: binding peptide

<400> SEQUENCE: 221

Ile Asn Thr Pro His Ser Met
1               5

<210> SEQ ID NO 222
<211> LENGTH: 7
<212> TYPE: PRT
<213> ORGANISM: Artificial Sequence
<220> FEATURE:
<223> OTHER INFORMATION: binding peptide

<400> SEQUENCE: 222

Lys Asp Gly Asn Pro Gly Tyr
1               5

<210> SEQ ID NO 223
<211> LENGTH: 7
<212> TYPE: PRT
<213> ORGANISM: Artificial Sequence
<220> FEATURE:
<223> OTHER INFORMATION: binding peptide

<400> SEQUENCE: 223

Lys Asn Pro Asn Asn Asp Arg
1               5

<210> SEQ ID NO 224
<211> LENGTH: 7
<212> TYPE: PRT
<213> ORGANISM: Artificial Sequence
<220> FEATURE:
<223> OTHER INFORMATION: binding peptide

<400> SEQUENCE: 224

Ser Ser Trp Pro Ala Met Pro
1               5
```

```
<210> SEQ ID NO 225
<211> LENGTH: 7
<212> TYPE: PRT
<213> ORGANISM: Artificial Sequence
<220> FEATURE:
<223> OTHER INFORMATION: binding peptide

<400> SEQUENCE: 225

Asp Asn Gln Ala Phe Gly Leu
1               5

<210> SEQ ID NO 226
<211> LENGTH: 7
<212> TYPE: PRT
<213> ORGANISM: Artificial Sequence
<220> FEATURE:
<223> OTHER INFORMATION: binding peptide

<400> SEQUENCE: 226

Pro His Lys Asp Pro Gln Arg
1               5

<210> SEQ ID NO 227
<211> LENGTH: 7
<212> TYPE: PRT
<213> ORGANISM: Artificial Sequence
<220> FEATURE:
<223> OTHER INFORMATION: binding peptide

<400> SEQUENCE: 227

Thr Lys Cys Pro Ser Ser Thr
1               5

<210> SEQ ID NO 228
<211> LENGTH: 7
<212> TYPE: PRT
<213> ORGANISM: Artificial Sequence
<220> FEATURE:
<223> OTHER INFORMATION: binding peptide

<400> SEQUENCE: 228

Glu Ala Asn Thr Gln Thr Ala
1               5

<210> SEQ ID NO 229
<211> LENGTH: 7
<212> TYPE: PRT
<213> ORGANISM: Artificial Sequence
<220> FEATURE:
<223> OTHER INFORMATION: binding peptide

<400> SEQUENCE: 229

His Gln Met Ser Ser Gln Thr
1               5

<210> SEQ ID NO 230
<211> LENGTH: 7
<212> TYPE: PRT
<213> ORGANISM: Artificial Sequence
<220> FEATURE:
<223> OTHER INFORMATION: binding peptide

<400> SEQUENCE: 230

Thr Ser Asn His Gln Ser Ser
1               5
```

```
<210> SEQ ID NO 231
<211> LENGTH: 7
<212> TYPE: PRT
<213> ORGANISM: Artificial Sequence
<220> FEATURE:
<223> OTHER INFORMATION: binding peptide

<400> SEQUENCE: 231

Leu Pro Leu Lys Asn Ser Ala
 1               5

<210> SEQ ID NO 232
<211> LENGTH: 7
<212> TYPE: PRT
<213> ORGANISM: Artificial Sequence
<220> FEATURE:
<223> OTHER INFORMATION: binding peptide

<400> SEQUENCE: 232

Pro Ser Ala Thr Ser Leu Met
 1               5

<210> SEQ ID NO 233
<211> LENGTH: 7
<212> TYPE: PRT
<213> ORGANISM: Artificial Sequence
<220> FEATURE:
<223> OTHER INFORMATION: binding peptide

<400> SEQUENCE: 233

Ser Thr Pro Gly Ser Leu Gln
 1               5

<210> SEQ ID NO 234
<211> LENGTH: 7
<212> TYPE: PRT
<213> ORGANISM: Artificial Sequence
<220> FEATURE:
<223> OTHER INFORMATION: binding peptide

<400> SEQUENCE: 234

His His Gln Asn Ala Leu His
 1               5

<210> SEQ ID NO 235
<211> LENGTH: 7
<212> TYPE: PRT
<213> ORGANISM: Artificial Sequence
<220> FEATURE:
<223> OTHER INFORMATION: binding peptide

<400> SEQUENCE: 235

Asp Pro Leu Arg Gln Thr Thr
 1               5

<210> SEQ ID NO 236
<211> LENGTH: 7
<212> TYPE: PRT
<213> ORGANISM: Artificial Sequence
<220> FEATURE:
<223> OTHER INFORMATION: binding peptide

<400> SEQUENCE: 236

Asn Pro Lys Thr Asn Val Ser
 1               5
```

```
<210> SEQ ID NO 237
<211> LENGTH: 7
<212> TYPE: PRT
<213> ORGANISM: Artificial Sequence
<220> FEATURE:
<223> OTHER INFORMATION: binding peptide

<400> SEQUENCE: 237

Ser Asn Leu Ala Pro Met Leu
1               5

<210> SEQ ID NO 238
<211> LENGTH: 7
<212> TYPE: PRT
<213> ORGANISM: Artificial Sequence
<220> FEATURE:
<223> OTHER INFORMATION: binding peptide

<400> SEQUENCE: 238

Phe Thr Ala Met Asn Asn Ser
1               5

<210> SEQ ID NO 239
<211> LENGTH: 7
<212> TYPE: PRT
<213> ORGANISM: Artificial Sequence
<220> FEATURE:
<223> OTHER INFORMATION: binding peptide

<400> SEQUENCE: 239

Glu Pro His Ala Arg Ser Met
1               5

<210> SEQ ID NO 240
<211> LENGTH: 7
<212> TYPE: PRT
<213> ORGANISM: Artificial Sequence
<220> FEATURE:
<223> OTHER INFORMATION: binding peptide

<400> SEQUENCE: 240

Asn Ser Leu Ser Pro Gly Asn
1               5

<210> SEQ ID NO 241
<211> LENGTH: 7
<212> TYPE: PRT
<213> ORGANISM: Artificial Sequence
<220> FEATURE:
<223> OTHER INFORMATION: binding peptide

<400> SEQUENCE: 241

Glu His Asn Arg Gln Lys Asn
1               5

<210> SEQ ID NO 242
<211> LENGTH: 7
<212> TYPE: PRT
<213> ORGANISM: Artificial Sequence
<220> FEATURE:
<223> OTHER INFORMATION: binding peptide

<400> SEQUENCE: 242

Thr Pro Thr Ser Pro Pro Gly
1               5

<210> SEQ ID NO 243
```

```
<211> LENGTH: 7
<212> TYPE: PRT
<213> ORGANISM: Artificial Sequence
<220> FEATURE:
<223> OTHER INFORMATION: binding peptide

<400> SEQUENCE: 243

Asn Leu Ala Thr Ser Asn Ala
 1               5

<210> SEQ ID NO 244
<211> LENGTH: 7
<212> TYPE: PRT
<213> ORGANISM: Artificial Sequence
<220> FEATURE:
<223> OTHER INFORMATION: binding peptide

<400> SEQUENCE: 244

Asn Ser Thr Asp Arg Ser Thr
 1               5

<210> SEQ ID NO 245
<211> LENGTH: 7
<212> TYPE: PRT
<213> ORGANISM: Artificial Sequence
<220> FEATURE:
<223> OTHER INFORMATION: binding peptide

<400> SEQUENCE: 245

Ser Pro Thr Ala Ala Gln Ser
 1               5

<210> SEQ ID NO 246
<211> LENGTH: 7
<212> TYPE: PRT
<213> ORGANISM: Artificial Sequence
<220> FEATURE:
<223> OTHER INFORMATION: binding peptide

<400> SEQUENCE: 246

Thr Thr Thr Thr Ser Leu Leu
 1               5

<210> SEQ ID NO 247
<211> LENGTH: 7
<212> TYPE: PRT
<213> ORGANISM: Artificial Sequence
<220> FEATURE:
<223> OTHER INFORMATION: binding peptide

<400> SEQUENCE: 247

Pro Ser Met Leu Asn Ala Thr
 1               5

<210> SEQ ID NO 248
<211> LENGTH: 7
<212> TYPE: PRT
<213> ORGANISM: Artificial Sequence
<220> FEATURE:
<223> OTHER INFORMATION: binding peptide

<400> SEQUENCE: 248

Asn Thr His Ser Gly Lys Pro
 1               5

<210> SEQ ID NO 249
<211> LENGTH: 7
```

```
<212> TYPE: PRT
<213> ORGANISM: Artificial Sequence
<220> FEATURE:
<223> OTHER INFORMATION: binding peptide

<400> SEQUENCE: 249

His Pro Pro Trp Met Ser Gln
1               5

<210> SEQ ID NO 250
<211> LENGTH: 7
<212> TYPE: PRT
<213> ORGANISM: Artificial Sequence
<220> FEATURE:
<223> OTHER INFORMATION: binding peptide

<400> SEQUENCE: 250

Thr Arg Ser Thr His Thr Thr
1               5

<210> SEQ ID NO 251
<211> LENGTH: 7
<212> TYPE: PRT
<213> ORGANISM: Artificial Sequence
<220> FEATURE:
<223> OTHER INFORMATION: binding peptide

<400> SEQUENCE: 251

Gly Arg His Pro Leu Met Asn
1               5

<210> SEQ ID NO 252
<211> LENGTH: 7
<212> TYPE: PRT
<213> ORGANISM: Artificial Sequence
<220> FEATURE:
<223> OTHER INFORMATION: binding peptide

<400> SEQUENCE: 252

Thr Gln Lys Glu His Gln Arg
1               5

<210> SEQ ID NO 253
<211> LENGTH: 7
<212> TYPE: PRT
<213> ORGANISM: Artificial Sequence
<220> FEATURE:
<223> OTHER INFORMATION: binding peptide

<400> SEQUENCE: 253

Ala Leu Lys Glu Ala Leu Ser
1               5

<210> SEQ ID NO 254
<211> LENGTH: 7
<212> TYPE: PRT
<213> ORGANISM: Artificial Sequence
<220> FEATURE:
<223> OTHER INFORMATION: binding peptide

<400> SEQUENCE: 254

His Thr Thr Thr Ser His His
1               5

<210> SEQ ID NO 255
<211> LENGTH: 7
<212> TYPE: PRT
```

```
<213> ORGANISM: Artificial Sequence
<220> FEATURE:
<223> OTHER INFORMATION: binding peptide

<400> SEQUENCE: 255

Glu Ala Thr Phe His Lys Asp
 1               5

<210> SEQ ID NO 256
<211> LENGTH: 7
<212> TYPE: PRT
<213> ORGANISM: Artificial Sequence
<220> FEATURE:
<223> OTHER INFORMATION: binding peptide

<400> SEQUENCE: 256

Arg Leu Ser Asp Pro Met His
 1               5

<210> SEQ ID NO 257
<211> LENGTH: 7
<212> TYPE: PRT
<213> ORGANISM: Artificial Sequence
<220> FEATURE:
<223> OTHER INFORMATION: binding peptide

<400> SEQUENCE: 257

Thr Asp Phe Phe Gly Arg Val
 1               5

<210> SEQ ID NO 258
<211> LENGTH: 7
<212> TYPE: PRT
<213> ORGANISM: Artificial Sequence
<220> FEATURE:
<223> OTHER INFORMATION: binding peptide

<400> SEQUENCE: 258

Gly Gln Asn Pro Met Lys Ser
 1               5

<210> SEQ ID NO 259
<211> LENGTH: 7
<212> TYPE: PRT
<213> ORGANISM: Artificial Sequence
<220> FEATURE:
<223> OTHER INFORMATION: binding peptide

<400> SEQUENCE: 259

Thr Ala Pro Ser Phe Thr Lys
 1               5

<210> SEQ ID NO 260
<211> LENGTH: 7
<212> TYPE: PRT
<213> ORGANISM: Artificial Sequence
<220> FEATURE:
<223> OTHER INFORMATION: binding peptide

<400> SEQUENCE: 260

Phe Asp Ser Lys Asn Thr Pro
 1               5

<210> SEQ ID NO 261
<211> LENGTH: 7
<212> TYPE: PRT
<213> ORGANISM: Artificial Sequence
```

```
<220> FEATURE:
<223> OTHER INFORMATION: binding peptide

<400> SEQUENCE: 261

Gln Gln Leu Asn Thr Pro Arg
1               5

<210> SEQ ID NO 262
<211> LENGTH: 7
<212> TYPE: PRT
<213> ORGANISM: Artificial Sequence
<220> FEATURE:
<223> OTHER INFORMATION: binding peptide

<400> SEQUENCE: 262

His Ile Pro Ser Ala Leu Leu
1               5

<210> SEQ ID NO 263
<211> LENGTH: 7
<212> TYPE: PRT
<213> ORGANISM: Artificial Sequence
<220> FEATURE:
<223> OTHER INFORMATION: binding peptide

<400> SEQUENCE: 263

Glu Leu Thr Pro Ala Leu His
1               5

<210> SEQ ID NO 264
<211> LENGTH: 7
<212> TYPE: PRT
<213> ORGANISM: Artificial Sequence
<220> FEATURE:
<223> OTHER INFORMATION: binding peptide

<400> SEQUENCE: 264

Thr Pro Pro Thr Lys Lys Gln
1               5

<210> SEQ ID NO 265
<211> LENGTH: 7
<212> TYPE: PRT
<213> ORGANISM: Artificial Sequence
<220> FEATURE:
<223> OTHER INFORMATION: binding peptide

<400> SEQUENCE: 265

Ser Gly Ile Pro Arg Asn Ser
1               5

<210> SEQ ID NO 266
<211> LENGTH: 7
<212> TYPE: PRT
<213> ORGANISM: Artificial Sequence
<220> FEATURE:
<223> OTHER INFORMATION: binding peptide

<400> SEQUENCE: 266

Val Gln Pro Val Thr Arg Tyr
1               5

<210> SEQ ID NO 267
<211> LENGTH: 7
<212> TYPE: PRT
<213> ORGANISM: Artificial Sequence
<220> FEATURE:
```

-continued

<223> OTHER INFORMATION: binding peptide

<400> SEQUENCE: 267

Lys Gly Met His Thr Thr Asp
 1               5

<210> SEQ ID NO 268
<211> LENGTH: 7
<212> TYPE: PRT
<213> ORGANISM: Artificial Sequence
<220> FEATURE:
<223> OTHER INFORMATION: binding peptide

<400> SEQUENCE: 268

Pro Met Trp Gly Thr His Leu
 1               5

<210> SEQ ID NO 269
<211> LENGTH: 7
<212> TYPE: PRT
<213> ORGANISM: Artificial Sequence
<220> FEATURE:
<223> OTHER INFORMATION: binding peptide

<400> SEQUENCE: 269

Asn Ala Ala Lys Leu Glu Gln
 1               5

<210> SEQ ID NO 270
<211> LENGTH: 7
<212> TYPE: PRT
<213> ORGANISM: Artificial Sequence
<220> FEATURE:
<223> OTHER INFORMATION: binding peptide

<400> SEQUENCE: 270

Pro Gln Glu Ala Leu Gln Leu
 1               5

<210> SEQ ID NO 271
<211> LENGTH: 7
<212> TYPE: PRT
<213> ORGANISM: Artificial Sequence
<220> FEATURE:
<223> OTHER INFORMATION: binding peptide

<400> SEQUENCE: 271

Ser Arg Asp Met His Pro His
 1               5

<210> SEQ ID NO 272
<211> LENGTH: 7
<212> TYPE: PRT
<213> ORGANISM: Artificial Sequence
<220> FEATURE:
<223> OTHER INFORMATION: binding peptide

<400> SEQUENCE: 272

Gly Pro Glu Thr Pro Tyr Gln
 1               5

<210> SEQ ID NO 273
<211> LENGTH: 7
<212> TYPE: PRT
<213> ORGANISM: Artificial Sequence
<220> FEATURE:
<223> OTHER INFORMATION: binding peptide

```
<400> SEQUENCE: 273

Ser Leu Val Gln Ser Leu Glu
1               5

<210> SEQ ID NO 274
<211> LENGTH: 7
<212> TYPE: PRT
<213> ORGANISM: Artificial Sequence
<220> FEATURE:
<223> OTHER INFORMATION: binding peptide

<400> SEQUENCE: 274

Asn Leu Thr Pro Met Ala Arg
1               5

<210> SEQ ID NO 275
<211> LENGTH: 7
<212> TYPE: PRT
<213> ORGANISM: Artificial Sequence
<220> FEATURE:
<223> OTHER INFORMATION: binding peptide

<400> SEQUENCE: 275

Leu Gln Ser Pro Pro Leu Lys
1               5

<210> SEQ ID NO 276
<211> LENGTH: 7
<212> TYPE: PRT
<213> ORGANISM: Artificial Sequence
<220> FEATURE:
<223> OTHER INFORMATION: binding peptide

<400> SEQUENCE: 276

Gln Lys His Ala Phe Arg Ser
1               5

<210> SEQ ID NO 277
<211> LENGTH: 7
<212> TYPE: PRT
<213> ORGANISM: Artificial Sequence
<220> FEATURE:
<223> OTHER INFORMATION: binding peptide

<400> SEQUENCE: 277

Pro Trp Gln Ile Lys Leu Thr
1               5

<210> SEQ ID NO 278
<211> LENGTH: 12
<212> TYPE: PRT
<213> ORGANISM: Artificial Sequence
<220> FEATURE:
<223> OTHER INFORMATION: binding peptide

<400> SEQUENCE: 278

Gly Met Glu Pro Met His Tyr Tyr Ser Arg His Leu
1               5                   10

<210> SEQ ID NO 279
<211> LENGTH: 12
<212> TYPE: PRT
<213> ORGANISM: Artificial Sequence
<220> FEATURE:
<223> OTHER INFORMATION: binding peptide
```

```
<400> SEQUENCE: 279

Gln Thr Thr Asn Ser Asn Met Ala Pro Ala Leu Ser
1               5                   10

<210> SEQ ID NO 280
<211> LENGTH: 12
<212> TYPE: PRT
<213> ORGANISM: Artificial Sequence
<220> FEATURE:
<223> OTHER INFORMATION: binding peptide

<400> SEQUENCE: 280

Thr Pro Pro Ala Thr Leu Val His Trp Ala Asp Pro
1               5                   10

<210> SEQ ID NO 281
<211> LENGTH: 12
<212> TYPE: PRT
<213> ORGANISM: Artificial Sequence
<220> FEATURE:
<223> OTHER INFORMATION: binding peptide

<400> SEQUENCE: 281

Met Gln Asn Leu His Glu Met Ala Trp Thr Ile Gln
1               5                   10

<210> SEQ ID NO 282
<211> LENGTH: 12
<212> TYPE: PRT
<213> ORGANISM: Artificial Sequence
<220> FEATURE:
<223> OTHER INFORMATION: binding peptide

<400> SEQUENCE: 282

Lys Ser Leu Thr Phe Pro Leu Thr Ala Thr Gln Thr
1               5                   10

<210> SEQ ID NO 283
<211> LENGTH: 11
<212> TYPE: PRT
<213> ORGANISM: Artificial Sequence
<220> FEATURE:
<223> OTHER INFORMATION: binding peptide

<400> SEQUENCE: 283

Val Ser His Lys Thr Gly Asn Thr Tyr Ser Arg
1               5                   10

<210> SEQ ID NO 284
<211> LENGTH: 12
<212> TYPE: PRT
<213> ORGANISM: Artificial Sequence
<220> FEATURE:
<223> OTHER INFORMATION: binding peptide

<400> SEQUENCE: 284

Lys Val Asn Ile Pro His Ile His Asp Arg Ile Ala
1               5                   10

<210> SEQ ID NO 285
<211> LENGTH: 12
<212> TYPE: PRT
<213> ORGANISM: Artificial Sequence
<220> FEATURE:
<223> OTHER INFORMATION: binding peptide

<400> SEQUENCE: 285
```

```
Gln Ile Pro Arg Leu Ile Pro His Pro Leu Ala Met
 1               5                  10
```

<210> SEQ ID NO 286
<211> LENGTH: 12
<212> TYPE: PRT
<213> ORGANISM: Artificial Sequence
<220> FEATURE:
<223> OTHER INFORMATION: binding peptide

<400> SEQUENCE: 286

```
Tyr Gln Asn Lys Ile His Ser Arg Thr Ile Ala His
 1               5                  10
```

<210> SEQ ID NO 287
<211> LENGTH: 11
<212> TYPE: PRT
<213> ORGANISM: Artificial Sequence
<220> FEATURE:
<223> OTHER INFORMATION: binding peptide

<400> SEQUENCE: 287

```
Glu Ser Arg Leu Ser Ser Ser Pro Trp Ser Leu
 1               5                  10
```

<210> SEQ ID NO 288
<211> LENGTH: 11
<212> TYPE: PRT
<213> ORGANISM: Artificial Sequence
<220> FEATURE:
<223> OTHER INFORMATION: binding peptide

<400> SEQUENCE: 288

```
Ala Ser Ser His Asp Gln His Ser Thr Glu Gly
 1               5                  10
```

<210> SEQ ID NO 289
<211> LENGTH: 12
<212> TYPE: PRT
<213> ORGANISM: Artificial Sequence
<220> FEATURE:
<223> OTHER INFORMATION: binding peptide

<400> SEQUENCE: 289

```
Ser Pro Leu Thr Gln Tyr Asn Thr Pro Arg His Pro
 1               5                  10
```

<210> SEQ ID NO 290
<211> LENGTH: 12
<212> TYPE: PRT
<213> ORGANISM: Artificial Sequence
<220> FEATURE:
<223> OTHER INFORMATION: binding peptide

<400> SEQUENCE: 290

```
Ile Lys Ser Gln Ala Asp Pro Ala Arg Leu Tyr Ile
 1               5                  10
```

<210> SEQ ID NO 291
<211> LENGTH: 12
<212> TYPE: PRT
<213> ORGANISM: Artificial Sequence
<220> FEATURE:
<223> OTHER INFORMATION: binding peptide

<400> SEQUENCE: 291

```
Asn Lys Thr Pro Asn Ser Met Thr Pro Ile Phe Met
 1               5                  10
```

<210> SEQ ID NO 292
<211> LENGTH: 12
<212> TYPE: PRT
<213> ORGANISM: Artificial Sequence
<220> FEATURE:
<223> OTHER INFORMATION: binding peptide

<400> SEQUENCE: 292

```
Ala Pro Pro Gln Ser Pro Val Tyr Leu Val Pro Leu
 1               5                  10
```

<210> SEQ ID NO 293
<211> LENGTH: 12
<212> TYPE: PRT
<213> ORGANISM: Artificial Sequence
<220> FEATURE:
<223> OTHER INFORMATION: binding peptide

<400> SEQUENCE: 293

```
Leu Pro Ala Gln Tyr Gln Thr Ile Pro Gly Ser Leu
 1               5                  10
```

<210> SEQ ID NO 294
<211> LENGTH: 12
<212> TYPE: PRT
<213> ORGANISM: Artificial Sequence
<220> FEATURE:
<223> OTHER INFORMATION: binding peptide

<400> SEQUENCE: 294

```
Ser Ser Val Pro Met Asp Val Leu Thr Pro Val Val
 1               5                  10
```

<210> SEQ ID NO 295
<211> LENGTH: 12
<212> TYPE: PRT
<213> ORGANISM: Artificial Sequence
<220> FEATURE:
<223> OTHER INFORMATION: binding peptide

<400> SEQUENCE: 295

```
Ala Leu Gly Ser Met Thr Trp Ser Pro Pro Pro Leu
 1               5                  10
```

<210> SEQ ID NO 296
<211> LENGTH: 12
<212> TYPE: PRT
<213> ORGANISM: Artificial Sequence
<220> FEATURE:
<223> OTHER INFORMATION: binding peptide

<400> SEQUENCE: 296

```
Gln Gly Ser His Asn Ser Ser Ala Ile Ser Trp
 1               5                  10
```

<210> SEQ ID NO 297
<211> LENGTH: 12
<212> TYPE: PRT
<213> ORGANISM: Artificial Sequence
<220> FEATURE:
<223> OTHER INFORMATION: binding peptide

<400> SEQUENCE: 297

```
Ser Ser Ile Met Asn Thr Ala Val Leu Gly His Asp
```

<210> SEQ ID NO 298
<211> LENGTH: 12
<212> TYPE: PRT
<213> ORGANISM: Artificial Sequence
<220> FEATURE:
<223> OTHER INFORMATION: binding peptide

<400> SEQUENCE: 298

Ser Thr Leu Trp Tyr Arg Ser Asp Met Thr His Gly
1               5                   10

<210> SEQ ID NO 299
<211> LENGTH: 12
<212> TYPE: PRT
<213> ORGANISM: Artificial Sequence
<220> FEATURE:
<223> OTHER INFORMATION: binding peptide

<400> SEQUENCE: 299

Ala Ser Thr Val Tyr Gln Pro Tyr Val Val His Ala
1               5                   10

<210> SEQ ID NO 300
<211> LENGTH: 12
<212> TYPE: PRT
<213> ORGANISM: Artificial Sequence
<220> FEATURE:
<223> OTHER INFORMATION: binding peptide

<400> SEQUENCE: 300

Ala Ala Arg Asn Asp Gln Val Ser His Met His Met
1               5                   10

<210> SEQ ID NO 301
<211> LENGTH: 12
<212> TYPE: PRT
<213> ORGANISM: Artificial Sequence
<220> FEATURE:
<223> OTHER INFORMATION: binding peptide

<400> SEQUENCE: 301

Glu Val Phe Gln Asn Trp Pro Gln Ser Leu His Lys
1               5                   10

<210> SEQ ID NO 302
<211> LENGTH: 12
<212> TYPE: PRT
<213> ORGANISM: Artificial Sequence
<220> FEATURE:
<223> OTHER INFORMATION: binding peptide

<400> SEQUENCE: 302

Gln Ala Leu Thr His Pro Met Thr Lys Pro Pro Thr
1               5                   10

<210> SEQ ID NO 303
<211> LENGTH: 12
<212> TYPE: PRT
<213> ORGANISM: Artificial Sequence
<220> FEATURE:
<223> OTHER INFORMATION: binding peptide

<400> SEQUENCE: 303

Ser Tyr Thr Lys Pro Asp Gln His Ala Leu Ala Phe
1               5                   10

```
<210> SEQ ID NO 304
<211> LENGTH: 12
<212> TYPE: PRT
<213> ORGANISM: Artificial Sequence
<220> FEATURE:
<223> OTHER INFORMATION: binding peptide

<400> SEQUENCE: 304

Asp Leu Phe Ser Ala His His Thr Gly Gly Ala Leu
 1               5                  10

<210> SEQ ID NO 305
<211> LENGTH: 12
<212> TYPE: PRT
<213> ORGANISM: Artificial Sequence
<220> FEATURE:
<223> OTHER INFORMATION: binding peptide

<400> SEQUENCE: 305

Leu Val Gly His Gln Leu Asn Leu His Ala Leu Arg
 1               5                  10

<210> SEQ ID NO 306
<211> LENGTH: 12
<212> TYPE: PRT
<213> ORGANISM: Artificial Sequence
<220> FEATURE:
<223> OTHER INFORMATION: binding peptide

<400> SEQUENCE: 306

His Gly Glu Val Ala Arg Leu Val Pro Phe Arg Gly
 1               5                  10

<210> SEQ ID NO 307
<211> LENGTH: 10
<212> TYPE: PRT
<213> ORGANISM: Artificial Sequence
<220> FEATURE:
<223> OTHER INFORMATION: binding peptide

<400> SEQUENCE: 307

Ala Cys Lys Leu Glu Met Gly Leu Ser Cys
 1               5                  10

<210> SEQ ID NO 308
<211> LENGTH: 12
<212> TYPE: PRT
<213> ORGANISM: Artificial Sequence
<220> FEATURE:
<223> OTHER INFORMATION: binding peptide

<400> SEQUENCE: 308

Ser Ala Ile Pro Thr Met Gly Arg His Ala His Pro
 1               5                  10

<210> SEQ ID NO 309
<211> LENGTH: 12
<212> TYPE: PRT
<213> ORGANISM: Artificial Sequence
<220> FEATURE:
<223> OTHER INFORMATION: binding peptide

<400> SEQUENCE: 309

Gln Ser Thr Tyr Ser Asn Ile Gly Arg Asp Asp Ser
 1               5                  10
```

```
<210> SEQ ID NO 310
<211> LENGTH: 12
<212> TYPE: PRT
<213> ORGANISM: Artificial Sequence
<220> FEATURE:
<223> OTHER INFORMATION: binding peptide

<400> SEQUENCE: 310

Lys Ala Leu Ser Ala Ser Glu Pro Leu Pro Gln Gly
 1               5                  10

<210> SEQ ID NO 311
<211> LENGTH: 12
<212> TYPE: PRT
<213> ORGANISM: Artificial Sequence
<220> FEATURE:
<223> OTHER INFORMATION: binding peptide

<400> SEQUENCE: 311

Val Ala Ser Arg Leu Thr Gly Ser Val Ala Ser Ala
 1               5                  10

<210> SEQ ID NO 312
<211> LENGTH: 12
<212> TYPE: PRT
<213> ORGANISM: Artificial Sequence
<220> FEATURE:
<223> OTHER INFORMATION: binding peptide

<400> SEQUENCE: 312

Ser Ile Gly Glu Leu Ser Gly Pro Val Arg His Gln
 1               5                  10

<210> SEQ ID NO 313
<211> LENGTH: 12
<212> TYPE: PRT
<213> ORGANISM: Artificial Sequence
<220> FEATURE:
<223> OTHER INFORMATION: binding peptide

<400> SEQUENCE: 313

Gln Gln Asn Pro Tyr Ile Pro Ser Ser Val Thr Arg
 1               5                  10

<210> SEQ ID NO 314
<211> LENGTH: 12
<212> TYPE: PRT
<213> ORGANISM: Artificial Sequence
<220> FEATURE:
<223> OTHER INFORMATION: binding peptide

<400> SEQUENCE: 314

Asn Val Phe Met Gly Ser Leu His Ala Ser Leu Val
 1               5                  10

<210> SEQ ID NO 315
<211> LENGTH: 12
<212> TYPE: PRT
<213> ORGANISM: Artificial Sequence
<220> FEATURE:
<223> OTHER INFORMATION: binding peptide

<400> SEQUENCE: 315

Ser Pro His Ser Met Leu Gln Asn Pro Ser Gly Pro
 1               5                  10
```

```
<210> SEQ ID NO 316
<211> LENGTH: 12
<212> TYPE: PRT
<213> ORGANISM: Artificial Sequence
<220> FEATURE:
<223> OTHER INFORMATION: binding peptide

<400> SEQUENCE: 316

Asn Glu Glu Leu Thr Ser His Thr Asn Gln His Leu
 1               5                  10

<210> SEQ ID NO 317
<211> LENGTH: 12
<212> TYPE: PRT
<213> ORGANISM: Artificial Sequence
<220> FEATURE:
<223> OTHER INFORMATION: binding peptide

<400> SEQUENCE: 317

Tyr Leu Pro Ser Thr Phe Ala Pro Pro Leu Pro Leu
 1               5                  10

<210> SEQ ID NO 318
<211> LENGTH: 12
<212> TYPE: PRT
<213> ORGANISM: Artificial Sequence
<220> FEATURE:
<223> OTHER INFORMATION: binding peptide

<400> SEQUENCE: 318

Ser Val Gln Gly Ser Pro Leu Asp Ser Thr Asn His
 1               5                  10

<210> SEQ ID NO 319
<211> LENGTH: 12
<212> TYPE: PRT
<213> ORGANISM: Artificial Sequence
<220> FEATURE:
<223> OTHER INFORMATION: binding peptide

<400> SEQUENCE: 319

Phe Ser Thr Asp Asp Ser Pro Phe Pro Phe Ala Ala
 1               5                  10

<210> SEQ ID NO 320
<211> LENGTH: 12
<212> TYPE: PRT
<213> ORGANISM: Artificial Sequence
<220> FEATURE:
<223> OTHER INFORMATION: binding peptide

<400> SEQUENCE: 320

Val Gln Gln Ala Thr Ser Gly Leu Ala Arg Pro His
 1               5                  10

<210> SEQ ID NO 321
<211> LENGTH: 12
<212> TYPE: PRT
<213> ORGANISM: Artificial Sequence
<220> FEATURE:
<223> OTHER INFORMATION: binding peptide

<400> SEQUENCE: 321

Ser Asp Gln Ala Ser Leu Leu Asp Gly Trp Arg Phe
 1               5                  10

<210> SEQ ID NO 322
```

```
<211> LENGTH: 12
<212> TYPE: PRT
<213> ORGANISM: Artificial Sequence
<220> FEATURE:
<223> OTHER INFORMATION: binding peptide

<400> SEQUENCE: 322

Asn Thr Leu Met Ile Asn Pro Thr Gln Ala His Leu
1               5                   10

<210> SEQ ID NO 323
<211> LENGTH: 12
<212> TYPE: PRT
<213> ORGANISM: Artificial Sequence
<220> FEATURE:
<223> OTHER INFORMATION: binding peptide

<400> SEQUENCE: 323

Ala His Glu Gly Arg Asn Tyr Gly Leu Val Ile Lys
1               5                   10

<210> SEQ ID NO 324
<211> LENGTH: 12
<212> TYPE: PRT
<213> ORGANISM: Artificial Sequence
<220> FEATURE:
<223> OTHER INFORMATION: binding peptide

<400> SEQUENCE: 324

Gly Asp Ser Thr Leu Phe Asn Thr Trp Gln Ser Ser
1               5                   10

<210> SEQ ID NO 325
<211> LENGTH: 12
<212> TYPE: PRT
<213> ORGANISM: Artificial Sequence
<220> FEATURE:
<223> OTHER INFORMATION: binding peptide

<400> SEQUENCE: 325

Ile Val Arg Val Thr Asp Gly Thr Pro Ser Pro Gly
1               5                   10

<210> SEQ ID NO 326
<211> LENGTH: 12
<212> TYPE: PRT
<213> ORGANISM: Artificial Sequence
<220> FEATURE:
<223> OTHER INFORMATION: binding peptide

<400> SEQUENCE: 326

Ser Ser Pro Leu Gln Thr Ser Pro Pro Trp Pro Tyr
1               5                   10

<210> SEQ ID NO 327
<211> LENGTH: 12
<212> TYPE: PRT
<213> ORGANISM: Artificial Sequence
<220> FEATURE:
<223> OTHER INFORMATION: binding peptide

<400> SEQUENCE: 327

Lys Ala Ile Gly Met Ser Thr Gly Pro Leu Thr Gln
1               5                   10

<210> SEQ ID NO 328
<211> LENGTH: 12
```

```
<212> TYPE: PRT
<213> ORGANISM: Artificial Sequence
<220> FEATURE:
<223> OTHER INFORMATION: binding peptide

<400> SEQUENCE: 328

Leu His Val Thr Thr Thr Ile Pro Gly Gly Leu Arg
 1               5                  10

<210> SEQ ID NO 329
<211> LENGTH: 12
<212> TYPE: PRT
<213> ORGANISM: Artificial Sequence
<220> FEATURE:
<223> OTHER INFORMATION: binding peptide

<400> SEQUENCE: 329

Ser Val Pro Ser Pro Ser Pro Pro Trp Ser Arg Pro
 1               5                  10

<210> SEQ ID NO 330
<211> LENGTH: 12
<212> TYPE: PRT
<213> ORGANISM: Artificial Sequence
<220> FEATURE:
<223> OTHER INFORMATION: binding peptide

<400> SEQUENCE: 330

Val Ala Ser Ala Asn Pro His Ser Met Thr Ser Trp
 1               5                  10

<210> SEQ ID NO 331
<211> LENGTH: 12
<212> TYPE: PRT
<213> ORGANISM: Artificial Sequence
<220> FEATURE:
<223> OTHER INFORMATION: binding peptide

<400> SEQUENCE: 331

Gln Asp Ala Thr Ser Arg Phe Ser Gly Leu Ala Ser
 1               5                  10

<210> SEQ ID NO 332
<211> LENGTH: 12
<212> TYPE: PRT
<213> ORGANISM: Artificial Sequence
<220> FEATURE:
<223> OTHER INFORMATION: binding peptide

<400> SEQUENCE: 332

Ala Glu Ala Ile Thr Ala Ile Pro Leu Pro Val Pro
 1               5                  10

<210> SEQ ID NO 333
<211> LENGTH: 12
<212> TYPE: PRT
<213> ORGANISM: Artificial Sequence
<220> FEATURE:
<223> OTHER INFORMATION: binding peptide

<400> SEQUENCE: 333

Met Asp Pro Phe Ala Thr Ile Pro Ser Thr His Pro
 1               5                  10

<210> SEQ ID NO 334
<211> LENGTH: 12
<212> TYPE: PRT
```

-continued

<213> ORGANISM: Artificial Sequence
<220> FEATURE:
<223> OTHER INFORMATION: binding peptide

<400> SEQUENCE: 334

Glu Gly Asn Ala Arg Leu Ala Gln Ser Leu Ile Gln
1               5                   10

<210> SEQ ID NO 335
<211> LENGTH: 12
<212> TYPE: PRT
<213> ORGANISM: Artificial Sequence
<220> FEATURE:
<223> OTHER INFORMATION: binding peptide

<400> SEQUENCE: 335

Met His Ser Pro Phe Cys Ser Ser Pro Cys Ser Pro
1               5                   10

<210> SEQ ID NO 336
<211> LENGTH: 12
<212> TYPE: PRT
<213> ORGANISM: Artificial Sequence
<220> FEATURE:
<223> OTHER INFORMATION: binding peptide

<400> SEQUENCE: 336

Ser Gly Met Pro Pro Thr Ile Thr Trp Thr Arg Pro
1               5                   10

<210> SEQ ID NO 337
<211> LENGTH: 12
<212> TYPE: PRT
<213> ORGANISM: Artificial Sequence
<220> FEATURE:
<223> OTHER INFORMATION: binding peptide

<400> SEQUENCE: 337

Trp Glu Ala Thr Pro Asn Phe Met Ser Lys Ile Ile
1               5                   10

<210> SEQ ID NO 338
<211> LENGTH: 12
<212> TYPE: PRT
<213> ORGANISM: Artificial Sequence
<220> FEATURE:
<223> OTHER INFORMATION: binding peptide

<400> SEQUENCE: 338

Ala Val Ser Leu Val Pro Pro Asn Leu Ala Thr His
1               5                   10

<210> SEQ ID NO 339
<211> LENGTH: 12
<212> TYPE: PRT
<213> ORGANISM: Artificial Sequence
<220> FEATURE:
<223> OTHER INFORMATION: binding peptide

<400> SEQUENCE: 339

Val Pro Asn Met Thr Pro Ser Ser Tyr Leu Ser Ala
1               5                   10

<210> SEQ ID NO 340
<211> LENGTH: 12
<212> TYPE: PRT
<213> ORGANISM: Artificial Sequence
<220> FEATURE:
<223> OTHER INFORMATION: binding peptide

<400> SEQUENCE: 340

Leu Gln Pro Gln Thr Trp Ser Trp Ala Arg Gly Ala
1               5                   10

<210> SEQ ID NO 341
<211> LENGTH: 12
<212> TYPE: PRT
<213> ORGANISM: Artificial Sequence
<220> FEATURE:
<223> OTHER INFORMATION: binding peptide

<400> SEQUENCE: 341

Thr Glu Pro Thr Val Lys His Pro Pro Leu Arg Ile
1               5                   10

<210> SEQ ID NO 342
<211> LENGTH: 12
<212> TYPE: PRT
<213> ORGANISM: Artificial Sequence
<220> FEATURE:
<223> OTHER INFORMATION: binding peptide

<400> SEQUENCE: 342

Val Ala Leu Pro Asn Gln Pro Pro Arg Ala Gly Leu
1               5                   10

<210> SEQ ID NO 343
<211> LENGTH: 12
<212> TYPE: PRT
<213> ORGANISM: Artificial Sequence
<220> FEATURE:
<223> OTHER INFORMATION: binding peptide

<400> SEQUENCE: 343

Gly Leu Gly Tyr Trp Val Met Pro Ala Pro Thr Ser
1               5                   10

<210> SEQ ID NO 344
<211> LENGTH: 12
<212> TYPE: PRT
<213> ORGANISM: Artificial Sequence
<220> FEATURE:
<223> OTHER INFORMATION: binding peptide

<400> SEQUENCE: 344

His Asn Leu Tyr Met Thr Pro Pro Ser Ile Met Asn
1               5                   10

<210> SEQ ID NO 345
<211> LENGTH: 12
<212> TYPE: PRT
<213> ORGANISM: Artificial Sequence
<220> FEATURE:
<223> OTHER INFORMATION: binding peptide

<400> SEQUENCE: 345

His Ala Glu Lys Ile Leu Ser Ser Pro Gly Pro Ala
1               5                   10

<210> SEQ ID NO 346
<211> LENGTH: 12
<212> TYPE: PRT
<213> ORGANISM: Artificial Sequence
<220> FEATURE:

<223> OTHER INFORMATION: binding peptide

<400> SEQUENCE: 346

His Asn Met Leu Pro Pro Arg Cys Cys Leu Leu Pro
1               5                   10

<210> SEQ ID NO 347
<211> LENGTH: 7
<212> TYPE: PRT
<213> ORGANISM: Artificial Sequence
<220> FEATURE:
<223> OTHER INFORMATION: binding peptide

<400> SEQUENCE: 347

Thr Gln Pro Pro Gly Ser Ser
1               5

<210> SEQ ID NO 348
<211> LENGTH: 7
<212> TYPE: PRT
<213> ORGANISM: Artificial Sequence
<220> FEATURE:
<223> OTHER INFORMATION: binding peptide

<400> SEQUENCE: 348

Met Lys Pro Gln Leu Ser Thr
1               5

<210> SEQ ID NO 349
<211> LENGTH: 12
<212> TYPE: PRT
<213> ORGANISM: Artificial Sequence
<220> FEATURE:
<223> OTHER INFORMATION: binding peptide

<400> SEQUENCE: 349

His Ser Leu Phe Tyr Ser Trp Gly Pro Ser Leu Asp
1               5                   10

<210> SEQ ID NO 350
<211> LENGTH: 12
<212> TYPE: PRT
<213> ORGANISM: Artificial Sequence
<220> FEATURE:
<223> OTHER INFORMATION: binding peptide

<400> SEQUENCE: 350

Val Arg Met Gln Met Asn Thr Gly Leu Pro Gln Arg
1               5                   10

<210> SEQ ID NO 351
<211> LENGTH: 7
<212> TYPE: PRT
<213> ORGANISM: Artificial Sequence
<220> FEATURE:
<223> OTHER INFORMATION: binding peptide

<400> SEQUENCE: 351

Pro His Thr Asn Glu Ile Val
1               5

<210> SEQ ID NO 352
<211> LENGTH: 7
<212> TYPE: PRT
<213> ORGANISM: Artificial Sequence
<220> FEATURE:
<223> OTHER INFORMATION: binding peptide

```
<400> SEQUENCE: 352

Pro Tyr Met Gln Leu Arg Asn
1               5

<210> SEQ ID NO 353
<211> LENGTH: 7
<212> TYPE: PRT
<213> ORGANISM: Artificial Sequence
<220> FEATURE:
<223> OTHER INFORMATION: binding peptide

<400> SEQUENCE: 353

Ala Arg Pro Thr Pro Leu Leu
1               5

<210> SEQ ID NO 354
<211> LENGTH: 12
<212> TYPE: PRT
<213> ORGANISM: Artificial Sequence
<220> FEATURE:
<223> OTHER INFORMATION: binding peptide

<400> SEQUENCE: 354

Leu Asp Thr Ile Asp Thr Asn Pro Pro Val His Ser
1               5                   10

<210> SEQ ID NO 355
<211> LENGTH: 7
<212> TYPE: PRT
<213> ORGANISM: Artificial Sequence
<220> FEATURE:
<223> OTHER INFORMATION: binding peptide

<400> SEQUENCE: 355

Pro Thr His Pro Leu Pro Thr
1               5

<210> SEQ ID NO 356
<211> LENGTH: 7
<212> TYPE: PRT
<213> ORGANISM: Artificial Sequence
<220> FEATURE:
<223> OTHER INFORMATION: binding peptide

<400> SEQUENCE: 356

Asn Ser Trp Cys Ala Ala Thr
1               5

<210> SEQ ID NO 357
<211> LENGTH: 12
<212> TYPE: PRT
<213> ORGANISM: Artificial Sequence
<220> FEATURE:
<223> OTHER INFORMATION: binding peptide

<400> SEQUENCE: 357

Ile Pro Thr Ser Leu Met Ala His Pro His Pro Ala
1               5                   10

<210> SEQ ID NO 358
<211> LENGTH: 7
<212> TYPE: PRT
<213> ORGANISM: Artificial Sequence
<220> FEATURE:
<223> OTHER INFORMATION: binding peptide
```

```
<400> SEQUENCE: 358

Gln Gly Gln Ser Gln Gln Ser
1               5

<210> SEQ ID NO 359
<211> LENGTH: 7
<212> TYPE: PRT
<213> ORGANISM: Artificial Sequence
<220> FEATURE:
<223> OTHER INFORMATION: binding peptide

<400> SEQUENCE: 359

Asn Ala Pro Ala Met Lys Leu
1               5

<210> SEQ ID NO 360
<211> LENGTH: 7
<212> TYPE: PRT
<213> ORGANISM: Artificial Sequence
<220> FEATURE:
<223> OTHER INFORMATION: binding peptide

<400> SEQUENCE: 360

Thr Leu Trp Pro Pro Arg Ala
1               5

<210> SEQ ID NO 361
<211> LENGTH: 11
<212> TYPE: PRT
<213> ORGANISM: Artificial Sequence
<220> FEATURE:
<223> OTHER INFORMATION: binding peptide

<400> SEQUENCE: 361

Gly Gln Gln Asp Arg Arg Glu Pro Ile Ile Ile
1               5                   10

<210> SEQ ID NO 362
<211> LENGTH: 7
<212> TYPE: PRT
<213> ORGANISM: Artificial Sequence
<220> FEATURE:
<223> OTHER INFORMATION: binding peptide

<400> SEQUENCE: 362

Arg Ile Pro Ala Glu Lys Val
1               5

<210> SEQ ID NO 363
<211> LENGTH: 7
<212> TYPE: PRT
<213> ORGANISM: Artificial Sequence
<220> FEATURE:
<223> OTHER INFORMATION: binding peptide

<400> SEQUENCE: 363

Met Pro Ser Pro Thr Tyr Gln
1               5

<210> SEQ ID NO 364
<211> LENGTH: 7
<212> TYPE: PRT
<213> ORGANISM: Artificial Sequence
<220> FEATURE:
<223> OTHER INFORMATION: binding peptide

<400> SEQUENCE: 364
```

Lys Ser Thr Trp Gln Gly Leu
1               5

<210> SEQ ID NO 365
<211> LENGTH: 12
<212> TYPE: PRT
<213> ORGANISM: Artificial Sequence
<220> FEATURE:
<223> OTHER INFORMATION: binding peptide

<400> SEQUENCE: 365

Ser Leu Pro Ala Gln Pro Arg Leu Thr His Leu Trp
1               5                   10

<210> SEQ ID NO 366
<211> LENGTH: 12
<212> TYPE: PRT
<213> ORGANISM: Artificial Sequence
<220> FEATURE:
<223> OTHER INFORMATION: binding peptide

<400> SEQUENCE: 366

His Trp Asn Thr Ala Ala Leu Asn His Met Arg Phe
1               5                   10

<210> SEQ ID NO 367
<211> LENGTH: 12
<212> TYPE: PRT
<213> ORGANISM: Artificial Sequence
<220> FEATURE:
<223> OTHER INFORMATION: binding peptide

<400> SEQUENCE: 367

Thr His Gln Thr Thr Glu Leu Leu Pro Arg Ala Ser
1               5                   10

<210> SEQ ID NO 368
<211> LENGTH: 12
<212> TYPE: PRT
<213> ORGANISM: Artificial Sequence
<220> FEATURE:
<223> OTHER INFORMATION: binding peptide

<400> SEQUENCE: 368

Val Leu Ala Leu Val Lys Thr Ser Leu Asn Glu Pro
1               5                   10

<210> SEQ ID NO 369
<211> LENGTH: 12
<212> TYPE: PRT
<213> ORGANISM: Artificial Sequence
<220> FEATURE:
<223> OTHER INFORMATION: binding peptide

<400> SEQUENCE: 369

Gly Thr Tyr Asn Leu Pro Asn Pro Pro Pro Pro Leu
1               5                   10

<210> SEQ ID NO 370
<211> LENGTH: 7
<212> TYPE: PRT
<213> ORGANISM: Artificial Sequence
<220> FEATURE:
<223> OTHER INFORMATION: binding peptide

<400> SEQUENCE: 370

```
Leu Pro Asn Arg Thr Pro Val
 1               5
```

<210> SEQ ID NO 371
<211> LENGTH: 7
<212> TYPE: PRT
<213> ORGANISM: Artificial Sequence
<220> FEATURE:
<223> OTHER INFORMATION: binding peptide

<400> SEQUENCE: 371

```
Gly Gly Thr Cys Phe Leu Ala
 1               5
```

<210> SEQ ID NO 372
<211> LENGTH: 12
<212> TYPE: PRT
<213> ORGANISM: Artificial Sequence
<220> FEATURE:
<223> OTHER INFORMATION: binding peptide

<400> SEQUENCE: 372

```
Arg Thr Glu Ser Phe Ser Pro Leu Ser Phe Ser Ser
 1               5                   10
```

<210> SEQ ID NO 373
<211> LENGTH: 12
<212> TYPE: PRT
<213> ORGANISM: Artificial Sequence
<220> FEATURE:
<223> OTHER INFORMATION: binding peptide

<400> SEQUENCE: 373

```
Glu Thr Val Ser Asn Phe Ser Asn Val Ser Thr Lys
 1               5                   10
```

<210> SEQ ID NO 374
<211> LENGTH: 7
<212> TYPE: PRT
<213> ORGANISM: Artificial Sequence
<220> FEATURE:
<223> OTHER INFORMATION: binding peptide

<400> SEQUENCE: 374

```
Ser Glu Pro Ala Arg Thr Pro
 1               5
```

<210> SEQ ID NO 375
<211> LENGTH: 12
<212> TYPE: PRT
<213> ORGANISM: Artificial Sequence
<220> FEATURE:
<223> OTHER INFORMATION: binding peptide

<400> SEQUENCE: 375

```
Gly Ser Ser Pro Leu Pro Leu Lys Phe Thr Gly Pro
 1               5                   10
```

<210> SEQ ID NO 376
<211> LENGTH: 12
<212> TYPE: PRT
<213> ORGANISM: Artificial Sequence
<220> FEATURE:
<223> OTHER INFORMATION: binding peptide

<400> SEQUENCE: 376

```
Ile Pro Asn His Tyr Thr His Tyr Ala Ser Pro Pro
```

-continued

```
1               5                   10

<210> SEQ ID NO 377
<211> LENGTH: 7
<212> TYPE: PRT
<213> ORGANISM: Artificial Sequence
<220> FEATURE:
<223> OTHER INFORMATION: binding peptide

<400> SEQUENCE: 377

Thr Trp Gly Gln Pro His Gly
1               5

<210> SEQ ID NO 378
<211> LENGTH: 12
<212> TYPE: PRT
<213> ORGANISM: Artificial Sequence
<220> FEATURE:
<223> OTHER INFORMATION: binding peptide

<400> SEQUENCE: 378

Leu Lys Ala Gln Glu Phe Lys Ala Thr Pro Pro Val
1               5                   10

<210> SEQ ID NO 379
<211> LENGTH: 12
<212> TYPE: PRT
<213> ORGANISM: Artificial Sequence
<220> FEATURE:
<223> OTHER INFORMATION: binding peptide

<400> SEQUENCE: 379

Ala Pro Arg Ser Asp Ser Leu Ile Leu Ser Pro Ser
1               5                   10

<210> SEQ ID NO 380
<211> LENGTH: 12
<212> TYPE: PRT
<213> ORGANISM: Artificial Sequence
<220> FEATURE:
<223> OTHER INFORMATION: binding peptide

<400> SEQUENCE: 380

Leu Arg Pro Pro Thr Ala Leu Ser Ala Ala Leu His
1               5                   10

<210> SEQ ID NO 381
<211> LENGTH: 7
<212> TYPE: PRT
<213> ORGANISM: Artificial Sequence
<220> FEATURE:
<223> OTHER INFORMATION: binding peptide

<400> SEQUENCE: 381

Leu Arg Asp Thr His Ala Ile
1               5

<210> SEQ ID NO 382
<211> LENGTH: 12
<212> TYPE: PRT
<213> ORGANISM: Artificial Sequence
<220> FEATURE:
<223> OTHER INFORMATION: binding peptide

<400> SEQUENCE: 382

Phe Asn Met Thr Thr Phe Ser Leu Ala Arg Ser Ser
1               5                   10
```

<210> SEQ ID NO 383
<211> LENGTH: 12
<212> TYPE: PRT
<213> ORGANISM: Artificial Sequence
<220> FEATURE:
<223> OTHER INFORMATION: binding peptide

<400> SEQUENCE: 383

Phe Asn Pro Lys Thr Pro Lys Ile Ala Pro Asn Ile
1               5                   10

<210> SEQ ID NO 384
<211> LENGTH: 7
<212> TYPE: PRT
<213> ORGANISM: Artificial Sequence
<220> FEATURE:
<223> OTHER INFORMATION: binding peptide

<400> SEQUENCE: 384

Thr Leu Pro Asn Val Leu Arg
1               5

<210> SEQ ID NO 385
<211> LENGTH: 12
<212> TYPE: PRT
<213> ORGANISM: Artificial Sequence
<220> FEATURE:
<223> OTHER INFORMATION: binding peptide

<400> SEQUENCE: 385

Ser Arg Asn Ile Pro Leu Pro Ser His Phe Leu Ser
1               5                   10

<210> SEQ ID NO 386
<211> LENGTH: 7
<212> TYPE: PRT
<213> ORGANISM: Artificial Sequence
<220> FEATURE:
<223> OTHER INFORMATION: binding peptide

<400> SEQUENCE: 386

Ser Arg Pro Gly Ser Pro Val
1               5

<210> SEQ ID NO 387
<211> LENGTH: 12
<212> TYPE: PRT
<213> ORGANISM: Artificial Sequence
<220> FEATURE:
<223> OTHER INFORMATION: binding peptide

<400> SEQUENCE: 387

Asn Leu Asn Arg Gln Pro Val Met Lys His Trp Pro
1               5                   10

<210> SEQ ID NO 388
<211> LENGTH: 12
<212> TYPE: PRT
<213> ORGANISM: Artificial Sequence
<220> FEATURE:
<223> OTHER INFORMATION: binding peptide

<400> SEQUENCE: 388

Phe Gln Thr Thr Ala Thr Arg Leu Gly Phe Ala Pro
1               5                   10

```
<210> SEQ ID NO 389
<211> LENGTH: 12
<212> TYPE: PRT
<213> ORGANISM: Artificial Sequence
<220> FEATURE:
<223> OTHER INFORMATION: binding peptide

<400> SEQUENCE: 389

Leu Ser Val Ser Pro Arg Met Thr Pro Phe Val Thr
1               5                   10

<210> SEQ ID NO 390
<211> LENGTH: 12
<212> TYPE: PRT
<213> ORGANISM: Artificial Sequence
<220> FEATURE:
<223> OTHER INFORMATION: binding peptide

<400> SEQUENCE: 390

Lys Ser His Thr Ser Met Glu Gln Leu Asn Ser Gln
1               5                   10

<210> SEQ ID NO 391
<211> LENGTH: 12
<212> TYPE: PRT
<213> ORGANISM: Artificial Sequence
<220> FEATURE:
<223> OTHER INFORMATION: binding peptide

<400> SEQUENCE: 391

Glu Ser Phe Ser Val Thr Trp Leu Pro Ala Arg Thr
1               5                   10

<210> SEQ ID NO 392
<211> LENGTH: 12
<212> TYPE: PRT
<213> ORGANISM: Artificial Sequence
<220> FEATURE:
<223> OTHER INFORMATION: binding peptide

<400> SEQUENCE: 392

Gly Gln Trp Gln Ala Asp Arg Leu Arg Ser Leu Pro
1               5                   10

<210> SEQ ID NO 393
<211> LENGTH: 12
<212> TYPE: PRT
<213> ORGANISM: Artificial Sequence
<220> FEATURE:
<223> OTHER INFORMATION: binding peptide

<400> SEQUENCE: 393

Phe Asp Val Ser Thr Val Leu Ser Ser Ser Thr His
1               5                   10

<210> SEQ ID NO 394
<211> LENGTH: 12
<212> TYPE: PRT
<213> ORGANISM: Artificial Sequence
<220> FEATURE:
<223> OTHER INFORMATION: binding peptide

<400> SEQUENCE: 394

Gln Val Asp Gly Thr Asn Asp Thr Arg Pro Ser Arg
1               5                   10
```

```
<210> SEQ ID NO 395
<211> LENGTH: 12
<212> TYPE: PRT
<213> ORGANISM: Artificial Sequence
<220> FEATURE:
<223> OTHER INFORMATION: binding peptide

<400> SEQUENCE: 395

Lys Ala Ser Asn Leu Ser Pro Ile Leu Gly Leu Pro
1               5                   10

<210> SEQ ID NO 396
<211> LENGTH: 12
<212> TYPE: PRT
<213> ORGANISM: Artificial Sequence
<220> FEATURE:
<223> OTHER INFORMATION: binding peptide

<400> SEQUENCE: 396

Ala Asn His Trp Ile Ala Ser Pro Tyr Trp Ser Leu
1               5                   10

<210> SEQ ID NO 397
<211> LENGTH: 12
<212> TYPE: PRT
<213> ORGANISM: Artificial Sequence
<220> FEATURE:
<223> OTHER INFORMATION: binding peptide

<400> SEQUENCE: 397

Thr Val Gly Thr His Ser Met Arg Thr Pro Arg Cys
1               5                   10

<210> SEQ ID NO 398
<211> LENGTH: 12
<212> TYPE: PRT
<213> ORGANISM: Artificial Sequence
<220> FEATURE:
<223> OTHER INFORMATION: binding peptide

<400> SEQUENCE: 398

Tyr Phe Gln Ala Thr Glu Leu Ser Pro Asn Asn Pro
1               5                   10

<210> SEQ ID NO 399
<211> LENGTH: 7
<212> TYPE: PRT
<213> ORGANISM: Artificial Sequence
<220> FEATURE:
<223> OTHER INFORMATION: binding peptide

<400> SEQUENCE: 399

Ser Ser Pro His Leu Thr Glu
1               5

<210> SEQ ID NO 400
<211> LENGTH: 12
<212> TYPE: PRT
<213> ORGANISM: Artificial Sequence
<220> FEATURE:
<223> OTHER INFORMATION: binding peptide

<400> SEQUENCE: 400

Lys Tyr Pro Glu Asn Met Glu Val Ile Arg Pro Phe
1               5                   10

<210> SEQ ID NO 401
```

```
<211> LENGTH: 7
<212> TYPE: PRT
<213> ORGANISM: Artificial Sequence
<220> FEATURE:
<223> OTHER INFORMATION: binding peptide

<400> SEQUENCE: 401

Thr Ser Ser Gly Ser Asn Leu
1               5

<210> SEQ ID NO 402
<211> LENGTH: 12
<212> TYPE: PRT
<213> ORGANISM: Artificial Sequence
<220> FEATURE:
<223> OTHER INFORMATION: binding peptide

<400> SEQUENCE: 402

Ser Pro Ser Leu Pro Arg Met Asp Val Ser Thr Pro
1               5                   10

<210> SEQ ID NO 403
<211> LENGTH: 12
<212> TYPE: PRT
<213> ORGANISM: Artificial Sequence
<220> FEATURE:
<223> OTHER INFORMATION: binding peptide

<400> SEQUENCE: 403

Ile Thr Leu Pro His Ala Ala Met His Arg Ala Tyr
1               5                   10

<210> SEQ ID NO 404
<211> LENGTH: 12
<212> TYPE: PRT
<213> ORGANISM: Artificial Sequence
<220> FEATURE:
<223> OTHER INFORMATION: binding peptide

<400> SEQUENCE: 404

His Tyr Phe Pro Asn Pro Leu Ser Ala His Pro Pro
1               5                   10

<210> SEQ ID NO 405
<211> LENGTH: 7
<212> TYPE: PRT
<213> ORGANISM: Artificial Sequence
<220> FEATURE:
<223> OTHER INFORMATION: binding peptide

<400> SEQUENCE: 405

Met Val Pro Ser Tyr Met Arg
1               5

<210> SEQ ID NO 406
<211> LENGTH: 7
<212> TYPE: PRT
<213> ORGANISM: Artificial Sequence
<220> FEATURE:
<223> OTHER INFORMATION: binding peptide

<400> SEQUENCE: 406

Thr Glu Pro His Lys Ala Asn
1               5

<210> SEQ ID NO 407
<211> LENGTH: 12
```

```
<212> TYPE: PRT
<213> ORGANISM: Artificial Sequence
<220> FEATURE:
<223> OTHER INFORMATION: binding peptide

<400> SEQUENCE: 407

Ala Ser Ala Gln His Lys Val Asn Phe Pro Arg Trp
 1               5                  10

<210> SEQ ID NO 408
<211> LENGTH: 7
<212> TYPE: PRT
<213> ORGANISM: Artificial Sequence
<220> FEATURE:
<223> OTHER INFORMATION: binding peptide

<400> SEQUENCE: 408

Pro His His Ser Arg Ala Arg
 1               5

<210> SEQ ID NO 409
<211> LENGTH: 7
<212> TYPE: PRT
<213> ORGANISM: Artificial Sequence
<220> FEATURE:
<223> OTHER INFORMATION: binding peptide

<400> SEQUENCE: 409

Ser Leu His Tyr Asn Gln Ala
 1               5

<210> SEQ ID NO 410
<211> LENGTH: 7
<212> TYPE: PRT
<213> ORGANISM: Artificial Sequence
<220> FEATURE:
<223> OTHER INFORMATION: binding peptide

<400> SEQUENCE: 410

Ser Pro Thr Thr Gly Gln Ser
 1               5

<210> SEQ ID NO 411
<211> LENGTH: 7
<212> TYPE: PRT
<213> ORGANISM: Artificial Sequence
<220> FEATURE:
<223> OTHER INFORMATION: binding peptide

<400> SEQUENCE: 411

Pro Tyr Leu Pro Ser Ile Pro
 1               5

<210> SEQ ID NO 412
<211> LENGTH: 7
<212> TYPE: PRT
<213> ORGANISM: Artificial Sequence
<220> FEATURE:
<223> OTHER INFORMATION: binding peptide

<400> SEQUENCE: 412

Pro Ser Leu Pro Ser Ile Pro
 1               5

<210> SEQ ID NO 413
<211> LENGTH: 7
<212> TYPE: PRT
```

```
<213> ORGANISM: Artificial Sequence
<220> FEATURE:
<223> OTHER INFORMATION: binding peptide

<400> SEQUENCE: 413

Lys His Pro Gln Ser Pro Pro
 1               5

<210> SEQ ID NO 414
<211> LENGTH: 7
<212> TYPE: PRT
<213> ORGANISM: Artificial Sequence
<220> FEATURE:
<223> OTHER INFORMATION: binding peptide

<400> SEQUENCE: 414

Pro Pro Arg Tyr Ala Glu Leu
 1               5

<210> SEQ ID NO 415
<211> LENGTH: 7
<212> TYPE: PRT
<213> ORGANISM: Artificial Sequence
<220> FEATURE:
<223> OTHER INFORMATION: binding peptide

<400> SEQUENCE: 415

Ser Gln Leu Ala Leu Gln Gln
 1               5

<210> SEQ ID NO 416
<211> LENGTH: 7
<212> TYPE: PRT
<213> ORGANISM: Artificial Sequence
<220> FEATURE:
<223> OTHER INFORMATION: binding peptide

<400> SEQUENCE: 416

Asp Ser Asn Ser Ile Gln Val
 1               5

<210> SEQ ID NO 417
<211> LENGTH: 7
<212> TYPE: PRT
<213> ORGANISM: Artificial Sequence
<220> FEATURE:
<223> OTHER INFORMATION: binding peptide

<400> SEQUENCE: 417

Asn Trp His Pro Thr Leu Pro
 1               5

<210> SEQ ID NO 418
<211> LENGTH: 7
<212> TYPE: PRT
<213> ORGANISM: Artificial Sequence
<220> FEATURE:
<223> OTHER INFORMATION: binding peptide

<400> SEQUENCE: 418

Ser Pro Thr Leu Pro Pro Pro
 1               5

<210> SEQ ID NO 419
<211> LENGTH: 12
<212> TYPE: PRT
<213> ORGANISM: Artificial Sequence
```

```
<220> FEATURE:
<223> OTHER INFORMATION: binding peptide

<400> SEQUENCE: 419

Ser Lys His Pro Pro Ser Ser Pro His Gln Ser Pro
1               5                   10

<210> SEQ ID NO 420
<211> LENGTH: 7
<212> TYPE: PRT
<213> ORGANISM: Artificial Sequence
<220> FEATURE:
<223> OTHER INFORMATION: binding peptide

<400> SEQUENCE: 420

His Asp Trp Ala His Pro Leu
1               5

<210> SEQ ID NO 421
<211> LENGTH: 7
<212> TYPE: PRT
<213> ORGANISM: Artificial Sequence
<220> FEATURE:
<223> OTHER INFORMATION: binding peptide

<400> SEQUENCE: 421

Met Thr Ser His Thr Gln Ala
1               5

<210> SEQ ID NO 422
<211> LENGTH: 12
<212> TYPE: PRT
<213> ORGANISM: Artificial Sequence
<220> FEATURE:
<223> OTHER INFORMATION: binding peptide

<400> SEQUENCE: 422

Glu Pro Thr Thr Thr Thr Leu Pro Thr Val Gly Arg
1               5                   10

<210> SEQ ID NO 423
<211> LENGTH: 7
<212> TYPE: PRT
<213> ORGANISM: Artificial Sequence
<220> FEATURE:
<223> OTHER INFORMATION: binding peptide

<400> SEQUENCE: 423

Gln Ala His Asn Phe Thr Ser
1               5

<210> SEQ ID NO 424
<211> LENGTH: 12
<212> TYPE: PRT
<213> ORGANISM: Artificial Sequence
<220> FEATURE:
<223> OTHER INFORMATION: binding peptide

<400> SEQUENCE: 424

Lys Val Ser Arg Glu Asn Tyr Thr Leu Val Ala Leu
1               5                   10

<210> SEQ ID NO 425
<211> LENGTH: 12
<212> TYPE: PRT
<213> ORGANISM: Artificial Sequence
<220> FEATURE:
```

```
<223> OTHER INFORMATION: binding peptide

<400> SEQUENCE: 425

Thr Val Leu Ser Pro Leu Thr Gln Thr Leu Tyr Phe
1               5                   10

<210> SEQ ID NO 426
<211> LENGTH: 12
<212> TYPE: PRT
<213> ORGANISM: Artificial Sequence
<220> FEATURE:
<223> OTHER INFORMATION: binding peptide

<400> SEQUENCE: 426

Ile Thr Phe Asp Arg Thr Gln Gln Arg Val Asp Asp
1               5                   10

<210> SEQ ID NO 427
<211> LENGTH: 6
<212> TYPE: PRT
<213> ORGANISM: Artificial Sequence
<220> FEATURE:
<223> OTHER INFORMATION: binding peptide

<400> SEQUENCE: 427

Tyr Thr Lys Pro Tyr Pro
1               5

<210> SEQ ID NO 428
<211> LENGTH: 12
<212> TYPE: PRT
<213> ORGANISM: Artificial Sequence
<220> FEATURE:
<223> OTHER INFORMATION: binding peptide

<400> SEQUENCE: 428

His Tyr Ser Ser Gln Ser Asn Leu Ala Asp Ser His
1               5                   10

<210> SEQ ID NO 429
<211> LENGTH: 7
<212> TYPE: PRT
<213> ORGANISM: Artificial Sequence
<220> FEATURE:
<223> OTHER INFORMATION: binding peptide

<400> SEQUENCE: 429

Ser Thr Val Leu Leu Thr Asp
1               5

<210> SEQ ID NO 430
<211> LENGTH: 7
<212> TYPE: PRT
<213> ORGANISM: Artificial Sequence
<220> FEATURE:
<223> OTHER INFORMATION: binding peptide

<400> SEQUENCE: 430

Leu Thr Pro Ser Ser Ala Pro
1               5

<210> SEQ ID NO 431
<211> LENGTH: 7
<212> TYPE: PRT
<213> ORGANISM: Artificial Sequence
<220> FEATURE:
<223> OTHER INFORMATION: binding peptide
```

```
<400> SEQUENCE: 431

Asp Met Pro Pro Trp Arg Asp
1               5

<210> SEQ ID NO 432
<211> LENGTH: 12
<212> TYPE: PRT
<213> ORGANISM: Artificial Sequence
<220> FEATURE:
<223> OTHER INFORMATION: binding peptide

<400> SEQUENCE: 432

His Ala Pro Phe Pro Arg Leu Thr Glu Ile Ser Gln
1               5                   10

<210> SEQ ID NO 433
<211> LENGTH: 7
<212> TYPE: PRT
<213> ORGANISM: Artificial Sequence
<220> FEATURE:
<223> OTHER INFORMATION: binding peptide

<400> SEQUENCE: 433

Val Asp Leu Ser Ser Val Pro
1               5

<210> SEQ ID NO 434
<211> LENGTH: 50
<212> TYPE: DNA
<213> ORGANISM: Artificial Sequence
<220> FEATURE:
<223> OTHER INFORMATION: binding peptide
<220> FEATURE:
<221> NAME/KEY: misc_feature
<222> LOCATION: (17)...(37)
<223> OTHER INFORMATION: n = A,T,C or G

<400> SEQUENCE: 434
actacggcga ctcctcnnnn nnnnnnnnnn nnnnnnnatt agatctgggg          50

<210> SEQ ID NO 435
<211> LENGTH: 21
<212> TYPE: DNA
<213> ORGANISM: Artificial Sequence
<220> FEATURE:
<223> OTHER INFORMATION: binding peptide

<400> SEQUENCE: 435
ttccggagtc gaggacgaaa c                                         21

<210> SEQ ID NO 436
<211> LENGTH: 27
<212> TYPE: DNA
<213> ORGANISM: Artificial Sequence
<220> FEATURE:
<223> OTHER INFORMATION: binding peptide

<400> SEQUENCE: 436
aaggatccat caacatgatc agccaag                                   27

<210> SEQ ID NO 437
<211> LENGTH: 38
<212> TYPE: DNA
<213> ORGANISM: Artificial Sequence
<220> FEATURE:
<223> OTHER INFORMATION: primer
```

```
<220> FEATURE:
<221> NAME/KEY: misc_feature
<222> LOCATION: (1)...(21)
<223> OTHER INFORMATION: n = A,T,C or G

<400> SEQUENCE: 437
nnnnnnnnnn nnnnnnnnnn nccttcccc gagggcgg                              38

<210> SEQ ID NO 438
<211> LENGTH: 38
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)...(21)
<223> OTHER INFORMATION: n = A,T,C or G

<400> SEQUENCE: 438
nnnnnnnnnn nnnnnnnnnn naacatctcg gaggttgg                              38

<210> SEQ ID NO 439
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (13)...(33)
<223> OTHER INFORMATION: n = A,T,C or G

<400> SEQUENCE: 439
gagggcggca acnnnnnnnn nnnnnnnnnn nnngatgacg agactttcac c               51

<210> SEQ ID NO 440
<211> LENGTH: 50
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (12)...(32)
<223> OTHER INFORMATION: n = A,T,C or G

<400> SEQUENCE: 440
gtctcgtcat cnnnnnnnnn nnnnnnnnnn nngttgccgc cctcggggaa                 50

<210> SEQ ID NO 441
<211> LENGTH: 39
<212> TYPE: DNA
<213> ORGANISM: Artificial Sequence
<220> FEATURE:
<223> OTHER INFORMATION: primer

<400> SEQUENCE: 441
tcccttctta acgctactaa gaccttctcg gatgtcgag                             39

<210> SEQ ID NO 442
<211> LENGTH: 38
<212> TYPE: DNA
<213> ORGANISM: Artificial Sequence
<220> FEATURE:
<223> OTHER INFORMATION: primer

<400> SEQUENCE: 442
```

-continued

```
cttagtagcg ttaagaaggg aaactccgtt gattgtcc                            38

<210> SEQ ID NO 443
<211> LENGTH: 51
<212> TYPE: DNA
<213> ORGANISM: Artificial Sequence
<220> FEATURE:
<223> OTHER INFORMATION: primer

<400> SEQUENCE: 443
gagggcggca actcccttct taacgctact aaggatgacg agactttcac c            51

<210> SEQ ID NO 444
<211> LENGTH: 50
<212> TYPE: DNA
<213> ORGANISM: Artificial Sequence
<220> FEATURE:
<223> OTHER INFORMATION: primer

<400> SEQUENCE: 444
gtctcgtcat ccttagtagc gttaagaagg gagttgccgc cctcgggaa               50

<210> SEQ ID NO 445
<211> LENGTH: 12
<212> TYPE: PRT
<213> ORGANISM: Artificial Sequence
<220> FEATURE:
<223> OTHER INFORMATION: stained peptide (STP) #1

<400> SEQUENCE: 445

Gly Gly His Gly Gly Tyr Gly Tyr Leu Pro Ser Arg
 1               5                   10

<210> SEQ ID NO 446
<211> LENGTH: 14
<212> TYPE: PRT
<213> ORGANISM: Artificial Sequence
<220> FEATURE:
<223> OTHER INFORMATION: stained peptide (STP) #2

<400> SEQUENCE: 446

Gly Gly His Gly Gly Cys Tyr Gly Tyr Leu Pro Ser Arg Cys
 1               5                   10
```